US011198899B2

(12) United States Patent
Birnboim et al.

(10) Patent No.: US 11,198,899 B2
(45) Date of Patent: Dec. 14, 2021

(54) COMPOSITION AND METHOD FOR STABILIZING NUCLEIC ACIDS IN BIOLOGICAL SAMPLES

(71) Applicant: DNA Genotek Inc., Kanata (CA)

(72) Inventors: Hyman Chaim Birnboim, Ottawa (CA); Lindsay Pozza, Dunrobin (CA); Carlos Alberto Merino Hernandez, Nepean (CA); Evgueni Vladimirovitch Doukhanine, Ottawa (CA)

(73) Assignee: DNA Genotek Inc., Kanata (CA)

(*) Notice: Subject to any disclaimer, the term of this patent is extended or adjusted under 35 U.S.C. 154(b) by 0 days.

(21) Appl. No.: 16/595,273

(22) Filed: Oct. 7, 2019

(65) Prior Publication Data

US 2020/0239931 A1 Jul. 30, 2020

Related U.S. Application Data

(62) Division of application No. 15/124,060, filed as application No. PCT/CA2015/050173 on Mar. 6, 2015, now Pat. No. 10,435,735.

(60) Provisional application No. 61/949,692, filed on Mar. 7, 2014, provisional application No. 62/057,769, filed on Sep. 30, 2014.

(51) Int. Cl.
*C12Q 1/6806* (2018.01)
*A61K 31/711* (2006.01)
*C12N 15/10* (2006.01)

(52) U.S. Cl.
CPC .......... *C12Q 1/6806* (2013.01); *A61K 31/711* (2013.01); *C12N 15/1003* (2013.01)

(58) Field of Classification Search
CPC ...... C12Q 1/6806; C12Q 1/68; A61K 31/711; C12N 15/1003; C12N 15/10
See application file for complete search history.

(56) References Cited

U.S. PATENT DOCUMENTS

| | | | |
|---|---|---|---|
| 4,663,161 A * | 5/1987 | Mannino | A61K 9/1271 264/4.6 |
| 4,914,023 A * | 4/1990 | Philo | G01N 33/581 435/7.92 |
| 5,786,208 A | 7/1998 | Clark et al. | |
| 5,837,452 A | 11/1998 | Clark et al. | |
| 5,910,407 A | 6/1999 | Vogelstein et al. | |
| 6,084,091 A | 7/2000 | Müller et al. | |
| 6,084,094 A | 7/2000 | Henshilwood et al. | |
| 6,090,793 A * | 7/2000 | Zimmermann | A23L 29/256 514/54 |
| 6,187,546 B1 | 2/2001 | O'Neill | |
| 6,270,970 B1 | 8/2001 | Smith et al. | |
| 6,383,393 B1 | 5/2002 | Colpan et al. | |
| 6,448,002 B1 | 9/2002 | Hillebrand et al. | |
| 6,551,777 B1 | 4/2003 | Shuber et al. | |
| 6,849,403 B1 | 2/2005 | Shuber | |
| 6,852,495 B2 | 2/2005 | Kojima | |
| 6,989,249 B2 | 1/2006 | Nalin et al. | |
| 6,992,182 B1 | 1/2006 | Muller et al. | |
| 7,029,840 B2 | 4/2006 | McMillian | |
| 7,270,953 B2 | 9/2007 | Hollander et al. | |
| 7,482,116 B2 * | 1/2009 | Birnboim | B01L 3/5082 435/6.1 |
| 7,935,483 B2 | 5/2011 | Kamata et al. | |
| 8,158,357 B2 | 4/2012 | Birnboim et al. | |
| 8,293,467 B2 | 10/2012 | Fischer et al. | |
| 8,405,379 B1 | 3/2013 | Montagnier | |
| 8,470,536 B2 | 6/2013 | Birnboim et al. | |
| 2002/0004206 A1 | 1/2002 | Berger et al. | |
| 2003/0013112 A1 | 1/2003 | Sprenger Haussels | |
| 2003/0049675 A1 | 3/2003 | Nalin et al. | |
| 2003/0073830 A1 | 4/2003 | Heath et al. | |
| 2003/0091989 A1 | 5/2003 | Davis et al. | |
| 2003/0109548 A1 | 7/2003 | Royt et al. | |
| 2003/0215954 A1 | 11/2003 | Cockerill, III et al. | |
| 2003/0229222 A1 | 12/2003 | Kojima | |
| 2004/0014104 A1 | 1/2004 | Shuber | |
| 2004/0019196 A1 | 1/2004 | Bair, Jr. et al. | |
| 2004/0038269 A1 | 2/2004 | Birnboim | |
| 2004/0049805 A1 | 3/2004 | Lerchl et al. | |
| 2004/0050700 A1 * | 3/2004 | Lopez-Canovas | C12Q 1/6806 204/457 |
| 2004/0111763 A1 | 6/2004 | Heinz et al. | |

(Continued)

FOREIGN PATENT DOCUMENTS

| CA | 2142910 | 1/1995 |
|---|---|---|
| CA | 2315257 A1 | 7/1999 |

(Continued)

OTHER PUBLICATIONS

Azelee et al. Indian Journal of Geo-Marine Sciences. 2014. 43(3):372-376. (Year: 2014).*
Preliminary Office Action dated Nov. 19, 2019 on Brazilian Patent Application No. BR112016020659-2.
First Office Action dated May 20, 2019 on Israeli Patent Application No. 247662 (Translation Only).
Notice of Reasons for Rejection dated Oct. 8, 2019 on Japanese Patent Application No. 2016-572863 (Translation Only).

(Continued)

*Primary Examiner* — Joseph G. Dauner
(74) *Attorney, Agent, or Firm* — Cook Alex Ltd.

(57) ABSTRACT

Methods, compositions, and kits for stabilizing both human and microbial deoxyribonucleic acid (DNA) present in complex biological samples, such as feces, are disclosed. In particular, aqueous compositions for stabilizing DNA contained in biological samples at ambient temperature are disclosed, together with associated methods and kits using same. In one aspect, the compositions comprise a chelating agent present at a concentration of at least about 150 mM, and the composition has a pH of at least about 9.5.

31 Claims, 25 Drawing Sheets

Specification includes a Sequence Listing.

(56) References Cited

U.S. PATENT DOCUMENTS

| | | | |
|---|---|---|---|
| 2004/0157219 A1 | 8/2004 | Lou et al. |
| 2004/0157223 A1 | 8/2004 | Lou et al. |
| 2005/0181363 A1 | 8/2005 | Kamata et al. |
| 2005/0277121 A1 | 12/2005 | Pasloske et al. |
| 2005/0282202 A1 | 12/2005 | Brolaski et al. |
| 2006/0029972 A1 | 2/2006 | Lorenz |
| 2007/0015177 A1 | 1/2007 | Maron et al. |
| 2007/0031880 A1 | 2/2007 | Lou et al. |
| 2007/0135515 A1* | 6/2007 | Bringmann ............ A61P 31/00 |
| | | | 514/450 |
| 2007/0141582 A1 | 6/2007 | Li et al. |
| 2007/0178508 A1 | 8/2007 | Kamata et al. |
| 2008/0124714 A1 | 5/2008 | Shuber et al. |
| 2009/0123976 A1 | 5/2009 | Birnboim et al. |
| 2009/0253127 A1 | 10/2009 | Gaudreau et al. |
| 2010/0099149 A1 | 4/2010 | Birnboim et al. |
| 2010/0121046 A1 | 5/2010 | Ahlquist et al. |
| 2010/0245250 A1 | 9/2010 | Linegar et al. |
| 2010/0255481 A1 | 10/2010 | Akesaka et al. |
| 2010/0273218 A1 | 10/2010 | Birnboim et al. |
| 2011/0060137 A1 | 3/2011 | Tanigami et al. |
| 2011/0183328 A1 | 7/2011 | Taylor et al. |
| 2011/0183332 A1 | 7/2011 | Nagaoka et al. |
| 2011/0189673 A1 | 8/2011 | Tanigami et al. |
| 2011/0236895 A1 | 9/2011 | Tanigami et al. |
| 2011/0244461 A1 | 10/2011 | Tanigami et al. |
| 2011/0300550 A1 | 12/2011 | Tanigami |
| 2012/0052572 A1 | 3/2012 | Whitney et al. |
| 2012/0064525 A1 | 3/2012 | Asakura et al. |
| 2012/0064535 A1 | 3/2012 | Tanigami et al. |
| 2012/0083597 A1 | 4/2012 | Okamoto et al. |
| 2012/0100529 A1 | 4/2012 | Fischer et al. |
| 2012/0164648 A1 | 6/2012 | Han et al. |
| 2012/0288956 A1 | 11/2012 | Ahlquist et al. |
| 2013/0071847 A1 | 3/2013 | Burnett et al. |
| 2013/0195804 A1 | 8/2013 | Borody |
| 2013/0209997 A1 | 8/2013 | Whitney et al. |

FOREIGN PATENT DOCUMENTS

| | | | | |
|---|---|---|---|---|
| CA | 2384368 A1 | 3/2001 |
| CA | 2515039 A1 | 8/2004 |
| CA | 2522446 A1 | 11/2004 |
| CA | 2567720 A1 | 12/2005 |
| CA | 2567599 A1 | 7/2006 |
| CA | 2664696 A1 | 4/2008 |
| CA | 2703884 A1 | 5/2009 |
| CA | 2806670 A1 | 2/2012 |
| CA | 2806734 A1 | 2/2012 |
| CA | 2807242 A1 | 2/2012 |
| EP | 0338591 A2 | 10/1989 |
| EP | 0487028 A2 | 5/1992 |
| EP | 0939118 A1 | 9/1999 |
| EP | 1238103 A1 | 9/2002 |
| EP | 1362927 A1 | 11/2003 |
| EP | 1391520 A1 | 2/2004 |
| EP | 1513952 A2 | 3/2005 |
| EP | 1527172 A1 | 5/2005 |
| EP | 1506995 B1 | 10/2009 |
| EP | 2110442 A1 | 10/2009 |
| EP | 2218791 A1 | 8/2010 |
| EP | 2218792 A1 | 8/2010 |
| EP | 2278331 A1 | 2/2011 |
| EP | 2314677 A1 | 4/2011 |
| EP | 2338989 A1 | 6/2011 |
| EP | 2392670 A1 | 12/2011 |
| EP | 2535428 A2 | 12/2012 |
| EP | 3114225 A1 * | 1/2017 | ......... C12N 15/1003 |
| JP | 05099923 A | 4/1993 |
| JP | 2004008094 A | 1/2004 |
| JP | 2004008107 A | 1/2004 |
| JP | 4092139 B2 | 5/2008 |
| JP | 4092141 B2 | 5/2008 |
| RU | 2241004 C2 | 11/2004 |
| WO | 9320235 A1 | 10/1993 |
| WO | 9719191 A1 | 5/1997 |
| WO | 9812351 A1 | 3/1998 |
| WO | 9858081 A1 | 12/1998 |
| WO | 0008136 A1 | 2/2000 |
| WO | 0029618 A1 | 5/2000 |
| WO | 0031303 A2 | 6/2000 |
| WO | 0050640 A1 | 8/2000 |
| WO | 0066606 A1 | 11/2000 |
| WO | 0142502 A2 | 6/2001 |
| WO | 0142503 A2 | 6/2001 |
| WO | 02059379 A2 | 8/2002 |
| WO | 03033739 A2 | 4/2003 |
| WO | 03097831 A1 | 11/2003 |
| WO | 03104251 A2 | 12/2003 |
| WO | 2004072229 A2 | 8/2004 |
| WO | 2004094635 A2 | 11/2004 |
| WO | 2005113769 A1 | 12/2005 |
| WO | 2005123960 A1 | 12/2005 |
| WO | 2006073472 A2 | 7/2006 |
| WO | 2008021995 A1 | 2/2008 |
| WO | 2008089198 A1 | 7/2008 |
| WO | 2010028382 A2 | 3/2010 |
| WO | 2008152980 A1 | 8/2010 |
| WO | 2010123908 A1 | 10/2010 |
| WO | 2012018638 A2 | 2/2012 |
| WO | 2012145390 A2 | 10/2012 |

OTHER PUBLICATIONS

First Office Action dated Jul. 29, 2019 on Mexican Patent Application No. MX/a/2016/011495 (Translation Only).
English translation of Second Office Action dated Oct. 17, 2019 on Russian Patent Application No. 2016138077.
English translation of Decision to Grant dated Feb. 10, 2020 on Russian Patent Application No. 2016138077.
English translation of Wang Yun-xiang et al., Biochemistry. Huazhong: University of Science & Technology Press, 2011 pp. 80.
E.E Daniel et al, vol. 43, "On the mechanisms whereby EDTA. EGTA. DTPA. OXALATE. Desferrioxamine, and 1,10-phenanthroline affect contractility of rat uterus" Canadian Journal of Physiology and Pharmacology vol. 43, (1965) pp. 111-136.
English translation of Xu Yan-die, Application of Coordination Chemistry in Industry. Higher Education Press, 1989 pp. 12.
English translation of Dong Weixian, Analytical Chemistry Lecture Part and Learning Instructions (II). Beijing: Open University Press, 1963 pp. 281.
English translation of Yan Xuan-Shen et al., Ionic Equilibrium and Chemical Reactions in Aqueous Solutions. Higher Education Press, 1993 pp. 109.
Third Office Action and Search Report dated Dec. 10, 2019 on Chinese Patent Application No. 2015800159646.
First Examination Report dated Jun. 29, 2020 on Australian Patent Application No. 2015226811.
First Office Action dated May 20, 2021 on Canadian Patent Application No. 2,941,764.
Office Action dated Dec. 24, 2020 on Israeli Patent Application No. 247662 (Translation Only).
First Examination Report dated Apr. 28, 2020 on Indian Patent Application No. 201627032089.
Office Action dated Dec. 30, 2020 on Korean Patent Application No. 10-2016-7027593 (Translation Only).
Office Action dated Mar. 19, 2020 on Qatar Patent Application No. QA/201609/00399 (Translation Only).
Office Action dated Apr. 16, 2020 on Saudia Arabia Patent Application No. 516371797 (Translation Only).
Office Action dated Oct. 22, 2020 on Saudia Arabia Patent Application No. 516371797 (Translation Only).
Boom, R., et al., "Rapid and Simple Method for Purification of Nucleic Acids." Journal of clinical microbiology 28 3 (1990): 495-503 .
Caldas, C., et al. "Detection of K-ras mutations in the stool of patients with pancreatic adenocarcinoma and pancreatic ductal hyperplasia." Cancer research 54 13 (1994): 3568-73 .

(56) References Cited

OTHER PUBLICATIONS

Van Der Hoek, L., et al. "Isolation of human immunodeficiency virus type 1 (HIV-1) RNA from feces by a simple method and difference between HIV-1 subpopulations in feces and serum." Journal of clinical microbiology 33 3 (1995): 581-8.

Van Der Giessen, J., et al., "Amplification of 16S rRNA sequences to detect Mycobacterium paratuberculosis." Journal of Medical Microbiology 36 4 (1992): 255-63.

Claassen, S., et al., "A comparison of the efficiency of five different commercial DNA extraction kits for extraction of DNA from faecal samples." Journal of Microbiological Methods 94 (2013): 103-110.

Deuter, R., et al., "A method for preparation of fecal DNA suitable for PCR." Nucleic acids research 23 18 (1995) 3800-1.

Holland, J., et al., "PCR Detection of *Escherichia coli* O157:H7 Directly from Stools: Evaluation of Commercial Extraction Methods for Purifying Fecal DNA." Journal of Clinical Microbiology 38 (2000): 4108-4113.

Loktionov, A., et al., "Quantitation of DNA from exfoliated colonocytes isolated from human stool surface as a novel noninvasive screening test for colorectal cancer." Clinical cancer research : an official journal of the American Association for Cancer Research 4 2 (1998): 337-42.

Machiels, B., et al., "New protocol for DNA extraction of stool." BioTechniques 28 2 (2000): 286-90.

Mcorist, A., et al., "A comparison of five methods for extraction of bacterial DNA from human faecal samples." Journal of microbiological methods 50 2 (2002): 131-9.

Palladino, S., et al., "Rapid Detection of vanA and vanB Genes Directly from Clinical Specimens and Enrichment Broths by Real-Time Multiplex PCR Assay." Journal of Clinical Microbiology 41 (2003): 2483-2486.

Sidransky, D., et al., "Identification of ras oncogene mutations in the stool of patients with curable colorectal tumors." Science 256 5053 (1992): 102-5.

Dawson, R., et al., "Data for Biochemical Research." (1986—3rd Edition), p. 400-405, Clarendon Press Oxford.

Olson, J., et al., "DNA Stabilization Is Critical for Maximizing Performance of Fecal DNA-Based Colorectal Cancer Tests." Diagnostic Molecular Pathology vol. 14 (2005): 183-191.

Brusa, T., et al., "Oxygen Tolerance of Anaerobic Bacteria Isolated Fom Human Feces." Current Microbiology (1989): vol. 19, 39-43.

Wu, G.D., et al., "Linking Long-Term Dietary Patterns with Gut Microbial Enterotypes." Science vol. 334 (2011): 105-108.

Walker A. W., et al., "Dominant and diet-responsive groups of bacteria within the human colonic microbiota." The ISME Journal vol. 5 (2011): 220-230.

Van Nood, E., et al.,"Duodenal Infusion of Donor Feces for Recurrent Clostridium Difficile." The New England Journal of Medicine, vol. 368, No. 5 (2013): 407-15.

Song, Y., et al., "Microbiota Dynamics in Patients Treated with Fecal Microbiota Transplantation for Recurrent Clostridium difficile Infection." PLOS One vol. 8, Issue 11 (2013): 1-11.

Sillen, L.G., et al., Book and Media Review of "Stability Constants of Metal-Ion Complexes," Journal of Chemical Education, Sep. 1965, p. 521, vol. 42, No. 9.

Parsonnet, J., et al., "Helicobacter Pylori Infection and the Risk of Gastric Carcinoma." The New England Journal of Medicine, vol. 325., No. 16 (1991): 1127-31.

O'Sullivan, D.. "Methods for Analysis of the Intestinal Microflora." Current Issues in Intestinal Microbiology, vol. 1, No. 2 (2000): 39-50.

Moore, W. E.C., et al., "Intestinal Floras of Populations That Have a High Risk of Colon Cancer." Applied and Environmental Microbiology, vol. 61, No. 9 (1995): 3202-3207, American Society of Microbiology.

Mcinnes, P. & Cutting, M., Manual of Procedures for Human Microbiome Project Core Microbiome Sampling Protocol A HMP Protocol #07-001 Version No. 12.0, Jul. 29, 2010.

Ley, R.E., et al., Crystal Ball—2007 Environmental Microbiology (2007) vol. 9, No. 1, p. 1-11, Society for Applied Microbiology and Blackwell Publishing Ltd.

Lee, Y. K., et al., "Has the Microbiota Played a Critical Role in the Evolution of the Adaptive Immune System?" Science 330 (2010): 1768-1773.

Kinross, J.M., et al., "Gut microbiome-host interactions in health and disease." Genome Medicine, vol. 3, No. 14 (2011): p. 1-12. BioMed Central Ltd.

Grenham, S., et al., "Brain-Gut-Microbe Communication in Health and Disease." Frontiers in Physiology, vol. 2, Article 94 (2011): p. 1-15.

Bahl, M., et al., "Freezing fecal samples prior to DNA extraction affects the Firmicutes to Bacteroidetes ratio determined by downstream quantitative PCR analysis." FEMS Microbiology Letters, vol. 329, (2012): p. 193-7.

Aries, V., et al., "Bacteria and the aetiology of cancer of the large bowel." Gut, vol. 10 (1969): 334-335.

Ariefdjohan, M.W, et al., "Comparison of DNA extraction kits for PCR-DGGE analysis of human intestinal microbial communities from fecal specimens." Nutrition Journa, vol. I 9, No. 23 (2010): p. 1-8.

Apajalahti, J.H.A., et al., "Selective Plating Underestimates Abundance and Shows Differential Recovery of Bifidobacterial Species from Human Feces." Applied and Environmental Microbiology vol. 69, No. 9 (2003): 5731-5735.

Extended European Search Report Issued by the European Patent Office for European Application No. 15758044.0, dated Jul. 7, 2017 (7 pages).

Cardona, S.,et al., "Storage conditions of intestinal microbiota matter in metagenomic analysis.", BMC Microbiology 2012, 12:158, http://www.biomedcentral.com/1471-2180/12/158.

Smith, B., et al., "Optimising Bacterial DNA Extraction from Faecal Samples: Comparison of Three Methods." The Open Microbiology Journal vol. 5 (2011): 14-17.

English Translation of Office Action Issued by the Patent Office of the Russian Federation for Russian Application No. 2016138077, dated Oct. 23, 2018 (8 pages).

First Office Action Issued by the State Intellectual Property Office of the People's Republic of China for Chinese Application No. 2015800159646, dated Oct. 15, 2018, with English Translation (22pages).

Notice of Reasons for Rejection dated Feb. 12, 2019 received on corresponding Japanese Patent Application No. 2016-572863, 6 pages with Translation.

Second Office Action dated Mar. 14, 2019 on corresponding Chinese Patent Application No. 2015800159646, 18 pages with Translation.

Office Action Issued by the European Patent Office for European Application No. 15758044.0, dated May 7, 2018 (4 pages).

International Search Report and Written Opinion dated May 27, 2015 for International Application No. PCT/CA2015/050173.

International Preliminary Report on Patentability dated Jun. 20, 2016 for International Application No. PCT/CA2015/050173.

\* cited by examiner

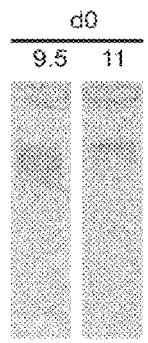
FIG. 7
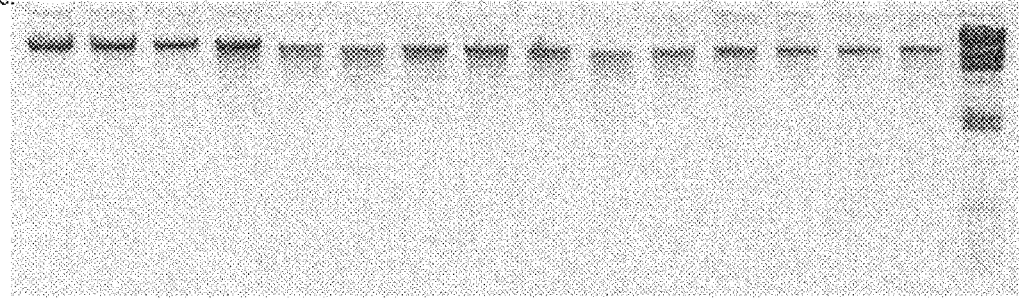
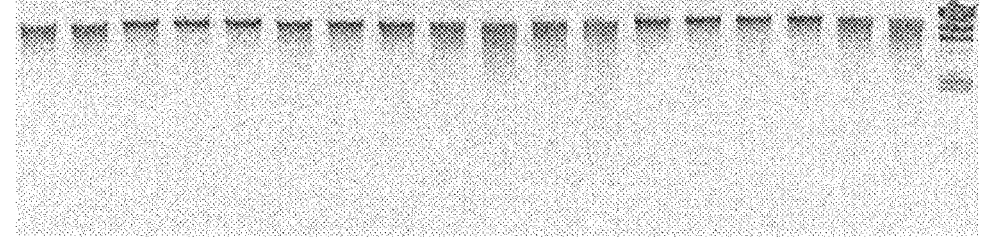
FIG. 8A

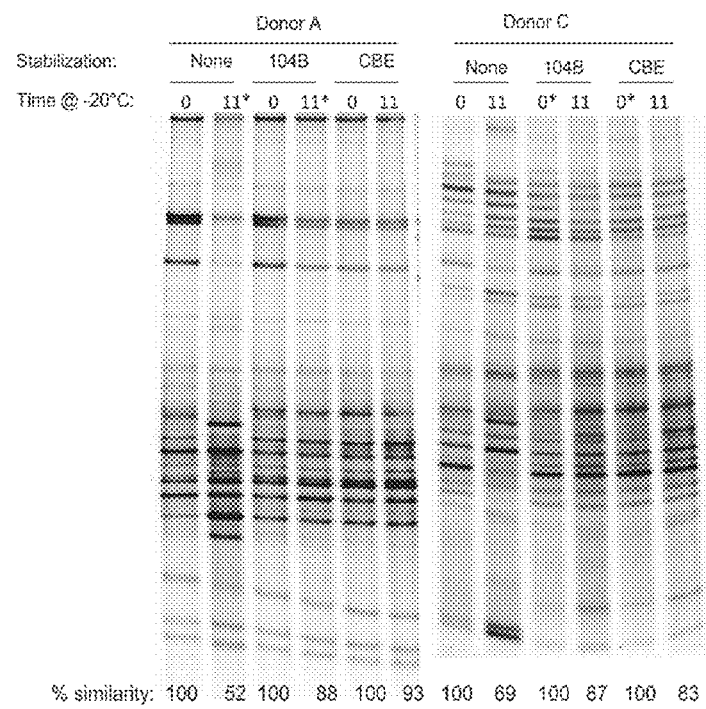
FIG. 16A FIG. 16B
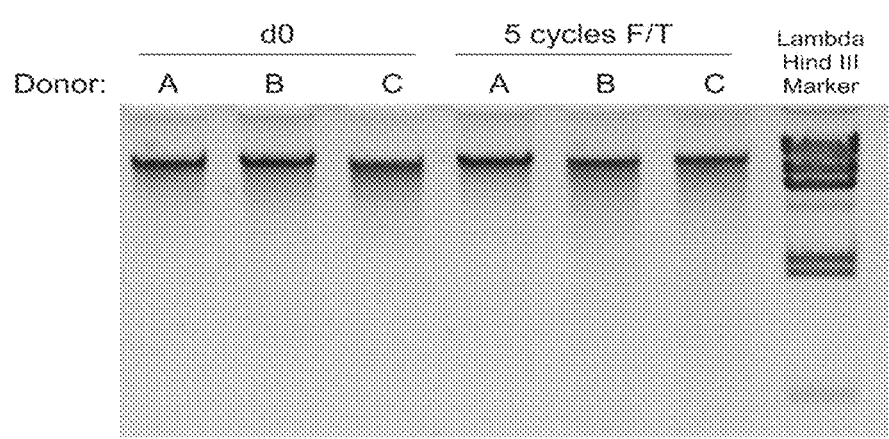
FIG. 17

COMPOSITION AND METHOD FOR STABILIZING NUCLEIC ACIDS IN BIOLOGICAL SAMPLES

CROSS REFERENCE TO RELATED APPLICATION

This application is a divisional application of copending application Ser. No. 15/124,060, filed Sep. 7, 2016, which is a U.S. national stage application of International Patent Application No. PCT/CA2015/050173, filed Mar. 6, 2015, which claims the benefit of U.S. Provisional Application No. 62/057,769, filed Sep. 30, 2014, and U.S. Provisional Application No. 61/949,692, filed Mar. 7, 2014, all of which are incorporated herein by reference in their entireties.

INCORPORATION BY REFERENCE OF MATERIAL IN ASCII TEXT FILE

This application incorporates by reference the Sequence Listing contained in the following ASCII text file: File name: SequenceListingTXTFile.txt; created Mar. 19, 2020, size: 986 bytes.

FIELD OF THE INVENTION

The present application pertains to the field of stabilizing nucleic acids in biological samples. More particularly, the present invention relates to methods and compositions for stabilizing both human and microbial deoxyribonucleic acid (DNA) present in complex biological samples, such as feces.

BACKGROUND

Feces has long been classified a potentially infectious waste product from an animal's digestive tract which is collected to test for parasites, such as pinworms and/or their eggs or to detect pathogenic bacteria and fungi in symptomatic animals and humans. Recently, however, with the rise in personalized medicine and wide-scale commercialization of pre- and pro-biotics, the diagnostic and, in particular, the prognostic value of this "waste" product has escalated. Simply a change in dietary habit has been shown to affect the microbiota or microbial community composition in feces (Walker et al, 2011; Wu et al, 2011) which, in turn, can impact health and reduce the incidence of certain diseases.

Colonization of the gastro-intestinal (GI) tract begins at birth, and the microbial community that develops over time is shaped by many influences, including the individual's genetic make-up, age, sex, nutrition, antibiotic use and other pharmaceuticals consumed, disease state, lifestyle, geographical location/environment, chemical exposure, surgical interventions and more. A diverse microbial community colonizes the intestine consisting of approximately 100 trillion bacteria which play a significant role in human health, in particular, the digestion of food, host energy metabolism, synthesis of essential vitamins, epithelium maturation, degradation of bile salts, metabolism of drugs and dietary carcinogens, as well as protecting the gut from pathogen colonization.

The 'gut microbiome' is the term given to describe this vast collection of symbiotic microorganisms in the human GI system and their collective interacting genomes. However, the understanding of these functional interactions between the gut microbiota and host physiology is in its infancy. The Human Microbiome Project revealed that the gut microbiome is approximately 150 times larger than the human genome, consisting of somewhere between 300 and 1000 bacterial species and more than 7000 strains. In most mammals, the gut microbiome is dominated by four bacterial phyla: Firmicutes, Bacteroidetes, Actinobacteria and Proteobacteria (Ley et al., 2007). A new area of work relates to the analysis of the interaction of the gut microbiome with gut parasites, viruses, yeasts, and numerous fungi, such as *Candida, Saccharomyces, Aspergillus,* and *Penicillium.* Some experts have suggested that the total information encoded by the human genome alone is not enough to carry out all of the body's biological functions (Lee and Mazmanian, 2010) and point to symbiosis between bacteria and humans as an explanation. With only around 10 percent of a human's cells being actually human, with microbes making up the remaining 90 percent, humans can be thought of as hosts for our microbe guests or super-organisms.

For many decades, intestinal microbes have been implicated in the initiation of colon cancer (Aries et al., 1969; Moore and Moore, 1995). More recently, *Helicobacter pylori* infection has been identified as a major cause of gastric (stomach) cancer, gastric lymphoma, and peptic ulcer disease (Parsonnet et al., 1991). It turns out, however, that gut microbes have more influence on how we feel and behave than we know. Due to increasing evidence that communication exists between the gut and the brain, the gut has been dubbed the 'second brain.' Evidence suggests that numerous diseases, such as cardiovascular disease, diabetes, stress/anxiety, autism, Crohn's disease, Irritable Bowel Disease (IBD), allergic disorders, metabolic syndrome, and neurologic inflammation may result from dysregulation of the gut microbiome. However, researchers are just beginning to decipher what is now termed the 'microbiome-gut-brain axis', i.e., how microorganisms colonizing the GI tract can influence biological functions beyond the gut, in particular, the molecular mechanisms or crosstalk by which the gut microbiome impacts immunological, endocrine and neurological diseases in its host (Grenham et al., 2011; Kinross et al., 2011). For instance, many microbes produce neurometabolites that are either neurotransmitters or modulators of neurotransmission, including GABA, noradrenaline, serotonin, dopamine, and acetylcholine, which act directly on nerve terminals in the gut or via enterochromaffin cells present throughout the GI tract. Carbohydrates from dietary fibre are also broken down by microbes, resulting in the production of neuroactive chemicals, such as, n-butyrate, acetate, hydrogen sulphide and propionate. In addition, microbes shed metabolites, such as proteins, carbohydrates, and other molecules, which can leave the gut and play a role in signalling disease throughout the body.

In both healthy and diseased individuals, as well as identifying the hundreds of different species making up the gut microbial community, it is critical to gain an understanding of the functionality of the consortia of bacteria as a whole. For instance, the composition of the microbiota determines competition for dietary ingredients as growth substrates, conversion of sugar into inhibitory fermentation products, production of growth substrates, release of bacteriocins (molecules toxic to other bacterial species), stimulation of the innate immune system, competition against microbes colonizing the gut wall and gut-barrier function, and more. Unfortunately, traditional microbiological culture techniques have proven largely unsuccessful in helping to determine the identity and function of members of the gut microbiome, due to significant limitations stemming from their reliance on appropriate growth nutrients and complex conditions for the entire intestinal microflora to flourish in vitro. Estimates indicate that only 20-40% (Apajalahti et al., 2003) of the total intestinal microflora can be cultivated by standard culture techniques, so the vast majority of microbial biodiversity has been missed by cultivation-based methods. This factor is further compounded by the need to ensure viability of the intestinal microflora in vitro, many of which are anaerobic (O'Sullivan, 2000).

Numerous culture media inherently select against some bacteria, in particular, ones that require extra or selective agents or bacteria in a physiological state which is not conducive to culturing directly from feces or intestinal material. Also, traditional morphological examination and biochemical tests for identifying and characterizing intestinal microflora are extremely labour-intensive, time-consuming, and lack precision, thus limiting their effectiveness for analyzing specimens from a large number of individuals and comparing the relatedness between bacterial species from different individuals. Therefore, quick methods to capture and stabilize or "snap-shot" the microbiome at the point of collection, in conjunction with culture-independent molecular tools, such as 16S ribosomal RNA gene-based approaches, TaqMan probes, digital and LATE PCR, and metagenomic sequencing, are needed to overcome these limitations and biases, so a true and detailed picture of this rich ecosystem can be revealed.

Today, approximately 1 out of every 20 hospitalized patients will contract a hospital-acquired infection (HAI). While most types of HAIs are declining, outbreaks caused by *Clostridium difficile*, a known pathobiont, are a growing problem afflicting patients in hospitals and long-term healthcare facilities. *C. difficile* infection (CDI) is believed to result from gastrointestinal dysbiosis, i.e., the disruption of the resident microbiota. Antibiotics treatment kills most bacteria in the GI tract that usually control *C. difficile*. In this altered environment, *C. difficile* replicate and produce toxins that attack the lining of the intestine, causing symptoms ranging from diarrhea to life-threatening inflammation and bleeding of the lining of the colon. According to the Centers for Disease Control and Prevention (CDC), *C. difficile* alone is linked to the deaths of 14,000 people a year in the United States. In hospitals, *C. difficile* spores shed in feces are transferred to patients and surfaces mainly via the hands of healthcare personnel who have touched a contaminated surface or item. An effective treatment against recurrent *C. difficile* infection is not widely available. Paradoxically, the primary treatment for *C. difficile* infection is the administration of more antibiotics, with about 20% of patients having recurrences within a month, and many of those have repeated attacks.

An unorthodox, alternate procedure, fecal microbiota transplantation (FMT), in which feces from one "donor" is infused into a patient's intestines, is proving to be far more effective than antibiotics at treating recurrent GI infections. By restoring disturbances to the microbial equilibrium, an infusion of feces from healthy donors appears to keep harmful bacteria, such as *C. difficile*, at bay, eradicating illness even in patients who have suffered repeated, debilitating bouts. In a small Dutch study at the University of Amsterdam, 15 of 16 patients with recurrent *C. difficile* infection were cured with duodenal infusion of donor feces, compared to only 27% of patients given a 2-week regimen of the antibiotic vancomycin (van Nood, Els et al. (2013)). It was shown that infusion of donor feces resulted in improvement in the microbial diversity in the patient's GI tract and this diversity persisted over time. Recently, Song et al. (2013) confirmed previous reports that a reduction in microbiota diversity and richness in fecal samples from recurrent *C. difficile* infection (RCDI) patients was restored after FMT to become similar to that of a healthy donor. In this longitudinal study, FMT predominantly affected Firmicutes and Proteobacteria, and the fecal microbiota continued to change in post-FMT patients for at least 16 weeks.

Importantly, the exact mechanism of action responsible for the success of FMT to treat RCDI remains unknown and there is no clinically validated set of parameters to define a suitable donor or ideal donor microbiota. An easy and effective means to collect feces samples in the field and snap-shot the sampled microbiome in a composition at ambient temperature from large numbers of individuals, both healthy donors and RCDI patients, at multiple time points is needed to map the 'core' microbiome found in the GI tract of healthy individuals in a population, upon which can be overlaid the changing microbiome of RCDI patients. Ultimately, RCDI patients in the future will be treated, not with antibiotics, but with customized probiotics (a preparation/supplement containing live bacteria that is taken orally to restore beneficial bacteria to the body) and prebiotics (non-digestible food components, such as oligosaccharides, that promote the activity of target selected groups of the GI microflora) or synbiotics (synergistic combinations of probiotics and prebiotics) to return their microbiome to a healthy state.

To avoid the risk of introducing unidentified, potentially harmful microbes, some hospitals are starting to build self-banking systems. A patient's feces can be banked to use in the future as an antidote against possible infection with hospital-acquired "super bugs." Using the patient's own feces for transplantation greatly reduces the risk of introducing harmful microbes and avoids time-consuming and costly screening of feces from unrelated donors for transmissible diseases. Unfortunately, it appears the "ecosystem" of certain people, however, makes them more susceptible to illness than others. Hence, a possible drawback associated with reintroducing a patient's own feces is that it may only provide short-term benefits and not cure them of detrimental microbes, such as *C. difficile*. In time, microbiome research may lead to the identification of 'core' or 'keystone' bacterial species that help to define human health and then develop personalized "bacteriotherapy," consisting of fully characterized, beneficial bacterial "cocktails," to supplant this crude method of transplanting "raw" feces. In fact, probiotics therapies have now been proposed for a large variety of gut-related disorders such as IBD and inflammatory bowel syndrome. Fundamentally, researchers and clinicians attempting to characterize all species of a donor's microbiota, identify diagnostic markers to predict susceptibility to disease, and ultimately provide 'personalized' health care, need to be confident that the fecal samples being tested provide a true representation or "snap-shot" of the donor's microbiome in vivo, not a 'degraded' or artificial representation of the microbial community. Hence, an effective means to immediately capture and stabilize or snap-shot the microbiome of feces at the point of collection is critical.

Colorectal cancer (CRC) has the highest cancer mortality rates in Europe and the United States. It is known that CRC is highly curable (>90%) if detected in its early stages, making early cancer screening a valuable asset. A number of sensitive examination methods have been devised over the years to detect cancer, such as double-contrast barium enema, colonoscopy, and flexible sigmoidoscopy. However, the financial costs, infrastructure, and manpower requirements associated with these procedures present formidable obstacles, not to mention being uncomfortable and invasive for the patient. In addition to costs, the low-throughput nature of these examination methods impedes their implementation for nationwide primary screening.

Presently, another method to screen for colorectal cancer is the fecal occult blood test (FOBT). This test detects the presence of haemoglobin in feces samples to determine the presence or absence of bleeding in GI tract, as an indirect predictor of CRC. While this test is not expensive, its sensitivity and positive predictive value is very low and the incidence of false-positives is high. Therefore, a sensitive, reliable, cost-effective, scalable method is in great need for both diagnosis of disease in at-risk and/or symptomatic individuals, as well as for routine diagnostic screening of the asymptomatic population. Ideally, an individual would routinely collect and stabilize a portion of their feces in the privacy of their home and then mail it to a testing facility to be screened for CRC and other diseases.

It is already accepted that direct detection and examination of tumour cells sloughed into the colonic lumen and recovered from feces is a more positive predictor of colorectal cancer than occult blood. However, the "target" or mutant human DNA, indicative of cancer or other diseases, is usually present in the biological sample at low frequency (e.g. 1% of total human DNA for CRC), often against a high background of wild-type DNA (e.g. bacterial DNA and human DNA from normal colon cells), and exposed to endogenous human DNases (e.g. deoxyribonuclease I) and/or bacterial nucleases (e.g. Micrococcal nuclease). In this complex specimen, what little "target" human DNA that exists in a fecal sample may be rapidly degraded by nucleases and environmental conditions before it even reaches the laboratory, negatively impacting clinical sensitivity of diagnostic tests. In addition to the abundance of nucleases, anaerobic bacteria, constituting over 99% of bacteria in the gut, become exposed to air as soon as feces are eliminated from the digestive tract. Air, specifically oxygen, is a toxic environment to anaerobic bacteria killing 50% within 4-5 minutes and 95-97% of anaerobes after only 20 minutes (Brusa et al., 1989). Again, acquiring a representative view or "snap-shot" of the entire microbiome and human DNA in feces is a challenge considering most fecal samples are collected at home, not in a laboratory or healthcare facility.

It is imperative to stabilize total nucleic acid in biological samples such that it does not degrade during sample handling, transport and storage. To minimize degradation of nucleic acid in biological samples, it is standard practice to transport whole samples or portions thereof on dry ice ($-78°$ C.) to centralized testing facilities where it is either thawed and processed immediately or kept frozen in storage ($-80°$ C. to $-20°$ C.). The costs, logistics and infrastructure needed to ensure collected samples are frozen immediately, kept frozen during transport to testing facilities, and stored under optimal conditions prior to analysis, poses significant challenges and risks, especially in large-scale and population-based screening applications. It can be even more challenging to provide 'representative' samples for decentralized sample analysis and still retain maximum sample integrity. It is highly desirable to develop a more robust and standardized sample-handling method and composition that captures and maintains a true representation of each sample's nucleic acid profile.

The study of the relationship between the microbiome and its human host in health and disease relies on the identification and monitoring the microbial communities over a period of time. Recent discoveries demonstrate the utility of these microbial profiles as biomarkers with prognostic and diagnostic value. It is becoming evident in the literature that due to the dynamic nature of the gut microbiome, repeated sampling of large populations over time is essential to the development of such biomarkers. These studies, known as Microbiome-Wide Association Studies (MWAS) are challenged by low donor compliance, unreliable self-collection of biological samples, high cost and cumbersome shipping and handling procedures.

Current methods for feces sampling and microbiota analysis involve the transport of specimens under conditions that have the potential to expose samples to temperatures incompatible with microbiome stabilization. Failure to properly stabilize the microbiome during sample collection, transport, processing and analysis risks obscuring the biological and clinical meaning of the microbiome profile. Consequently, proper pre-analytical procedures are necessary to ensure the best possible representation of the in vivo microbiome profile.

There is a need for compositions and methods for stabilizing nucleic acids, in particular both human and microbial DNA, in complex biological samples such as feces, during transport and storage at ambient temperatures.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a composition, method, and kit for stabilizing nucleic acid contained in a biological sample at ambient temperature.

In one aspect, there is provided a method of stabilizing nucleic acid contained in a biological sample at ambient temperature comprising the steps of: a) obtaining a biological sample; b) contacting the biological sample with an aqueous composition comprising a chelating agent, wherein the chelating agent is present at a concentration of at least about 150 mM, and wherein the composition has a pH of at least about 9.5, to form a mixture; c) homogenizing the mixture of (b) to form a homogeneous mixture; and d) storing the homogeneous mixture at ambient temperature.

In another aspect, there is provided an aqueous composition for stabilizing nucleic acid contained in a biological sample at ambient temperature, comprising a chelating agent wherein the chelating agent is present at a concentration of at least about 150 mM, wherein the composition has a pH of at least about 9.5.

In still another aspect, there is provided a kit for stabilizing nucleic acid contained in a biological sample at ambient temperature, the kit comprising: a) a sample container having a resealable closure; b) an aqueous composition comprising a chelating agent wherein the chelating agent is present at a concentration of at least about 150 mM, wherein the composition has a pH of at least about 9.5, wherein said composition is optionally contained within the sample container; c) a homogenization means, optionally contained within the sample container; d) a means to transfer the biological sample, or a portion thereof, into the sample container; and d) instructions for use.

In one embodiment, the nucleic acid is deoxyribonucleic acid (DNA).

In another embodiment, the biological sample is selected from a fecal sample, a soil sample, a sewage sample, a wastewater sample, or a water sample. In another embodiment, the biological sample is a fecal sample. In another embodiment, the fecal sample is obtained from a mammal. In yet another embodiment, the mammal is a human.

In another embodiment, the chelating agent is selected from 1,2-cyclohexanediamine tetraacetic acid (CDTA), diethylenetriamine pentaacetic acid (DTPA), tetraazacyclododecanetetraacetic acid (DOTA), tetraazacyclotetradecanetetraacetic acid (TETA), desferioxamine, or chelator analogs thereof. In another embodiment, the chelating agent is CDTA.

In another embodiment, the concentration of the chelating agent is from about 150 mM to about 500 mM, or from about 250 mM to about 350 mM. In still another embodiment, the concentration of the chelating agent is about 300 mM.

In yet another embodiment, the composition has a pH of from about 9.5 to about 11.5, or from about 10.5 to about 11.5. In another embodiment, the composition has a pH of about 11.

In still yet another embodiment, the composition further comprises at least one buffering agent capable of buffering in the pH range 9.5 to 11.5. In another embodiment, the buffering agent is beta-alanine.

In still another embodiment, the composition further comprises a water-soluble organic solvent, such as a C1-C6 alkanol. In another embodiment, the water-soluble organic solvent is ethanol. In yet another embodiment, the ethanol is present in the composition at a concentration of less than about 30% by volume. In still yet another embodiment, the ethanol is present in the composition at a concentration of less than about 24% by volume.

In another embodiment, the composition further comprises a detergent, such as sodium dodecylsulfate. In yet another embodiment, the composition further comprises an antifoaming agent, such as Antifoam A. In still yet another embodiment, the composition further comprises an antimicrobial agent, such as Triclosan or Proclin.

In yet another embodiment, the nucleic acid is microbial DNA.

In still another embodiment, the nucleic acid is microbial DNA and the method stabilizes a microbiome profile of the biological sample. In yet another embodiment, the method renders the microbiome profile of the biological sample stable for at least 7 days, at least 14 days, at least 30 days, or at least 60 days at room temperature; at least 7 days, or at least 14 days at a temperature of from about 37° C. to about 50° C.; and/or at least 30 days at −20° C.

In still another embodiment, the nucleic acid is microbial DNA and the composition/kit is for stabilizing a microbiome profile of the biological sample.

In still another embodiment, the nucleic acid is human DNA. In yet another embodiment, the method renders the human DNA stable for: at least 7 days, at least 14 days, at least 30 days, or at least 60 days at room temperature; at least 7 days, or at least 14 days at a temperature of from about 37° C. to about 50° C.; and/or at least 30 days at −20° C.

In still yet another embodiment, the method comprises homogenizing the mixture of the biological sample and the aqueous composition using a homogenization means.

In another embodiment, the homogenization means of the above-described method and kit is at least one mixing ball. In yet another embodiment, the at least one mixing ball is a stainless steel mixing ball or a tungsten carbide mixing ball. In still another embodiment, the at least one mixing ball is a stainless steel mixing ball having a diameter of about 5.6-11.1 mm and a density of at least about 7.6 g/cm3. In still yet another embodiment, the stainless steel mixing ball has a diameter of about 7.1-8.7 mm and the sample container is a round-bottom tube having an internal diameter of about 12.9 mm.

In another embodiment, the method comprises forming the mixture of the biological sample and the aqueous composition in a sample container containing the at least one mixing ball, sealing the sample container, and homogenizing the mixture by shaking the mixture in the presence of the at least one mixing ball. In yet another embodiment, the shaking is done by hand.

In other embodiments, stabilizing the nucleic acid comprises preserving the relative abundance of the nucleic acid contained in the biological sample during storage at ambient temperature.

In still another embodiment, there is provided a method of stabilizing DNA contained in a fecal sample at ambient temperature comprising the steps of: a) obtaining a fecal sample from a mammal; b) contacting the fecal sample with an aqueous composition having a pH of from about 10.5 to about 11.5 and wherein the composition comprises, consists essentially of, or consists of: CDTA in an amount of from about 250 mM to about 350 mM; β-alanine in an amount of from about 30 mM to about 70 mM; ethanol in an amount of from about 21.5% to about 23.5% by volume; sodium dodecyl sulfate in an amount of from about 0 to about 1% (w/v); and Antifoam A in an amount of from about 0 to about 0.2% (v/v); c) homogenizing the mixture of (b) to form a homogeneous mixture; and d) storing the homogeneous mixture at ambient temperature. In yet another embodiment, the aqueous composition has a pH of about 11, and comprises, consists essentially of, or consists of:

CDTA in an amount of about 300 mM; β-alanine in an amount of about 50 mM; ethanol in an amount of about 23.5% by volume; sodium dodecyl sulfate in an amount of about 0.5% (w/v); and Antifoam A in an amount of about 0.1% (v/v). In yet another embodiment, the method comprises forming the mixture of the fecal sample and the aqueous composition in a round-bottom tube having an internal diameter of about 12.9 mm and containing at least one stainless steel mixing ball having a diameter of about 5.6-11.1 mm and a density of at least about 7.6 g/cm3, sealing the round-bottom tube, and homogenizing the mixture by shaking the mixture by hand in the presence of the at least one stainless steel mixing ball. In another embodiment, the DNA is microbial DNA, and the method stabilizes a microbiome profile of the fecal sample.

In still another embodiment, there is provided an aqueous composition for stabilizing DNA contained in a fecal sample at ambient temperature, wherein the fecal sample is obtained from a mammal, wherein the composition has a pH of from about 10.5 to about 11.5, and comprises, consists essentially of, or consists of: CDTA in an amount of from about 250 mM to about 350 mM; β-alanine in an amount of from about 30 mM to about 70 mM; ethanol in an amount of from about 21.5% to about 23.5% by volume; sodium dodecyl sulfate in an amount of from about 0 to about 1% (w/v); and Antifoam A in an amount of from about 0 to about 0.2% (v/v). In yet another embodiment, the aqueous composition has a pH of about 11, and comprises, consists essentially of, or consists of: CDTA in an amount of about 300 mM; β-alanine in an amount of about 50 mM; ethanol in an amount of about 23.5% by volume; sodium dodecyl sulfate in an amount of about 0.5% (w/v); and Antifoam A in an amount of about 0.1% (v/v). In another embodiment, the DNA is microbial DNA, and the composition is for stabilizing a microbiome profile of the fecal sample.

In still yet another embodiment, there is provided a kit for stabilizing nucleic acid contained in a biological sample at ambient temperature, the kit comprising: a) a sample container having a resealable closure; b) an aqueous composition having a pH of from about 10.5 to about 11.5, and comprising, consisting essentially of, or consisting of: CDTA in an amount of from about 250 mM to about 350 mM; β-alanine in an amount of from about 30 mM to about 70 mM; ethanol in an amount of from about 21.5% to about 23.5% by volume; sodium dodecyl sulfate in an amount of from about 0 to about 1% (w/v); and Antifoam A in an amount of from about 0 to about 0.2% (v/v), wherein said composition is optionally contained within the sample container; c) a homogenization means, optionally contained within the sample container; d) a means to transfer the biological sample, or a portion thereof, into the sample container; and d) instructions for use. In another embodiment, the aqueous composition has a pH of about 11, and comprises, consists essentially of, or consists of: CDTA in an amount of about 300 mM; β-alanine in an amount of about 50 mM; ethanol in an amount of about 23.5% by volume; sodium dodecyl sulfate in an amount of about 0.5% (w/v); and Antifoam A in an amount of about 0.1% (v/v). In still another embodiment, the nucleic acid is microbial DNA and the kit is for stabilizing a microbiome profile of the biological sample. In still yet another embodiment, the homogenization means is at least one stainless steel mixing ball having a diameter of about 5.6-11.1 mm and a density of at least about 7.6 g/cm3, and the sample container is a round-bottom tube having an internal diameter of about 12.9 mm.

BRIEF DESCRIPTION OF THE FIGURES

For a better understanding of the present invention, as well as other aspects and further features thereof, reference is made to the following description which is to be used in conjunction with the accompanying drawings, where:

FIG. 7 shows an agarose gel demonstrating results from mixing fecal samples with (A) multiple glass beads and (B) stainless steel ball in the present composition;

FIGS. 8A through 8F depict agarose gels showing DNA quality upon storage in the present composition at room temperature at (A) day 0, (B) day 6, (C) day 7, (D) day 14, (E) one month, and (F) 2 months;

FIGS. 16A-B show DGGE analysis of fecal samples from 2 donors stored in the present composition at −20° C. for 11 days;

FIG. 17 shows agarose gel of fecal samples in the present composition and exposed to 5 freeze/thaw cycles;

DETAILED DESCRIPTION

Figure 1:
FIG. 1 graphically depicts differences in the microbiome profile of fecal samples from 2 donors (PCR-DGGE analysis)

It should be noted that the role of the compositions for stabilizing nucleic acid described herein is to stabilize nucleic acid and 'snap-shot' total DNA profiles in biological samples, such as fecal samples, at ambient temperature for prolonged periods of time. Extraction and isolation of nucleic acid, such as DNA, is carried out in subsequent steps using commercially available extraction kits following stabilization of the nucleic acids contained in fecal samples using the compositions described herein. Preferably, the compositions for stabilizing nucleic acid described herein do not contain chaotropic salts (e.g. guanidinium salts such as guanidinium thiocyanate (GuSCN) or guanidinium hydrochloride (GuHCl)), urea, fixatives (e.g. formalin, paraformaldehyde, etc.), reducing agents, polycations (such as polylysine or polyacrylamide), phenol or chloroform. Enzymes such as proteases (e.g. proteinase K), lysozyme, etc. are not needed to effect stabilization of the nucleic acids contained in fecal samples using the compositions described herein and are therefore preferably not included in the compositions described herein. Thus, the present compositions and methods of stabilizing nucleic acid avoid the use of costly and/or toxic compounds which often require special storage and transport conditions.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "sample" as used herein will be understood to mean any specimen that potentially contains a substance of interest, in particular a nucleic acid, and optionally a protein or other biomolecules of interest. The term "sample" can encompass a solution, such as an aqueous solution, cell, tissue, biopsy, powder, or population of one or more of the same. The sample can be a biological sample, such as saliva, sputum, buccal swab sample, serum, plasma, blood, buffy coat, pharyngeal, nasal/nasal pharyngeal or sinus swabs or secretions, throat swabs or scrapings, urine, mucous, feces/stool/excrement, rectal swabs, lesion swabs, chyme, vomit, gastric juices, pancreatic juices, gastrointestinal (GI) tract fluids or solids, semen/sperm, urethral swabs and secretions, cerebral spinal fluid, products of lactation or menstruation, egg yolk, amniotic fluid, aqueous humour, vitreous humour, cervical secretions or swabs, vaginal fluid/secretions/swabs or scrapings, bone marrow samples and aspirates, pleural fluid and effusions, sweat, pus, tears, lymph, bronchial or lung lavage or aspirates, peritoneal effusions, cell cultures and cell suspensions, connective tissue, epithelium, epithelial swabs and smears, mucosal membrane, muscle tissue, placental tissue, biopsies, exudates, organ tissue, nerve tissue, hair, skin, or nails, wherein samples of the foregoing may be obtained from for example, a vertebrate, including a mammal. A mammal can be, for example, a human, a non-human primate, cattle (such as cow, goat, or sheep), as well as a dog, cat, horse, etc.

In one embodiment, the biological sample is a fecal sample and the subject is a mammal. In another embodiment, the biological sample is a fecal sample and the subject is a human.

Other types of biological samples include plants, plant extracts, algae, soil samples, sewage, wastewater, water, environmental samples, foodstuff, cattle feed, fish feed, animal feed, swabs of contaminated or potentially infectious surfaces or equipment (e.g. meat processing surfaces), swabs from 'touch' surfaces in hospitals, nursing homes, outpatient facilities, medical institutions, or the like. In still other embodiments, the biological sample is selected from a soil sample, a sewage sample, a wastewater sample, or a water sample, any of which may be contaminated with feces.

The term "microorganism" or "microbe" as used herein, will be understood to mean any microscopic organisms and spores, including all of the prokaryotes, namely the eubacteria and archaeabacteria, and various forms of eukaryote, comprising the protozoa, fungi (e.g., yeast), algae, and animals such as rotifers and planarians. For example, the groups of bacteria most frequently detected in human feces using 16S rRNA gene sequencing include Firmicutes, Bacteroidetes, Spirochaetes, Fusobacteria, Deltaproteobacteria, Epsilonproteobacteria, Alphaproteobacteria, Betaproteobacteria, Gammaproteobacteria, Euryarchaeota, Eukarya, Desulfothiovibrio, Tm7, Cyanobacteria, Actinobacteria, Verrucomicrobia and Lentisphaerae.

The term "virus" or "virions" as used herein will be understood to mean any small infectious agent that replicates only inside the living cells of other organisms. Viruses can infect all types of life forms, from animals and plants to bacteria and archaea, and live in almost every ecosystem. Currently, there are 21 families of viruses known to cause disease in humans: Adenoviridae, Herpesviridae, Papillomaviridae, Polyomaviridae, Poxviridae, Hepadnaviridae, Parvoviridae, Astroviridae, Caliciviridae, Picomaviridae, Coronaviridae, Flaviviridae, Togaviridae, Hepeviridae, Retroviridae, Orthomyxoviridae, Arenaviridae, Bunyaviridae, Filoviridae, Paramyxoviridae, Rhabdoviridae, Reoviridae (and Hepatitis D, currently unassigned). The genetic material in a virus can be either deoxyribonucleic acid (DNA) or ribonucleic acid (RNA).

The nucleic acid to be stabilized by the compositions described herein can be DNA or RNA, including mRNA or viral RNA. In one embodiment, the nucleic acid is DNA. In another embodiment, the DNA is of human, viral, and microbial origin. In yet another embodiment, the nucleic acid to be stabilized by the compositions described herein comprises human DNA and microbial DNA.

The term "ambient temperature" as used herein refers to a range of temperatures that could be encountered by the mixture of a biological sample (e.g. fecal sample) and the nucleic acid stabilizing compositions described herein from the point of collection, during transport (which can involve relatively extreme temperatures, albeit usually for shorter periods of time (e.g. <5 days)), as well as during prolonged storage prior to analysis. In one embodiment, the temperature is ambient temperature ranging from about −20° C. to about 60° C. In another embodiment, the ambient temperature is room temperature and ranges from about 15° C. to about 30° C.

The step of contacting the fecal sample with the aqueous compositions described herein to form a mixture should be carried out as soon as possible following voiding of the feces, and the homogenizing of the mixture to form a homogeneous mixture should be carried out as soon as possible, preferably immediately, in order to stabilize the nucleic acids contained within the fecal sample.

In general, chemical stabilization of DNA and RNA in a biological sample, such as saliva, blood, sputum, feces/stool, and urine, is achieved through the use of buffers to maintain an appropriate pH, as well as the use of chelating agents to prevent the phenomenon of metal redox cycling or the binding of metal ions to the phosphate backbone of nucleic acids. The term "chelator" or "chelating agent" as used herein will be understood to mean a chemical that will form a soluble, stable complex with certain metal ions (e.g., $Ca^{2+}$ and $Mg^{2+}$), sequestering the ions so that they cannot normally react with other components, such as deoxyribonucleases (DNase) or endonucleases (e.g. type I, II and III restriction endonucleases) and exonucleases (e.g. 3' to 5' exonuclease), enzymes which are abundant in the GI tract. The main source of DNase in the GI tract is secretions of the pancreas, as well as the resident microorganisms. In the present composition, chelating agent(s) participates in the inhibition of DNase and microbial growth in biological samples. A chelator can be, for example, ethylene glycol tetraacetic acid (EGTA), (2-hydroxyethyl)ethylenediaminetriacetic acid (HEDTA), diethylene triamine pentaacetic acid (DTPA), nitrilotriacetic acid (NTA), ethylenediaminetriacetic acid (EDTA), 1,2-cyclohexanediaminetetraacetic acid (CDTA), N,N-bis(carboxymethyl)glycine, triethylenetetraamine (TETA), tetraazacyclododecanetetraacetic acid (DOTA), desferioximine, citrate anhydrous, sodium citrate, calcium citrate, ammonium citrate, ammonium bicitrate, citric acid, diammonium citrate, ferric ammonium citrate, and lithium citrate. These chelating agents may be used singly or in combination of two or more thereof. In a preferred embodiment, desirable are chelators stronger than EDTA (i.e., chelators with a higher dissociation constant than EDTA when bound to a metal), used alone or in combination, that include, but are not limited to, CDTA, DTPA, DOTA, TETA, and desferioximine, or chelator analogs thereof, in an amount from about 150 mM to about 600 mM, preferably in an amount from about 150 mM to about 500 mM, still more preferably in an amount from about 250 mM to about 350 mM, and most preferably in an amount of about 300 mM. Most desirably, the chelating agent in the present composition is CDTA.

EDTA is a chemical that is widely used in industry, laboratories, cosmetics, medicine and in some food products. Its utility is based on its ability to 'chelate' metal ions, particularly bivalent and higher valences. CDTA is less commonly used in these fields, but it shares with EDTA an ability to chelate metal ions. Importantly, the affinity of both chelators for different metal ions varies considerably. K1, a measure of affinity expressed on a log scale is shown in Table 1 (below). The first 5 chelators listed have different numbers and configurations of carboxylate (R—COO—) groups attached to nitrogen groups. In Table 1, OPT is presented for comparison as a chelator based only on nitrogen groups.

A comparison of CDTA and EDTA in Table 1 shows they are very different. The differences in log K1 values are 2.3 ($Mg^{2+}$); 2.6 ($Ca^{2+}$); 2.4 ($Mn^{2+}$); approximately 3 ($Fe^{3+}$); 3.6 ($Co^{2+}$); 0.8 ($Cu^{2+}$); 2.9 ($Zn^{2+}$). That is, CDTA binds most metals 200 to 4,000 times more tightly than EDTA.

TABLE 1

Affinity of chelators for different metal ions

| Short name | Chemical name | $K_1$ at pH 7.0 ($\log_{10}$ of stability constants)[1] | | | | | | | |
|---|---|---|---|---|---|---|---|---|---|
| | | Mg | Ca | Mn | Fe | Co | Ni | Cu | Zn |
| CDTA | Diaminocyclohexane-tetraacetatic acid | 11.0 | 13.2 | 17.4 | 28.1 [Fe(III)] | 19.6 | 19.4 | 22.0 | 19.3 |
| DTPA | Diethylaminetriamine-pentaacetic acid | 9.3 | 10.6 | 15.1 | 28.6 [Fe(III)] | 19.0 | 20.2 | 21.1 | 18.7 |
| EDTA | Ethylenediamine-tetraacetic acid | 8.7 | 10.6 | 14.0 | 23.8-25.2 [Fe(III)] (ref. 2) | 16.0 | 18.6 | 18.8 | 16.4 |
| EGTA | (Ethylenedioxy)diethlylene dinitrilo-tetraacetic acid | 5.2 | 11.0 | 12.1 | 11.8 | 12.3 | 11.8 | 17.7 | 12.9 |
| NTA | Nitrilo-triacetic acid | 5.5 | 6.5 | 7.4 | 15.9 [Fe(III)] | 10.8 | 11.5 | 13.3 | 10.4 |
| OPT | 1,10-phenanthroline | 1.5 | 0.5 | 3.9 | 5.8 | 7.3 | 8.6 | 6.3 | 6.4 |

Taken from:
[1]*Data for Biochemical Research*, RMC Dawson, DC Elliot, WH Elliot and KM Jones, 3rd edition, 1986, Claredon Press, Oxford (see pg 400-405).
2. *Stability Constants for Metal-ion Complexes*, LG Sillén and AE Martell, Supplement No.1, Special Publication No. 25, *The Chemical Society*, Burlington House, London (1971).

One consequence of this stronger ability of CDTA to complex metals is that the concentration of any free metal ion will be lower in the presence of equal concentrations of CDTA or EDTA. More importantly, however, the amount of metal ion that may be complexed to biomolecules, such as nucleic acids or proteins, will be appreciably lower. Nucleic acids in solution are known to bind metal ions and removing such metals is likely to improve their chemical stability. This may be particularly important for transition metals such as Mn, Fe, Co and Cu, which can exist in different oxidation states by gaining or losing electrons from species, such as bimolecular oxygen, superoxide anion and hydrogen peroxide. Finally, the stronger ability of CDTA to complex metals is highly beneficial in compositions developed to suppress the degradation of nucleic acid in biological samples, such as feces, known to naturally contain large amounts of DNase which require $Ca^{2+}$ and $Mg^{2+}$ to stabilize their active conformation.

TABLE 2 pK values for CDTA and EDTA

| | pKa values | | | |
|---|---|---|---|---|
| | $k_1$ | $k_2$ | $k_3$ | $k_4$ |
| CDTA | 2.4 | 3.8 | 6.1 | 12.4 |
| EDTA | 2.0 | 2.7 | 6.2 | 10.3 |

Other differences between CDTA and EDTA exist that have practical consequences in a laboratory or research setting. Possibly because of the lower $k_1$ and $k_2$ $pK_a$ values of EDTA (see Table 2 above), it is appreciably more difficult to prepare the disodium form at pH 7.0 (starting with the acid form). More concentrated solutions of CDTA than EDTA can be prepared. Finally, the disodium form of CDTA is highly soluble in ethanol, compared to the limited solubility of the disodium form of EDTA. These differences make CDTA the best choice of chelator from a manufacturing perspective.

In general, the pH of the present composition can be maintained in the desired alkaline range using one or more appropriate buffers; wherein the composition is buffered to maintain the pH of the biological sample at a suitable pH, and said composition stabilizes said nucleic acid at ambient temperature. In accordance with one embodiment, the composition comprises one, two, or more buffering agents (non-limiting examples provided, see Table 3) with pKa values, logarithmic acid dissociation constants, at 25° C. ranging from 8.0 to 12.5 to maintain the pH within the preferred range of about 9.5 to about 11.5. An acid dissociation constant, Ka, is a quantitative measure of the strength of an acid in solution. The larger the Ka value, the more dissociation of the molecules in solution and thus the stronger the acid. Due to the many orders of magnitude spanned by Ka values, a logarithmic measure of the acid dissociation constant, pKa, is more commonly used in practice. The larger the value of pKa, the smaller the extent of dissociation at any given pH, i.e., the weaker the acid.

In living organisms, acid-base homeostasis and enzyme kinetics are dependent on the pKa values of many acids and bases present in the cell and in the body. In chemistry, knowledge of pKa values is necessary for the preparation of buffer solutions and is also a prerequisite for a quantitative understanding of the interaction between acids or bases and metal ions to form complexes. One skilled in the art will understand that a given compound/buffer can buffer the pH of a solution only when its concentration is sufficient and when the pH of the solution is close (within about one pH unit) to its pKa. In one embodiment, the pH of the present composition is in the range of about 9.5 to about 11.5. In a preferred embodiment, the pH of the composition is in the range of about 10.5 to about 11.5, and preferably the pH is about 11. The amount of buffering agent(s) can be between about 1 mM and about 1 M, for example.

In accordance with certain embodiments, the composition comprises beta-alanine as the principal buffering agent to maintain the pH within the desired range of about 9.5 to about 11.5. To maintain the pH at about 11 a buffer can be selected from Table 3 with a pKa in the range of 10-12. It is worth noting that carboxylate chelating agents, such as CDTA and EDTA, can also contribute to buffering capacity in this range. However, the pKa (k4) values of CDTA and EDTA (Table 2) differ significantly. The lower pKa (k4) value of EDTA (Table 2) makes it potentially useful to help maintain the present composition at the lower end of the desired pH range. However, the higher pKa (k4) value of CDTA makes it better suited to strengthen the buffering capacity of beta-alanine (or other buffers listed in Table 3) at the upper end of the desired range (i.e. pH 11).

TABLE 3

Suitable buffers of the present composition

| $pK_a$ (25° C.) | Suitable buffers |
|---|---|
| 8.00 | EPPS, HEPPS |
| 8.05 | Tricine |
| 8.06 | Trizma, Tris |
| 8.20 | Gly-Gly (Glycylglycine) |
| 8.26 | Bicine |
| 8.30 | HEPBS |
| 8.40 | TAPS |
| 8.80 | AMPD |
| 8.90 | TABS |
| 9.00 | AMPSO |
| 9.06 | Taurine (AES) |
| 9.23 | ($pK_1$) Boric acid |
| 9.49 | CHES (2-(Cyclohexylamino)ethanesulfonic acid) |
| 9.50 | Ethanolamine |
| 9.54 | Ephedrine |
| 9.60 | CAPSO |
| 9.66 | Hydroxyproline |
| 9.70 | AMP (2-Amino-2-methyl-1-propanol) |
| 9.74 | Leucine |
| 9.78 | Glycine |
| 9.80 | Histamine |
| 9.80 | Trimethylamine |
| 9.80 | TETA |
| 9.80 | Nitrilotriacetic acid |
| 9.87 | Alpha-Alanine |
| 9.93 | Ethylenediamine |
| 10.00 | Aspartic acid |
| 10.22 | Beta-alanine |
| 10.24 | Alanine |
| 10.30 | EDTA |
| 10.33 | ($pK_2$) Carbonic acid, Carbonate |
| 10.40 | DTPA |
| 10.40 | Tyrosine |
| 10.40 | CAPS (3-(Cyclohexylamino)-1-propanesulfonic acid) |
| 10.55 | Cysteine |
| 10.56 | gamma-Aminobutyric acid or 4-aminobutanoic acid |
| 10.57 | n-Propylamine |
| 10.62 | Methylamine |
| 10.63 | Ethylamine |
| 10.64 | n-Butylamine |
| 10.68 | Proline |
| 10.70 | Ornithine |
| 10.70 | CABS (4-(Cyclohexylamino)-1-butanesulfonic acid) |
| 10.72 | Triethylamine |
| 10.72 | Lysine |
| 10.77 | Dimethylamine |
| 10.93 | Hexamethylenediamine |
| 10.93 | Diethylamine |
| 11.12 | Piperidine |

β-alanine is a particularly suitable buffer for the compositions of the present application. In one embodiment, the pH of the composition is from about 10.5 to about 11.5, and the β-alanine is present in an amount of from about 10 mM to about 100 mM, or from about 30 mM to about 70 mM, and most preferably in an amount of about 50 mM.

The term "water-soluble" or "water-miscible organic solvent" as used herein will be understood to mean any carbon-containing substance or compound, commonly a liquid, that dissolves a solute, a chemically different liquid, solid or gas. A water-soluble organic solvent can be, for example, one or more short-chain (e.g. C1-C6) alkanols that can be straight-chain or branched, such as methanol, ethanol, propanol, isopropanol, butanol, n-butanol, pentanol, hexanol, or any combination thereof. In one embodiment of the present composition, the preferred alcohol is ethanol. In another embodiment, the water-soluble organic solvent (e.g. ethanol) is present in the composition at a concentration of less than about 30% by volume, preferably less than about 24% by volume, such as from about 21.5% to about 23.5% by volume, most preferably about 23.5% by volume. In other embodiments, the water-miscible organic solvent can be absent.

Generally, in the art, it is known that more than 30% ethanol is required to denature most proteins. Over 60% ethanol or 50% isopropanol is needed to precipitate DNA from solution. Absolute ethanol or methanol is commonly used as a fixative in histology, pathology and cell biology to terminate biochemical reactions. Some proteins can be precipitated by the addition of water-miscible organic solvents, such as ethanol and acetone, in the range of 20-50% (vol./vol.). Ethanol causes dehydration of proteins or a reduction in water activity, followed by electrostatic attraction between proteins, aggregation and insolubilization. While wishing to not be bound by theory, the inventors believe the relatively small percentage of water-miscible organic solvents in the present composition has little to no fixative properties, but rather facilitates mixing and dispersion of the biological (e.g. fecal) sample and improves the solubility of other chemical compounds which may be included in the present composition. In addition, for shipping/transport of flammable liquids, it is desirable to keep organic solvents, such as ethanol, below 24% by volume in solutions for exemption from Transport of Dangerous Goods (TDG) regulations (United Nations (UN) number 1170); otherwise a solution with >24% ethanol is classified as class 3 (flammable liquids), special packaging is mandated, and transport complexity and costs increase.

The term "detergent" or "surfactant" as used herein will be understood to mean any organic compound that is amphiphilic, can disrupt non-covalent bonds in proteins, denaturing them, and causing molecules to lose their native secondary, tertiary and/or quaternary structures. A suitable detergent can be, for example, an anionic detergent, (such as, for example, sodium dodecyl sulfate (SDS), lithium dodecyl sulphate, sodium lauryl sulfate (SLS), ammonium lauryl sulfate), a cationic detergent (quaternary ammonium salts, such as, for example, cetrimonium bromide/cetyltrimethyl-ammonium bromide/hexadecyl-trimethyl-ammonium bromide or CTAB, cetyltrimethylammonium chloride (CTAC), cetylpyridinium chloride (CPC), benzalkonium chloride (BAC)), a zwitterionic surfactant (for example, betaines, 3-[(3-cholamidopropyl)dimethylammonio]-1-propane-sulfonate (CHAPS), lecithin) or a nonionic detergent (such as, for example, Tween, Triton X, or Brij). CTAB, however, is less ideal when working with DNA. Detergents can inhibit the action of DNase by destroying the complex structure of these enzymes, facilitate dispersion of the biological sample in the present composition, and help solubilize a variety of chemical species. In certain embodiments of the present composition, the detergent is SDS. In other embodiments, the detergent (e.g. SDS) can be present in the aqueous composition in an amount of from about 0-4% (w/v), preferably about 0-1% (w/v), most preferably about 0.5% (w/v).

The term "antifoaming agent" or "defoamer" as used herein will be understood to mean a chemical additive that reduces or hinders the formation of foam. The inventors observed the formation of foam during the vigorous shaking needed to rapidly and fully disperse some biological samples, in particular feces, in a tube containing certain embodiments of the present composition, comprising a detergent. Said foam hindered and, in some samples, prevented complete mixing, with and without a homogenization means. Antifoaming agents, such as Antifoam A Concentrate (Sigma-Aldrich; Cat. No. A-5633), an active silicone polymer, significantly reduced the formation of foam during said mixing of biological sample and the present composition. Thus, antifoaming agent should preferably be included in compositions containing detergent in order to minimize the formation of foam. Other examples of appropriate antifoaming agents which may be used singly or in combination of two or more include insoluble oils, polydimethylsiloxanes and other silicones, certain alcohols, stearates and glycols. In other embodiments, the antifoaming agent (e.g. Antifoam A) can be present in the aqueous composition in an amount of from about 0-1% (v/v), preferably about 0-0.2% (v/v).

The term "antimicrobial agent" as used herein will be understood to mean a substance or group of substances which reduces the rate of growth of an organism, compared to the rate of growth of the organism in their absence. A reduction in the rate of growth of an organism may be by at least 5%, more desirably, by at least 10%, even more desirably, by at least 20%, 50%, or 75%, and most desirably, by 90% or more. The definition also extends to substances which affect the viability, virulence, or pathogenicity of an organism. An antimicrobial agent can be natural (e.g., derived from bacteria), synthetic, or recombinant. An antimicrobial agent can be bacteriostatic, bactericidal, or both. An antimicrobial agent is bacteriostatic if it inhibits cell division, without affecting the viability of the inhibited cell. An antimicrobial agent is bactericidal if it causes cell death. Cell death is commonly detected by the absence of cell growth in liquid growth medium (e.g., absence of turbidity) or on a solid surface (e.g., absence of colony formation on agar). Those of skill in the art know that a substance or group of substances which is bacteriostatic at a given concentration may be bactericidal at a higher concentration. Common antimicrobial agents known in the art, include certain alcohols, Triclosan or Irgasan, and Proclin 950. Optionally, the present composition may include an antimicrobial agent such as Triclosan. In other embodiments, the antimicrobial agent (e.g. Triclosan) can be present in the aqueous composition in an amount of from about 0-2% (w/v), preferably about 0-0.5% (w/v).

The compositions described herein, when mixed with a biological sample, in particular a fecal sample, stabilize nucleic acids contained therein at ambient temperature such that the nucleic acids are stabilized upon storage of the homogenized mixture for extended periods of time.

In one embodiment, the biological sample is a fecal sample obtained from a human subject, and the nucleic acid is DNA.

Those of skill in the art will appreciate that the presence of high molecular weight DNA in a sample can give a general indication of DNA stabilization within the sample under the storage conditions. This can be assessed by agarose gel electrophoresis, which can provide an indication of the quality of the high molecular weight DNA (e.g. crisp band versus smearing) as well as a quantitative measure of the amount of high molecular weight DNA (by densitometry analysis).

In addition to stabilizing high molecular weight DNA, the compositions described herein, when mixed with a biological sample, in particular a fecal sample, stabilize nucleic acids contained therein at ambient temperature such that the relative abundance of microbial and/or human nucleic acids is maintained upon storage of the homogenized mixture for extended periods of time. A number of techniques known to those of skill in the art can be used to determine whether the relative abundance of microbial and/or human nucleic acids is maintained, for instance techniques that utilize amplification or hybridization of nucleic acids. Another technique that can be used to assess whether the relative abundance of microbial and/or human nucleic acids is maintained upon storage of the homogenized mixture for extended periods of time is PCR-DGGE analysis, described in further detail below. Targeted 16S profiles (to determine the relative abundance of operational taxonomic units (OTU's)) as well as whole-metagenomic shotgun sequencing of genomic DNA (WMS; to determine the relative abundance of microbial genes/nucleic acids) can also be used.

In one exemplary embodiment, stabilization of human DNA in particular can be assessed by determining whether DNA obtained from biological samples, such as fecal samples, incubated with the compositions and according to the methods described herein for a period of time (tstorage) retains the ability to support PCR amplification of a target human gene into a detectable product, and more particularly whether the level of amplification of PCR product is similar to that of DNA extracted and purified from the same homogenous mixture or other control mixture at time zero. As further described in the Examples below, human DNA purified from fecal samples incubated with the compositions and according to the methods described herein at T=0 and T=tstorage can be amplified in real-time, quantitative PCR (qPCR) using primers targeting a human gene, and the change in Ct values ($\Delta$Ct) resulting from T=0 and T=tstorage purified DNA aliquots can provide a quantitative measure of human DNA stability. A $\Delta$Ct value of less than about 2 indicates that the human DNA has been rendered stable over the storage time period. A $\Delta$Ct value of less than about 1 is indicative of excellent stabilization.

In one embodiment, human DNA contained in a fecal sample incubated with the compositions and according to the methods described herein is rendered stable at room temperature for at least 7 days, at least 14 days, at least 21 days, at least 30 days, or at least 60 days. In another embodiment, human DNA contained in a fecal sample incubated with the compositions and according to the methods described herein is rendered stable at elevated temperatures such as 37° C. or 50° C. for at least 7 days, or at least 14 days. In yet another embodiment, human DNA contained in a fecal sample incubated with the compositions and according to the methods described herein is rendered stable at −20° C. for at least one month (i.e. 30 days).

In another embodiment, the nucleic acid is microbial DNA and the method stabilizes a microbiome profile of the biological sample (e.g. fecal sample). As used herein, the term "microbiome profile" generally refers to the total microbial community and biomolecules within a defined environment, and their relative amounts.

As described in further detail below, stability of a microbiome profile can be determined, for instance, by carrying out PCR on DNA that has been extracted and purified from homogeneous mixtures of the biological sample and compositions described herein following storage of the homogeneous mixtures at ambient temperature for a particular time period (tstorage), using primer pairs targeting bacterial 16S rRNA genes and Denaturing Gradient Gel Electrophoresis (DGGE) analysis. Those of skill in the art will appreciate that other bacterial genes with variable and non-variable regions can be targeted, provided that there is a difference between species of interest. The resulting PCR-DGGE profile is then compared to that obtained by carrying out PCR-DGGE analysis in the same manner on DNA that has been extracted and purified from the same homogeneous mixture or other control mixture of the biological sample and compositions at time zero. In one embodiment, a microbiome profile of a biological sample such as a fecal sample can be considered to have been stabilized at ambient temperature for a certain period of time (tstorage) if the PCR-DGGE profile after (tstorage) at ambient temperature exhibits at least 75% similarity to the PCR-DGGE profile at T=0, and most preferably at least 82% similarity to the PCR-DGGE profile at T=0.

In another embodiment, stability of a microbiome profile can be determined, for instance, by amplifying and sequencing a variable region of the bacterial 16S rRNA gene (such as the V4 hypervariable region) from DNA that has been extracted and purified from homogeneous mixtures of the biological sample and compositions described herein following storage of the homogeneous mixtures at ambient temperature for a particular time period. The resulting sequencing information is then compared to that obtained by carrying out amplification and sequencing of the variable region of the bacterial 16S rRNA gene in the same manner on DNA that has been extracted and purified from the same homogeneous mixture at time zero or other control. Various forms of bioinformatics analysis of the obtained sequencing data known to those of skill in the art can be used to assess stability of the microbiome under the storage conditions, as further detailed in the Examples.

In one embodiment, the microbiome profile of a fecal sample incubated with the compositions and according to the methods described herein is rendered stable at room temperature for at least 7 days, at least 14 days, at least 21 days, at least 30 days, or at least 60 days. In another embodiment, the microbiome profile of a fecal sample incubated with the compositions and according to the methods described herein is rendered stable at elevated temperatures such as 37° C. or 50° C. for at least 7 days, or at least 14 days. In yet another embodiment, the microbiome profile of a fecal sample incubated with the compositions and according to the methods described herein is rendered stable at −20° C. for at least one month (i.e. 30 days).

The inventors have surprisingly found that extraordinarily high concentrations of a less commonly used chelating agent, CDTA, buffered to alkaline pH (pH 9.5, preferably pH 11), can be used to rapidly and effectively capture and stabilize nucleic acid and 'snap-shot' total DNA profiles in biological samples at ambient temperature for prolonged periods.

In particular, the inventors have surprisingly found that compositions buffered to a stronger alkaline pH (about pH 10.5-11.5, preferably about pH 11) show an improved stability of microbiome DNA relative to stabilizing compositions buffered to lower pH values. This could not have been predicted, and in fact was unexpected in view of the following. It is generally known that at the higher pH, deamination of cytosine will be accelerated. DNA is also known to more readily denature at the higher pH. Apurinic sites in the DNA (that occur with low frequency) will also be cleaved more readily. Thus, it is surprising that the inventors have observed that DNA/microbiome profiles appear to be more stable, based on agarose gel electrophoresis, bacterial 16S rRNA gene sequencing and DGGE, at the higher pH values.

Without being bound by theory, it is thought that the reason for the apparent improved stability is not purely "chemical". That is, the stronger alkaline pH shows an improved stability of microbiome DNA for perhaps a combination of reasons, some of which are suggested below.

It has been observed that CDTA works much better than EDTA in the compositions described herein for DNA/microbiome stabilization. The 4 pKa's for EDTA and CDTA are shown in Table 2 above. Based on these values, this means that, at alkaline pH, CDTA will have 3 negative charges, while EDTA will have 4 negative charges as the pH approaches 11. Again, without being bound by theory, it is thought that perhaps the reason for the much better performance of CDTA, compared to EDTA, is due to the lower negative charge.

The objective in a Microbiome study is to stabilize, and eventually release DNA from, all cells in equal proportion, preferably 100% of the DNA from 100% of the cells. Stability of the 'profile' of the released DNA may be better at the higher pH because this may come closer to reaching this objective. In other words, a greater extent of the bacterial DNA may be stabilized and eventually released at pH 11, compared to pH 9.5.

Once DNA is released, it needs to be protected from degradation by DNase in fecal samples. Some DNase require metal ions as co-factors; others do not. Again, without being bound by theory, it is possible that the higher pH may be more effective at inhibiting the second class of DNase.

Unknown factors (e.g. inhibitors) in feces may bind to DNA and either sequester it or block PCR amplification. It is possible that higher pH may alleviate either or both of these possibilities.

Finally, growth of bacteria must be prevented after collection of feces samples into stabilizing compositions. Otherwise, the 'profile' of DNA/microbiome will change. Higher pH may be more effective at inhibiting growth of some microbial species than lower pH (9.5).

For complex, highly variable, solid and semi-solid sample types, such as feces, it is also necessary to provide a mechanical or physical means of immediately mixing the samples with the composition at the point of collection. Rapid homogenization and complete disruption of freshly collected biological sample in the present composition ensures the stabilization of a representative snap-shot of total DNA profiles in the sample for prolonged periods of time at ambient temperature. As illustrated in the Examples below, if the present composition is added to a collected solid feces sample, but not adequately mixed, the quality of the DNA is compromised relative to those samples that are mixed to homogeneity. Proper mixing of the samples is therefore crucial in order to stabilize the DNA such that it is representative of the in vivo (T=0) state. For instance, DNA extracted from such samples, followed by agarose gel electrophoresis, may show degradation of high molecular weight DNA in samples from some donors. Also, as seen in the Examples below, inadequate mixing of feces samples from some donors leads to detrimental changes to the microbiome profile, as measured with bacterial 16S rRNA PCR and DGGE analysis.

In many instances, biological sample collection, in particular feces collection, is best done by donors in the privacy of their own home. In this setting, the donor is more comfortable, and if provided instruction and an appropriate biological sample collection device or kit containing a stabilization chemistry or solution, the donor can immediately collect and stabilize fresh biological samples. Collecting samples in this manner helps ensure the best quality nucleic acid for subsequent extraction and analysis, with DNA profiles matching as close as possible the in vivo state. However, in order to collect and stabilize a biological sample at home or remote field collection site, the donor must be provided a simple, safe and intuitive, but highly effective, means to manually or physically mix their collected sample with stabilizing solution themselves. Preferably, this mixing means is inexpensive and requires no electricity, equipment or specialized training.

DNA can rapidly degrade in biological samples (e.g. feces) upon exposure to air, if not mixed with a stabilization solution, or when not immediately frozen on dry ice at the point of collection. With homogenous, liquid biological samples, such as blood and urine, mixing is not a significant issue; however, disruption of solid and semi-solid, non-homogeneous biological samples, such as feces, in a limited amount of solution and time can be exceedingly problematic. Through much experimentation with numerous mixing means (e.g. glass/silica particles 1 mm; 2.65 g/cm3), glass/silica beads (2-4 mm; 2.65 g/cm3), marbles (12.7 mm), alumina oxide balls (7.9 mm; 3.95 g/cm3), and silicon nitride balls (7.1-7.9 mm; 3.21 g/cm3), the inventors discovered that complete disruption and homogenization of all feces samples types (1-7 on the Bristol Stool scale), collected in standard, commercially-available laboratory or transport tubes (e.g. 10 mL round-bottom tube (92×15.3 mm), Cat. No. 60.610; Sarstedt) containing the present composition, can be attained by simple hand mixing with the inclusion in the tube of at least one large (5.6-11.1 mm, preferably 7.9 mm) dense (7.6-15.63 g/cm3) metal ball sized smaller than the inner diameter of the tube (e.g. 12.9 mm).

The inventors determined the optimal selection of a homogenization means for a standard, commercially-available laboratory tube, includes: 1) matching the shape of the tube (e.g. bottom or base inside the tube) with the shape of the homogenization means (e.g. round-bottom tube for a homogenization means that is at least one mixing ball, such as a stainless steel mixing ball) to prevent compaction and/or entrapment of solid material in hard to reach areas of the tube or container; 2) selection of the most dense material possible for the homogenization means (e.g. tungsten carbide (15.63 g/cm3), stainless steel (7.6-8.0 g/cm3); 3) selection of a homogenization means with an outside diameter slightly smaller than the internal diameter of the tube or container (for example, when the homogenization means is a mixing ball, the mixing ball would have a diameter of about 4-6 mm, preferably about 4-5 mm, and most preferably about 5 mm less than the internal diameter of the mixing tube); and 4) selection of a tube or container with 'headspace' above the sample and stabilizing solution to allow the homogenization means to gain momentum during shaking by hand. It should be noted that the mixing ball can be of regular or irregular shape (e.g. could have nubs, spikes, etc. and need not be perfectly spherical), and as noted above preferably has a density of at least 5.0 g/cm3, most preferably at least 7.6 g/cm3.

Should the homogenization means/ball be too small with respect to the tube, sample passes around the homogenization means/ball without being dispersed in the stabilizing solution. In contrast, should the homogenization means/ball be too large (e.g., >11.1 mm) with respect to the tube (12.9 mm internal diameter), sample is not dispersed or 'crushed' between the homogenization means/ball and the walls of the tube, the homogenization means/ball does not gain sufficient momentum, and sample becomes compacted at one or both ends of the tube. Ideally, when the outside diameter of the homogenization means (e.g. 7.9 mm tungsten carbide or stainless steel ball) just clears the inner vertical walls of the tube (e.g. 10 mL Sarstedt tube having internal diameter of 12.9 mm, above) by about 5 mm (2.5 mm on either side of the ball), the homogenization means effectively functions as a homogenizer, rapidly breaking down or disrupting solid and semi-solid feces sample (e.g. 400 mg; type 1-7), collected into the present composition (e.g. 2 mL), to form a homogeneous liquid sample which can be readily pipetted or manipulated and processed in the laboratory. This homogenization means ensures the collected biological sample, even solid feces, is rapidly and completely disrupted, and, in doing so, quickly exposed to the present composition. Importantly, the inventors determined that the density of the homogenization means, not just its diameter, compared to the tube/container, was critical for achieving complete disruption of the sample in a timely manner (20-30 seconds) simply with shaking the tube by hand. Due to the often sticky, malleable nature of feces (e.g. type 4), complete homogenization of this sample was difficult to achieve in flat-bottomed or conical-bottomed tubes when utilizing a spherical homogenization means. Hence, a round-bottomed tube for a spherical homogenization means performed the best.

The present invention provides a novel, universally-applicable method and composition for stabilizing total DNA in particularly complex, non-homogeneous biological samples at ambient temperature for subsequent use in human and animal medical diagnostics and clinical research (e.g. diagnosis of disease and infection, role of microbes in human health, population genomics to study microorganism evolution, virulence, drug-resistance, and epidemiology), food safety (food/meat processing plants), soil and waste water sampling (environment testing), biosecurity or biodefence (biological weapons), animal feed testing, plant and animal science/industry, etc.). A new and rapidly expanding focus of both researchers and clinicians is the intestinal microbiota or gut microbiome. How does the profile of microbes in feces from healthy donors differ from that of diseased individuals? Can manipulation of the human gut microbiome benefit health? For research, environmental, and economic reasons, there is also immense interest in the analysis of the thousands of different microorganisms in the rumen of many livestock, especially those animals which are reared for meat and dairy products.

The present invention simplifies and expedites biological sample collection and preparation, providing quality samples for the subsequent detection of human, animal and microbial DNA, without the need to maintain the cold-chain during transport or storage. The invention can be used in a) central laboratories or testing facilities with high-throughput or automated systems, b) rural or mobile clinics with minimal laboratory infrastructure and equipment, and c) remote locations with no electricity. In addition, sick and potentially infectious individuals do not have to travel to clinics or hospitals to provide a biological sample, minimizing the spread of infectious disease, facilitating outbreak control and surveillance, and enabling rapid assessment and monitoring of a patient's response to treatment.

The closed collection and homogenization system/kit as herein described is inexpensive to manufacture and no additional laboratory equipment (e.g. vortex) need be purchased. Most importantly, manual shaking of the capped tube containing the present composition, one or more homogenization balls, and even hard feces (type 1-2, Bristol Stool scale) sample, can achieve complete disruption of the sample in seconds, resulting in a homogeneous mixture. Donor self-collection reduces the spread of infection and potential cross-contamination with other donor's samples. Notably, this sample collection and homogenization process can be performed by the lay person, having no laboratory or clinical experience, in the privacy of their own home, greatly improving donor participation and compliance. Important for the quality of downstream test results, the present invention allows the safe collection and stabilization of "fresh" biological samples, drastically reducing the degradation observed during the transit of raw or untreated biological samples to testing facilities and/or variable storage conditions.

Critically, the present invention will provide researchers and clinicians with desperately needed stabilized, representative biological samples from which unbiased DNA can be extracted. Unbiased DNA input, i.e., a representative snapshot of the gut microbiome at point of sample collection, will enhance the quality and accuracy of downstream analyses, enable more accurate comparative assessments of inter- and intra-subject differences, as well as inter-study differences, for studying variations in human intestinal microbial communities, in health and disease. Intact, unbiased, rich high molecular weight DNA is critical for metagenomic library construction and the characterization of intact genetic pathways either by sequence-based or functional screening-based approaches. In addition, excessive degradation of DNA in biological samples reduces the efficiency of shotgun sequencing.

Only in the last few years has significant attention been paid to the phylogenetic composition of DNA extracted from feces, in relation to the bacterial community in fresh feces. It is common practice, mainly for practical reasons, to freeze feces samples after collection and, after a highly variable period of time, extract DNA for downstream analysis, such as sequencing or quantitative PCR (qPCR). Critically, however, between and within published studies there appears to be considerable variability in: 1) the period of time between defecation and freezing of 'fresh' feces; 2) transport conditions and duration; 3) length of time feces was frozen before analysis; 4) length of time and temperature employed to thaw frozen feces; and 5) variable time from collection before the first aliquot is isolated and processed for DNA. In these studies, T=0 represents the moment these collected, frozen, and often stored, samples have been thawed for processing, not the time of defecation.

In metagenomic studies of the human microbiota, however, studies have clearly shown that storage conditions of feces samples may adversely affect the inferred community composition. For example, Bahl et al. (2012), demonstrated using qPCR and 6 different primer pairs targeting 16S rRNA genes of significant bacterial groups, that freezing feces samples at −20° C. for 53±5 days prior to extraction affected the ratio between the two most predominant phyla, namely the Firmicutes and the Bacteroidetes, a frequently used biomarker in gut microbiology. Specifically, the Firmicutes to Bacteroidetes 16S rRNA gene ratio was significantly higher in fecal samples that had been frozen, compared to identical samples that had not. Desperately needed is a means to capture or snap-shot at least three key aspects of the original or in vivo microbial community in collected feces samples, stabilizing i) the abundance of each microbe, ii) the richness of the entire community, and iii) total microbial DNA profiles.

Efficient and nonbiased stabilization (and extraction) of total genomic bacterial DNA from complex fecal samples is a crucial first step for molecular-based studies of the bacterial community within the gut, e.g. generating microbiome profiles that represent the in vivo state of the donor. In particular, the study of the microbial communities requires capturing a "snapshot" of the microbiota profile immediately after collection. It is clear current field collection of fecal samples is impractical, expensive and not scalable (McInnes & Cutting, 2010). It is also well known in the field that problems related with sample collection cause inconsistent results and low reproducibility. Furthermore, handling of solid samples poses a challenge for automation, increasing the cost and limiting the size of longitudinal studies.

To eliminate strong biases between and within studies across laboratories, there is a need to develop and implement a standardized or universal method for the collection and stabilization of biological samples at the point of collection, prior to being subjected to unfavourable, often extreme temperatures during transport and prolonged storage. The present method of homogenizing biological samples, in particular, highly variable in type, complex, non-homogeneous samples, ranging from liquids to hard solids, in an effective DNA-stabilizing composition at the point of sample collection, ensures the maximal integrity of DNA in the entire sample, representing as close as possible the in vivo state.

Presently, many studies recruit donors to collect feces samples and provide either no stabilizing means or require the use of ice packs during transport. The Human Microbiome Project (HMP), a program initiated under the National Institutes of Health (NIH) Roadmap, sponsors studies to characterize the human microbiome and analyze its role in human health and disease. All members participating in the HMP Core Microbiome Sampling study must follow the Manual of Procedures (McInnes & Cutting, 2010) outlining, among other things, specimen collection from the GI tract (see section 7.3.3). Subjects are provided a feces collection kit and required to collect feces specimens within a 24-hour period before bringing the specimens back to the clinic. HMP kits include two feces collection containers (one is for back-up) resembling large margarine tubs, a Thermosafe shipping container (a large Styrofoam box inside a cardboard box), 8-10 polar packs for transport of specimen (at about 4° C.), instructions, labels, and other packing materials. Before collecting a specimen, subjects must place the gel packs in their freezer for at least 12 hours. Feces is deposited directly into the collection container, the lid is applied, and the entire container is sealed in a Ziplock bag, prior to packaging in the Styrofoam box, completely surrounded by 8-10 frozen gel packs. The Styrofoam box is closed, sealed inside a cardboard box, and the subject transports this bulky package to the clinical lab.

The existing cold-chain requirements to ship fresh specimens packed on ice or dry ice, sealed in bulky Styrofoam and cardboard containers/coolers, is very costly, even prohibitive for researchers conducting studies requiring moderate to large numbers of donors. Simply, the shipment of a commercially-available feces collection container, surrounded by frozen ice packs, in a Styrofoam container, within a cardboard shipping box or over-pack (16×13×14 inches), costs approximately $175 each using UPS Next Day delivery service within the United States. This estimate does not take into account the cost of the feces collection container and any shipping materials. Also, many testing facilities require biological samples be shipped on dry ice which adds considerable cost to this shipping estimate. Once the lab receives these large shipping containers, staff must immediately unpack and quickly process the biological samples or place the collection containers into large storage freezers until batch processing can be performed. In contrast, the present invention alleviates most of the current shipping cost and inconvenience, and, most importantly, ensures the DNA in collected biological samples is stabilized at the point of collection at ambient temperature. From the donor's perspective, the biological sample is collected in the privacy of their home, a small portion of the specimen is transferred to a familiar tube or container already containing stabilization solution, a cap is applied to the tube and shaken by hand to mix, the tube is sealed in a biohazard bag, and mailed to the testing facility in a bubble envelope or small box at a fraction of current costs.

EXAMPLES

Materials and Methods

The following general materials and methods are used in the Examples that follow, except where different conditions are specified therein.

Collection of Feces Samples

Healthy donors were each given the following supplies for a collection: a) a feces collection container (sits on the toilet); b) a syringe for volumetric feces collection of about 400 mg (i.e. 3 mL syringe with tip cut off, plunger adjusted to 400 mg collection volume); c) a round-bottom Sarstedt tube (10 mL round-bottom tube (92×15.3 mm), Cat. No. 60.610; Sarstedt) containing the present composition (2 mL), and various homogenization means (e.g. 7.9 mm stainless steel ball bearing, 420/440 SS Grade 25, Aimark Travers LTD, or others as noted below); and d) feces collection instructions. Tubes were weighed pre- and post-collection to determine the actual amount of feces sample collected. Each donor was asked to fill the tip of the syringe with feces to the marked volume (400 mg) and transfer the feces sample to tube. For complete homogenization of samples, tubes were shaken by hand for 20-30 seconds.

DNA Extraction from Feces Samples in the Present Composition

Unless stated otherwise, 400 mg feces was transferred to a Sarstedt tube (10 mL round-bottom tube (92×15.3 mm), Cat. No. 60.610; Sarstedt) containing 2 mL of the present composition (specified in Examples below) and a 7.9 mm stainless steel ball bearing. DNA was readily extracted from 250 μL aliquots of feces samples collected and stored in the present composition utilizing several commercially-available DNA isolation kits. Feces samples in the present compositions were found to be compatible with POWERSOIL® DNA Isolation Kit (MO BIO Laboratories, Inc., Cat. No. 12888-100), POWERFECAL® DNA Isolation Kit (MO BIO Laboratories, Inc., Cat. No. 12830-50), Zymo Research Fecal DNA MiniPrep incorporating bead-beating (Zymo Research, Cat. No. D6010), QIAamp DNA Feces Mini Kit (Qiagen, Cat. No. 51504) and PSP Spin Feces DNA Plus Kit (Invitek, Cat. No. 1038110200).

As per POWERFECAL® DNA Isolation Kit Instructions, the following procedure was followed [Note: 65° C. heating step was eliminated]:

1. To the POWERBEAD™ tube provided, 750 μL of bead solution and 250 μL of feces sample in present composition were added. The tube was gently vortexed to mix.
2. 60 μL of Solution C1 was added and the tube was inverted several times or vortexed briefly.
3. POWERBEAD™ tube was secured on the vortex adapter and vortexed for 10 minutes at maximum speed.
4. POWERBEAD™ tube was centrifuged at 10,000×g for 30 seconds.
5. The supernatant was transferred to a clean 2 mL collection tube (provided).
6. 250 μL of Solution C2 was added and the tube was vortexed for 5 seconds, then incubated at 4° C. for 5 minutes.
7. The collection tube was centrifuged at room temperature for 1 minute at 13,000×g.
8. Avoiding the pellet, up to, but no more than, 600 μL of supernatant was transferred to a clean 2 mL tube.
9. 200 μL of Solution C3 was added and the tube was vortexed briefly, then incubated at 4° C. for 5 minutes.
10. The tube was centrifuged at room temperature for 1 minute at 13,000×g.
11. Avoiding the pellet, up to, but no more than, 750 μL of supernatant was transferred into a clean 2 mL tube.
12. Solution C4 was mixed before use. 1200 μL of Solution C4 was added to the supernatant and the tube was vortexed for 5 seconds.
13. 675 μL was loaded onto a Spin Filter and centrifuged at 13,000×g for 1 minute. The flow through was discarded and an additional 675 μL of supernatant was added to the Spin Filter and centrifuged at 13,000×g for 1 minute. The remaining supernatant was loaded onto the Spin Filter and centrifuged at 13,000×g for 1 minute.
14. 500 μL of Solution C5 was added onto the Spin Filter and centrifuged at room temperature for 30 seconds at 13,000×g. The flow through was discarded.
15. Centrifuging was carried out again at room temperature for 1 minute at 13,000×g.
16. The spin filter was carefully placed in a clean 2 mL collection tube (provided).
17. 100 μL of Solution C6 was added to the center of the white filter membrane.
18. The tube was centrifuged at room temperature for 30 seconds at 13,000×g.
19. DNA was stored frozen (−20 to −80° C.).

Determination of DNA Concentration in Purified Samples

A. Absorbance Determination of DNA Concentration

Measurement of absorbance at 260 nm (A260 nm) is commonly used for quantifying DNA. An absorbance of 1.0 at 260 nm corresponds to a concentration of 50 ng/μL for pure double-stranded DNA. DNA yields from purified feces samples, treated with or without the present compositions under various conditions, were determined using a NanoDrop 2000c spectrophotometer (Thermo Fisher Scientific Inc.). A 2 μL volume of each DNA sample was placed on the pedestal and scanned from 220 nm to 350 nm with absorbencies measured at 230 nm, 260 nm and 280 nm. Sample DNA concentration (ng/μL), A260/A280 ratio, and A260/A230 ratio were reported by the NanoDrop 2000c software. The total DNA yield per sample was calculated by multiplying the sample concentration by the respective DNA elution volume.

B. Fluorometric Determination of DNA Concentration

Disadvantages of using A260 nm include (i) insensitivity of the assay and (ii) interference by non-DNA components, such as RNA, particularly in samples that are not highly purified.

DNA yields from purified samples were also quantified using PICOGREEN® Fluorescent dye (200×; Invitrogen, Cat. No. P7581); Lambda DNA (Invitrogen, Cat. No. 25250-010) was used to generate a standard curve [in triplicate; 0-50 ng/4]. PICOGREEN® is a fluorescent double-stranded DNA-binding dye (485 nm Excitation/535 nm Emission) that enables sensitive quantitation of sub-nanogram amounts of double-stranded DNA (dsDNA). Triplicate aliquots of each purified sample and Lambda DNA standards were processed in a black flat-bottomed 96 well microplate (Greiner Bio-One, Cat. No. 655209) and fluorescence was measured using an Infinite M200 microplate reader (TECAN).

Integrity of DNA in Samples Stored in Stabilizing Compositions

An aliquot of each purified sample was diluted to 10 ng/μL, based upon concentration determined by PICOGREEN® fluorescent dye (above). To assess DNA integrity, approximately 80 ng from each diluted, purified feces sample was separated on a 1% agarose gel by electrophoresis for 30 minutes at 100 volts. The gel was stained in 1 μg/mL ethidium bromide (EtBr) in distilled water for 15 minutes at room temperature, rinsed and photographed on a UV transilluminator using a DIGIDOC-IT® imaging system (UVP LLC). DNA was determined to be stabilized and intact when the stained band on the gel was sharp and >23 Kb, compared to the DNA ladder. 1 Kb+ DNA Ladder (Life Technologies, Cat. No. 10787-018) or Lambda DNA/Hind III fragments (Life Technologies, Cat. No. 15612-013) were used as size references.

a. 1% agarose gel was prepared (80 mL 1×TAC+0.8 g agarose).
b. 2 μL of 5× loading buffer was added to 8 μL of 10 ng/μL of purified sample.
c. Into wells of a prepared 1% agarose gel was loaded 10 μL prepared sample (step b); 5 μL Lambda DNA/Hind III fragments and/or 5 μL 1 Kb DNA ladder.
d. Gel was run at 100 V for 30 minutes.
e. Gel was stained in EtBr (500 μL 1 mg/mL EtBr+500 mL water) for 15 minutes.
f. Gel was destained in water for 5 minutes.
g. Images were taken under UV.

Denaturing Gradient Gel Electrophoresis (DGGE)

To accurately and reproducibly evaluate the stability of various microbiomes (feces, saliva, sputum, skin, etc.) in the present composition, a new method called Denaturing Gradient Gel Electrophoresis (DGGE) was utilized. This method is based on the idea that if one takes a variable region of the bacterial 16S rRNA gene (in this case the V3 region) and amplifies it using PCR and primers on the flanking conserved region, that amplicons will have a melting point unique to the species of bacteria (even nucleotide differences will affect the melt and thus give a different profile).

When this method is applied to a sample containing multiple species of bacteria, the amplification using conserved primers will result in an array of amplicons, all of which are roughly the same length, but have a different nucleotide make-up in the non-conserved area. Next, these amplicons are run on a gel which contains a gradient of denaturing solution (urea and formamide). The amplicons will denature at different stages on the gel, depending on their nucleotide make-up, thus giving a resolution of all the species that were present in the sample.

In order for the DNA amplicons to not denature to single-stranded form, a ~30 nucleotide CG clamp was added to the forward primer which retards the migration of the amplicons on the gel once the variable section has denatured. In general, a 40%-60% denaturing gradient on the gel provides good resolution of the bands, while capturing most of the gut species. The gel is run at a constant 60° C. in order to facilitate denaturing of the amplicons and also keep the gel at equal temperature throughout the run.

DGGE gel images were analyzed using the Syngene GeneTools software (version 4.03.00, Syngene). The image background was subtracted using rolling disc method with a radius of 30 pixels. Lanes were manually detected and set. Rf start and end location and angle was set to manual to adjust for "smiling" in the gel. Bands for analysis were automatically detected for each lane; peak detection was set under default (minimum width of 7 pixels, minimum peak height of 3, and minimum peak volume of 1%). The profiles were matched using the "profile" type under the matching parameters menu with a set tolerance of 1%. Profile comparison resulted in an automatically generated similarity matrix, with similarity values ranging from 0 to 100. Generally speaking, for % similarity, this refers to any changes between 2 profiles, usually differences in band intensities. Thus, % similarity provides a measure of the difference in abundance of species. When a band is absent between profiles, the impact on % similarity is higher than when that band is just decreased in intensity.

The DGGE gel shown in FIG. 1 illustrates how different the microbiome profile of feces samples from two different donors can appear; only 22% similarity exists between the first feces sample (Donor A) and the second (Donor B) sample.

PCR-DGGE was carried out according to the procedure described below.

PCR Amplification for DGGE (using 16S Primers with 5'clamp on forward primer)
  a. 2 µL of 10 ng/µL DNA was added into 12-strip PCR tubes.
  b. Master Mix was prepared (98 µL/reaction): 76.7 µL water, 10 µL 10×PCR Buffer, 4 µL 50 mM MgCl2, 2.5 µL 10 mM dNTPs, 2 µL 10 pmol Rev Primer (PPUN518R, 5'-ATTACCGCGGCTGCTGG-3', SEQ. ID NO. 1), 2 µL 10 pmol Fwd Primer (PRBA338F, 5'-CGCCCGCGCGCGGCGGGCGGGGCGGGGGC ACGGGGGGACTCCTAC GGGAGGCAGCAG-3', SEQ. ID NO. 2), and 0.8 µL 5 U/µL Taq.
  c. 98 µL master mix was added to each tube.
  d. PCR was run on conventional PCR machine: 1 cycle at 92° C. for 2 minutes; 28 cycles at 92° C. for 60 seconds, 55° C. for 30 seconds, 72° C. for 60 seconds; followed by 1 cycle at 72° C. for 6 minutes.

DGGE of PCR Amplicons
  a. Stock solutions were prepared for an 8% Acrylamide/Bis gel in 40% and 60% denaturing solutions:

|  | 40% | 60% |
| --- | --- | --- |
| 40% Acrylamide/Bis | 20 mL | 20 mL |
| 50x TAE Buffer | 2 mL | 2 mL |
| Formamide (deionized) | 16 mL | 24 mL |
| Urea | 16.8 g | 25.2 g |
| ddH$_2$O | Up to 100 mL | Up to 100 mL | b. The glass plates and spacers were assembled according to the instruction booklet for the DCode system (Bio-Rad).
  c. To prepare and pour an 8% Acrylamide/Bis gel with a parallel gradient using 40% and 60% denaturing solutions, the following procedure was used:
    20 mL of 40% and 60% denaturing solutions were measured into 2 separate beakers labeled "low density" and "high density," respectively;
    200 µL of 10% ammonium persulfate (APS) was added to each solution;
    20 µL of TEMED was added to each solution;
    The solutions were mixed well by swirling;
    Each solution was filled into a separate 20 mL syringe;
    The syringes were attached to the gel loading apparatus where specified "low density" or "high density" for top filling;
    Note: The volume adjustment settings for a 16×16 cm gel with 1.0 mm spacers was 18.5 mL;
    The Y tubing was attached to each of the syringes, with a needle on the other end of the tubing;
    The needle was placed between the glass plates;
    The gel was poured slowly and consistently by turning the wheel so that the gradient had time to even out;
    The gel was allowed to polymerize for a few hours;
    The Y tubing was flushed out with water.
  d. The gel running system was pre-heated with 1×TAE buffer to 55° C.
  e. 8 µL of Fermentas 6× loading dye was added to 42 µL of PCR product.
  f. The gel was run for 5 minutes at 200 V before turning on the recirculation pump in order to get the samples out of the wells and into the gel.
  g. The gel was run for 14 hours at 70 V with the recirculation pump on.
  h. The gel was stained in 1× Sybr Gold for 30 minutes (250 mL 1×TAE+25 µL 10,000× SybrGold).
  i. The gel was destained in 1×TAE for 5 minutes.
  j. Images were taken under UV.

16S rRNA PCR was performed using universal primers (V3 region) followed by DGGE using the DCode Universal Mutation Detection System (Bio-Rad).

16S rRNA Sequencing 16S rRNA sequencing library preparation, sequencing and bioinformatics were conducted. V4 hypervariable region paired-end amplicon sequencing was performed using the ILLUMINA® MISEQ® (250 cycles). Using QIIME and custom scripts, sequences were quality filtered. Paired-end reads were assembled and searched against the Greengenes reference database, clustered at 97% by UCLUST. After data normalization, sample-to-sample distance was measured using Weighted Unifrac on OTU (operational taxonomic units) abundance data (utilizes taxon abundance differences across samples, employing a pair-wise normalization by dividing the sum of differences by the sum of all abundances) and unweighted Unifrac incidence data (considers only the presence/absence of taxa).

Amplification of Human DNA from Purified Feces Samples Stored in the Present Composition The stability of human DNA in feces samples collected into the present composition (detailed below) and stored at room temperature for 2 weeks, prior to total DNA extraction (POWERSOIL® or POWERFECAL® DNA Isolation Kit of MO BIO Laboratories), was evaluated in real-time or quantitative PCR (qPCR) using primers targeting the single copy human thymidylate synthase gene (TYMS locus; NM001071.2). For each reaction, 50 ng of purified DNA was amplified in a 25 µL volume containing: 1×PCR Buffer (20 mM Tris, 50 mM KCl), 2 mM MgCl2, 200 µM dNTPs (Invitrogen), 50 µg/mL BSA (Sigma Aldrich), 1 µM SYTO9 dye (Invitrogen), 0.4 µM each of Primer hTSm143F (5'-GCCCTCTGCCAGTTCTA-3', SEQ. ID NO. 3) and hTSm143R (5'-TTCAGGCCCGTGATGT-3', SEQ. ID NO. 4; Invitrogen), 1 U Taq polymerase (Invitrogen). The amplification conditions for the TS143 target were: 1 cycle at 95° C. for 5 minutes; 35 cycles at 95° C. for 20 seconds, 55° C. for 20 seconds, 72° C. for 30 seconds; followed by 1 cycle at 72° C. for 10 minutes. A melt curve program was included and consisted of: 1 cycle at 95° C. for 30 seconds at a ramp rate of 4.4° C./second (no acquisition), 72° C. for 10 minutes at a ramp rate of 2.2° C./second (no acquisition), 95° C. at a ramp rate of 0.11° C./second (continuous acquisition). DNA samples were run in triplicate in a Corbett Rotorgene RG-6000 and Ct values for each sample calculated using the Rotorgene 6000 series software 1.7. The Ct value refers to the fractional cycle number at the point where the amplification curve crosses a threshold of detection. By setting a threshold line and calculating the intersection with each of the sample curves, the Ct values for each sample are established. The threshold line is set in the exponential phase of the run, significantly above the background level to avoid noise and below the onset of signal plateau in later cycles. Generally, the Ct value is inversely proportional to the amount of DNA in the sample. ΔCt, represents the difference in Ct values resulting from two aliquots taken from the same sample at different times, e.g., T=0 and T=14 days post sample collection.

Example 1—Comparison of Different Chelating Agents in Compositions for Stabilizing DNA in Fecal Samples Due to the vast amounts of nucleases in feces, mostly bacterial in origin, the inventors experimented with different chelating agents, and concentrations thereof, during development of the present composition.

The compositions described in the current Example contained 23.5% ethanol, 0.5% SDS, and 0.1% Antifoam A, along with EDTA or CDTA in varying amounts, buffered to pH 11 with 50 mM β-alanine. Percentages of ethanol and Antifoam A are (% v/v) in this and subsequent Examples, and percentages of other components (SDS, triclosan) are in (% w/v).

Figure 2:
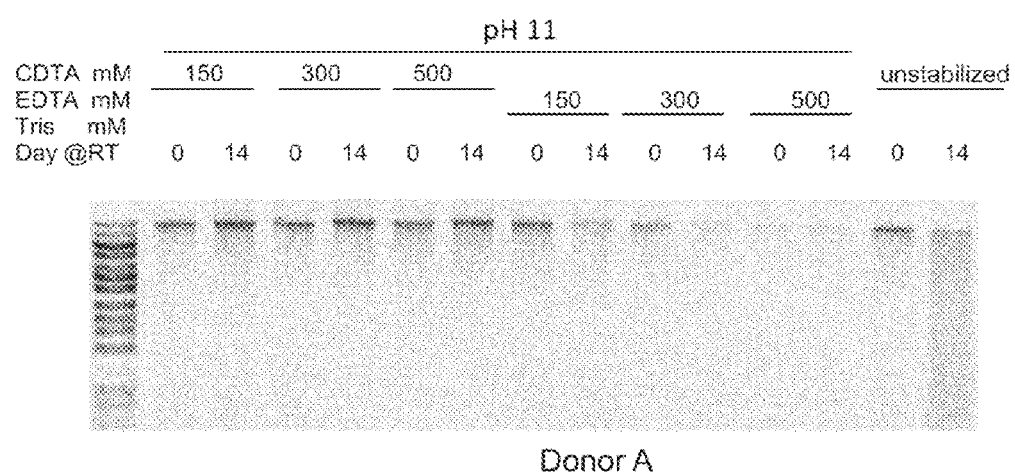
FIG. 2 shows an agarose gel demonstrating the quality of high molecular weight DNA in fecal samples at T=0 and following 14 days at room temperature in 1) compositions containing different concentrations of CDTA (150-500 mM), 2) compositions containing different concentrations of EDTA (150-500 mM), and 3) feces stored without stabilizing solution (unstabilized)

Referring to FIG. 2, feces was collected by a healthy donor and 400 mg samples were homogenized in various stabilization solutions or stored in the absence of stabilization buffer (unstabilized) for 14 days at room temperature (RT, 19-23° C.) prior to DNA extraction with a commercially-available kit (POWERSOIL® or POWERFECAL® DNA Isolation Kit of MO BIO Laboratories). Comparing the quality or integrity of purified DNA at T=0 and T=14 days, the agarose gel clearly shows that high molecular weight DNA in untreated feces degrades significantly during storage at RT (control, last 2 lanes of agarose gel), forming a smear on the gel. Samples (400 mg) from the same donor's feces were also homogenized in: 1) the present composition, including increasing amounts of CDTA (150, 300, 500 mM); and 2) the present composition in which CDTA was replaced with EDTA (150, 300, 500 mM).

Surprisingly, at all concentrations tested (150, 300, 500 mM) with fecal samples, CDTA performed significantly better than EDTA for stabilizing high molecular weight DNA in both freshly collected samples (T=0) and after RT exposure for 14 days (FIG. 2). In fact, EDTA, but not CDTA, was unexpectedly detrimental to stabilization (and extraction) of high molecular weight DNA at concentrations over 150 mM.

In addition, a comparison of higher concentrations (150, 300 and 500 mM) of EDTA and CDTA (Table 4), supports the surprising discovery that CDTA is superior to EDTA for stabilizing microbiome profiles, as exemplified via PCR of bacterial 16S rRNA gene and DGGE analysis of the amplicons, as described in the Materials and Methods section above. Following 14 and 30 days at RT, DNA from fecal samples stored in the present composition with CDTA maintained high percent similarities to control samples processed at T=0. In contract, the microbiome profile of DNA from the same feces stored in the present composition substituted with EDTA showed increasing dissimilarity with time at RT, compared to controls samples (processed at T=0; Table 4).

TABLE 4

Microbiome stability of feces stored in compositions with increasing concentrations of chelating agents.

| | Days at room temperature | | | Days at room temperature | |
| --- | --- | --- | --- | --- | --- |
| | 14 | 30 | | 14 | 30 |
| | % similarity in microbiome profile compared to T = 0 | | | % similarity in microbiome profile compared to T = 0 | |
| [EDTA] | control | | [CDTA] | control | |
| 0 | 81 | 57 | 0 | 81 | 57 |
| 150 | 86 | 79 | 150 | 94 | 86 |
| 300 | 89 | 74 | 300 | 93 | 84 |
| 500 | 86 | 62 | 500 | 95 | 88 |

Hence, CDTA surprisingly out performed EDTA in its ability to stabilize intact, high quality, high molecular weight DNA and snap shot the microbiome profile in complex, non-homogenous feces. Thus, chelators such as CDTA, with a dissociation constant higher than EDTA, provide the best stabilization of DNA in biological samples, such as fecal samples, and are particularly preferred for use in the compositions described herein. This ability to stabilize samples at the point of sample collection will help eliminate strong biases currently seen between and within studies across laboratories.

Example 2—Role of pH and Chelating Agents in Fecal Sample Stability in the Present Composition The complex relationships between fecal sample mixing, pH, and chelating agent concentration were investigated for their effects on microbiome profile stability as exemplified via PCR of bacterial 16S rRNA gene and DGGE analysis of the amplicons.

In the first of four experiments, a healthy donor collected feces and transferred 400 mg of feces into four tubes each containing a single 7.9 mm stainless steel ball and 2 mL of either composition "104B pH 9.5" (300 mM CDTA, 23.5% ethanol, 0.5% SDS, 0.1% Antifoam A, pH 9.5) or "104B pH 11" (300 mM CDTA, 50 mM β-alanine, 23.5% ethanol, 0.5% SDS, 0.1% Antifoam A, pH 11). Samples in the tubes were left undisturbed (no mix) or homogenized with hand shaking (mix) and then returned to the lab under ambient temperature conditions. Within 3-4 hours of sample collection, a 250 µL aliquot was removed from each tube for DNA extraction (T=0) and then samples were stressed by storing at 30° C. for 24 hours, followed by −20° C. for 11 days (T=11), prior to DNA extraction from a second aliquot. Purified DNA was quantified and then resolved as bacterial community profiles or fingerprints using DGGE to separate 16S rRNA gene PCR amplicons. Percent similarity between samples (lanes on DGGE gel), compared to the control sample at T=0 for each composition, was calculated separately using Syngene GeneTools software (see Materials and Methods).

Figure 3:
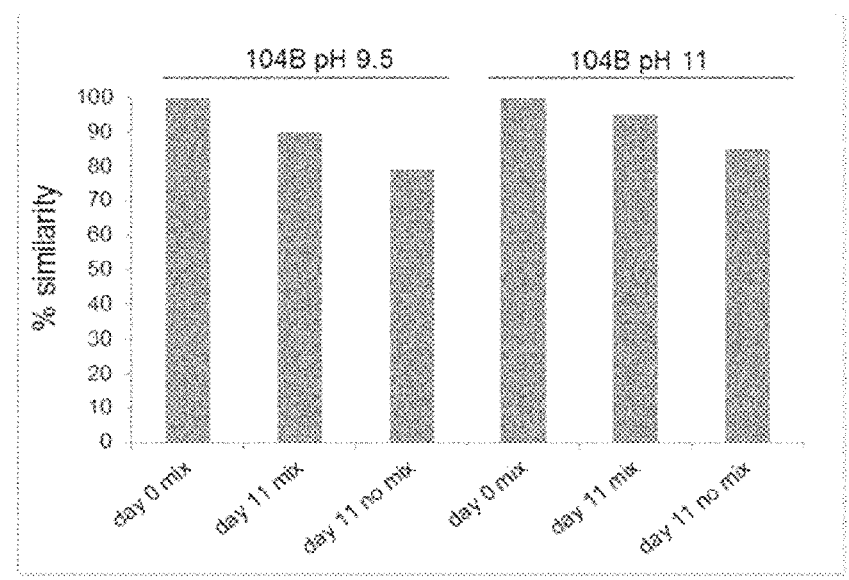
FIG. 3 graphically depicts the dependence of microbiome profile stability on sample homogenization and pH of the present composition.

FIG. 3 illustrates improved percent similarities or microbiome profile stability between the '11 day no mix' samples and 'day 0 mix' samples when the pH of the present composition is increased from 9.5 to 11, indicating that pH 11 offers additional DNA stability than pH 9.5. Also, 'day 11 mix' samples, in tubes using the present homogenization means, a dense steel ball, consistently led to improved microbiome profile stability compared to 'day 11 no mix' samples, at both pH values tested, and, in particular, at pH 11.

In a second experiment, the relationship between pH and the concentration of CDTA was addressed. Aliquots (400 mg) from the feces of a healthy donor was transferred into tubes containing a 7.9 mm stainless steel metal ball and 2 mL of one of three compositions: 1) 104B pH 9.5 (as above); 2) 50 mM CDTA, 50 mM β-alanine, 23.5% ethanol, 0.5% SDS, 0.2% Triclosan, 0.1% Antifoam A, pH 11.5; and 3) 50 mM CDTA, 23.5% ethanol, 0.5% SDS, 0.2% Triclosan, 0.1% Antifoam A, pH 9.5. Samples were homogenized by hand mixing and returned to the lab under ambient temperature conditions where a T=0 aliquot (250 µL) was collected and DNA extracted. Remainder of the samples were stored at room temperature for 4 and 14 days, with aliquots removed and DNA extracted at each time point.

Agarose gel electrophoresis revealed that the 300 mM CDTA composition at pH 9.5 (104B pH 9.5) stabilized high molecular weight DNA for at least 14 days, and exhibited superior stabilization of high molecular weight DNA than did the other two compositions containing 50 mM CDTA composition at either pH 9.5 or 11.5 (data not shown). However, the presence of intact, high molecular weight DNA does not reliably indicate that a snap-shot of the microbiome was achieved. In the absence of an effective stabilization solution, bacterial species can replicate or die off, without altering the total amount of DNA, as well as its quality. The microbiome profiles of the samples were therefore examined via PCR of bacterial 16S rRNA gene and DGGE analysis of the amplicons, as described in the Materials and Methods section above.

Figure 4:
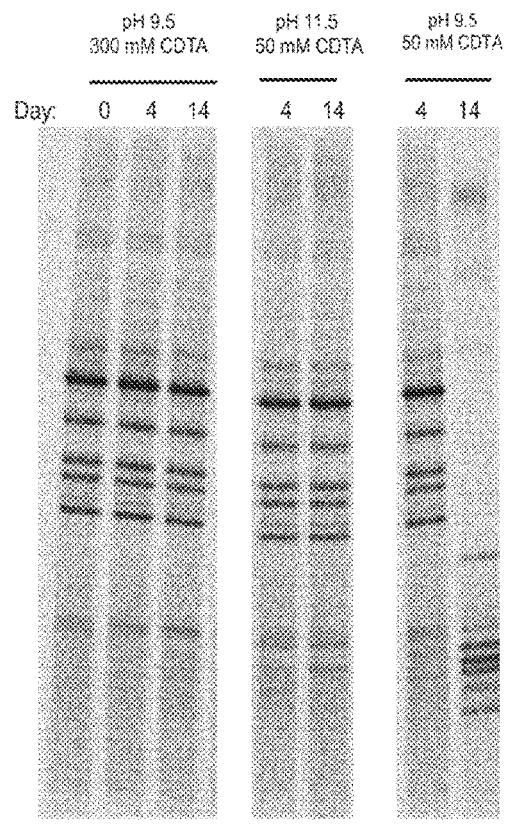
FIG. 4 shows DGGE analysis of fecal samples stored in various compositions for 14 days at room temperature.

Referring to FIG. 4 and Table 5, DGGE analysis revealed that the 300 mM CDTA composition at pH 9.5 exhibited excellent stabilization of the microbiome profile (94-96% similarity compared to t=0 control) for at least 14 days at room temperature. The effectiveness of the 300 mM CDTA composition at pH 9.5 at stabilizing the microbiome profile was surprisingly superior to that of the 50 mM CDTA composition at pH 9.5, which exhibited only 15% similarity compared to t=0 control after 14 days at room temperature. The pH 11.5 composition with 50 mM CDTA seemed to 'rescue' somewhat the considerable degradation of DNA per the microbiome profile seen in pH 9.5 composition with 50 mM CDTA.

Hence, a combination of high concentration of CDTA and considerably alkaline pH is required to stabilize the microbiome profile of fecal samples.

TABLE 5

Microbiome profile analysis of fecal samples stored in various compositions for 14 days at room temperature.

| Test Composition [All compositions below also contained 23.5% ethanol, 0.5% SDS, 0.2% Triclosan and 0.1% Antifoam A] | Days at Room Temperature | % similarity compared to *pH 9.5, 300 mM CDTA at day 0 |
|---|---|---|
| *pH 9.5, 300 mM CDTA | 0 | 100 |
| pH 9.5, 300 mM CDTA | 4 | 96 |
| pH 9.5, 300 mM CDTA | 14 | 94 |
| pH 11.5 (50 mM β-Alanine), 50 mM CDTA | 4 | 87 |
| pH 11.5 (50 mM β-Alanine), 50 mM CDTA | 14 | 78 |
| pH 9.5, 50 mM CDTA | 4 | 91 |
| pH 9.5, 50 mM CDTA | 14 | 15 |

In a third experiment, the relationship between pH and the concentration of CDTA in the present composition was addressed further. Aliquots (400 mg) from the feces of a healthy donor was transferred into tubes containing a 7.9 mm stainless steel metal ball and 2 mL of one of two compositions: 1) 300 mM CDTA, 23.5% ethanol, 0.5% SDS, 0.2% Triclosan, 0.1% Antifoam A, pH 9.5; and 2) 50 mM CDTA, 23.5% ethanol, 0.5% SDS, 0.2% Triclosan, 0.1% Antifoam A, pH 7.4. Samples were homogenized by hand mixing and returned to the lab under ambient conditions where a T=0 aliquot (250 µL) was collected and DNA extracted. Remainder of the samples were stored at room temperature for 4 days before a second aliquot was removed and processed.

Figure 5:
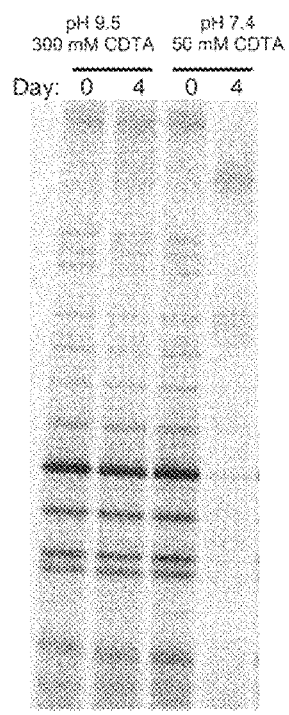
FIG. 5 shows DGGE analysis of fecal samples stored in different compositions for 4 days at room temperature.

Agarose gel electrophoresis revealed that 300 mM CDTA composition at pH 9.5 stabilized intact high molecular weight DNA in feces to a greater extent than did the 50 mM CDTA composition at pH 7.4 over 4 days at RT, and DGGE analysis indicated that this composition also exhibited superior stabilization of the fecal microbiome profile (97% similarity to T=0 versus 10% similarity to T=0, respectively—see FIG. 5 and Table 6). The microbiome profile stability of feces homogenized with the pH 7.4 composition (10% similarity to T=0 after 4 days at RT) was also considerably lower than the microbiome profile stability of feces homogenized with the 50 mM CDTA composition at pH 9.5 (91% similarity to T=0 after 4 days at RT, as noted above).

TABLE 6

Microbiome profile analysis of fecal samples stored in various compositions for 4 days at room temperature.

| Test Composition [All compositions below also contained 23.5% ethanol, 0.5% SDS, 0.2% Triclosan and 0.1% Antifoam A] | Days at Room Temperature | % similarity of sample compared to control sample do for each composition |
|---|---|---|
| pH 9.5, 300 mM CDTA | 0 | 100 |
| pH 9.5, 300 mM CDTA | 4 | 97 |

TABLE 6-continued

Microbiome profile analysis of fecal samples stored in various compositions for 4 days at room temperature.

| Test Composition [All compositions below also contained 23.5% ethanol, 0.5% SDS, 0.2% Triclosan and 0.1% Antifoam A] | Days at Room Temperature | % similarity of sample compared to control sample do for each composition |
|---|---|---|
| pH 7.4, 50 mM CDTA | 0 | 100 |
| pH 7.4, 50 mM CDTA | 4 | 10 |

In a fourth experiment, the relationship between pH at a fixed, high concentration of CDTA in the present composition was addressed. Aliquots (400 mg) from the feces of a healthy donor were transferred into tubes containing a 7.9 mm stainless steel metal ball and 2 mL of one of two compositions: 1) 300 mM CDTA, 23.5% ethanol, 0.5% SDS, 0.2% Triclosan, 0.1% Antifoam A, pH 7.4; and 2) 300 mM CDTA, 23.5% ethanol, 0.5% SDS, 0.2% Triclosan, 0.1% Antifoam A, pH 9.5. Samples were homogenized by hand mixing and returned to the lab under ambient conditions where a T=0, 24 hours, and 9 days an aliquot (250 µL) was collected and DNA extracted.

Figure 6:
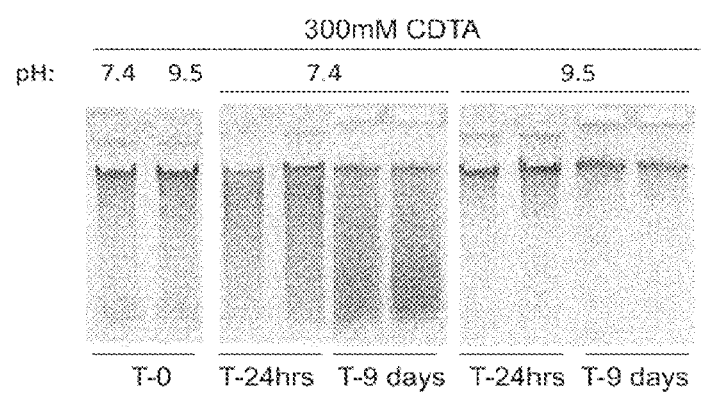
FIG. 6 shows an agarose gel demonstrating the quality of high molecular weight DNA in fecal samples stored in compositions at different pH values for 9 days at room temperature.

Agarose gel electrophoresis demonstrated that fecal samples mixed with a composition at pH 9.5 exhibit superior stabilization of high molecular weight DNA as compared to fecal samples mixed with a composition at near neutral pH conditions (pH 7.4), even in the presence of high (300 mM) concentrations of CDTA (see FIG. 6).

Taken together with the results shown in Example 1, these experiments indicate that optimal conditions for preserving intact, high molecular weight DNA and stable microbiome profiles during room temperature storage exist when the pH of the composition is greater than or equal to 9.5, preferably from about pH 10.5-11.5 or about pH 11, and the concentration of CDTA is greater than 50 mM, preferably at least about 150 mM, most preferably about 300 mM.

Example 3—Stabilization of Feces Following Mixing with Glass Beads and Stainless Steel Beads Feces from a healthy donor was transferred in 400 mg aliquots into four tubes containing: 1) 2 mL stabilizing solution 104B pH 9.5 (as defined above) and four 4 mm plus ten 2 mm glass beads; 2) 2 mL stabilizing solution 104B pH 11 (as defined above) and four 4 mm plus ten 2 mm glass beads; 3) 2 mL stabilizing solution 104B pH 9.5 and one 6 mm stainless steel ball; 4) 2 mL stabilizing solution 104B pH 11 and one 6 mm stainless steel ball. All four tubes were shaken by the donor by hand until mixed and brought back to the lab under ambient conditions. Within 3-4 hours of sample collection, DNA was extracted, quantified and 80 ng of each purified sample was run on an agarose gel (see Materials and Methods, and FIG. 7). Glass bead samples were vortexed and steel ball-containing samples were shaken prior to removal of an aliquot.

This example demonstrates the benefit of using a stainless steel mixing ball for stabilizing intact, high molecular weight DNA (>23 Kb) in freshly collected feces at room temperature. Mixing feces samples in laboratory tubes containing the present compositions, at both pH 9.5 and 11, and a single, dense stainless steel ball (FIG. 7B) proved to be superior to mixing with multiple small glass beads of two sizes (FIG. 7A) when comparing the quality of high molecular weight DNA on agarose gels. Hand mixing of feces with multiple glass beads and the present composition (104B pH 9.5) took significantly more time than mixing with a stainless steel ball, and the latter demonstrated a superior result in terms of preservation of intact, high molecular weight DNA. An improvement in DNA integrity in samples mixed with glass beads was surprisingly observed with an even more alkaline (pH 11) composition, suggesting that both the mixing/homogenization means and the pH of the stabilizing solution is critical.

Example 4—Volume Tolerance of Present Composition

Feces is a non-homogeneous biological sample which can vary significantly in appearance or hardness, according to the state of the digestive system, diet and general health. Normally stool is semisolid, with a mucus coating. The Bristol stool scale or chart is a medical aid designed to classify the form of human feces into seven categories, ranging from type 1 (separate hard lumps, like nuts) to type 7 (entirely liquid, no solid pieces, over 90% water). In general, feces consist of about 70-80% water, 20-30% of solid matter, but this percentage varies according to sample type (1-7) or residence time of feces in the intestine. Variability between feces in hardness and water content pose a significant challenge for feces collection and consistent, complete mixing with a stabilizing solution. Type 1-3 samples are particularly difficult to fully disperse in stabilizing solution to produce a homogenous liquid, without diluting the sample (and hence DNA) too far for downstream analysis. Also, type 1-3 samples have a greater tendency than other sample types to slowly absorb liquid, e.g. stabilizing solution, leading to a thick, semi-solid suspension which can be difficult to pipette in the laboratory. The higher water content of type 4-7 samples and softer consistency make these samples easier to mix in stabilizing solution and pipette. During processing, variability can also be introduced by the method (or commercial kit) used to extract DNA from fecal samples.

Figure 8B:
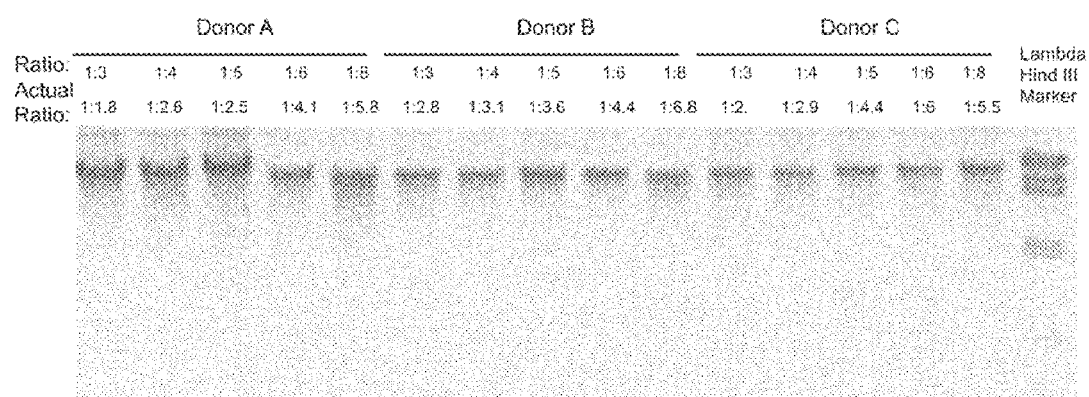
Figure 8C:
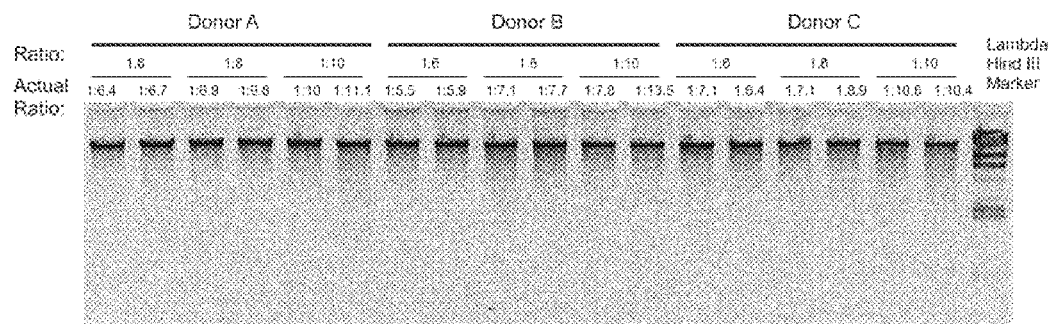
Figure 8D:
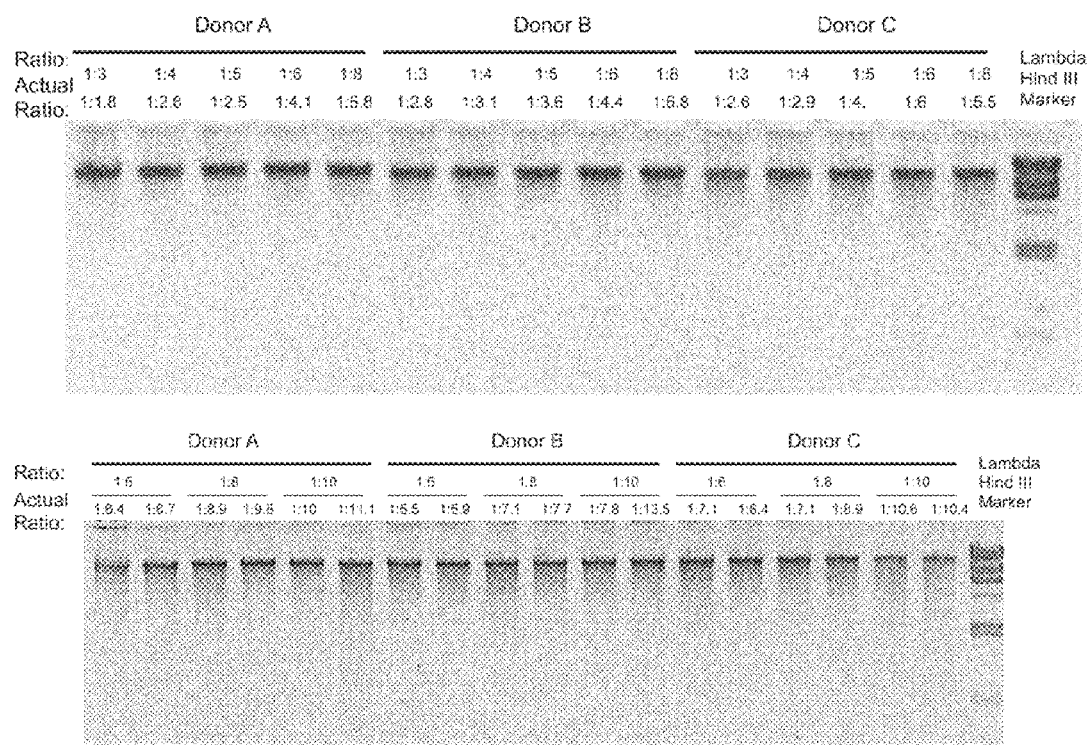
Figure 8E:
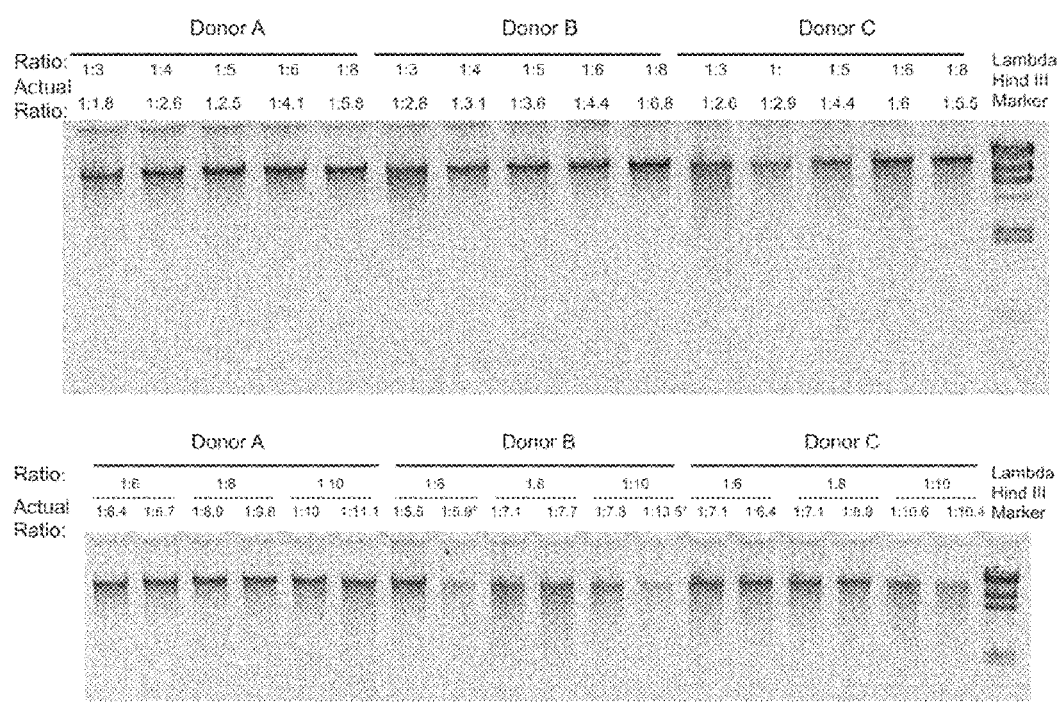
Figure 8F:
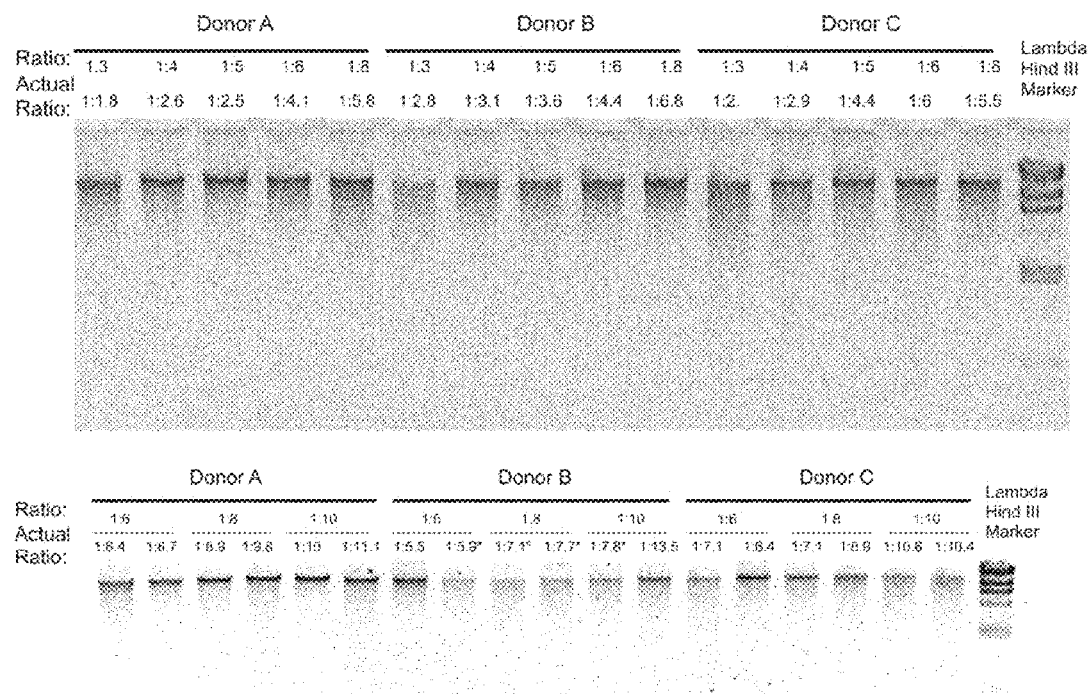

Given the non-homogeneous nature of feces, the robustness of the present composition to stabilize total, intact, high molecular weight DNA was compared in the following ratio experiments. In two separate experiments, three healthy donors collected feces samples (400 mg) into tubes containing a 7.9 mm stainless steel ball and various volumes of 104B pH 11 stabilizing solution (defined above), to achieve the following ratios of feces:stabilizing solution—1:3, 1:4, 1:5, 1:6, 1:8 and 1:10. Note, both the "Actual ratio" and targeted "Ratio" is indicated on the gels, since it is very difficult to repeatedly collect precisely 400 mg of feces with a crude tool. Tubes were weighed before and after sample collection to determine the exact amount of feces collected per volume of composition. Tubes were shaken by hand and 250 µL aliquots were removed at T=0 (FIG. 8A) and following 6 days (FIG. 8B), 7 days (FIG. 8C), 14 days (FIG. 8D), 1 month (FIG. 8E) and 2 months (FIG. 8F) at room temperature. In some case, two aliquots were extracted to demonstrate reproducibility of replicates (FIG. 8A, C-F). DNA was extracted and 80 ng was run on 1% agarose gels (FIGS. 8A-F). In lanes marked with an asterisk (*), less than 80 ng of DNA was loaded due to the fact that some samples had a DNA concentration less than 10 ng/µL once purified. DGGE gels (FIGS. 10A and 10B) also were performed in these experiments and percent similarities analyzed to determine the stability of the microbiome profile in these samples.

Figure 9:
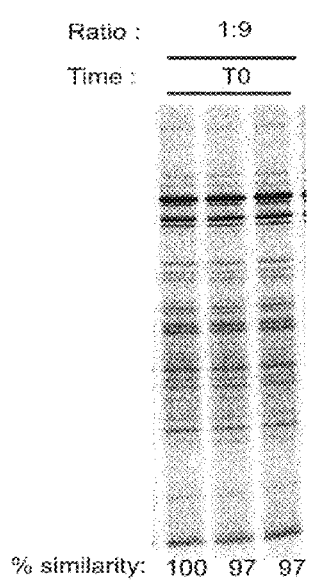
FIG. 9 shows DGGE gels of triplicate fecal sample aliquots from the same donor's specimen stored in the present composition.
Figure 10A:
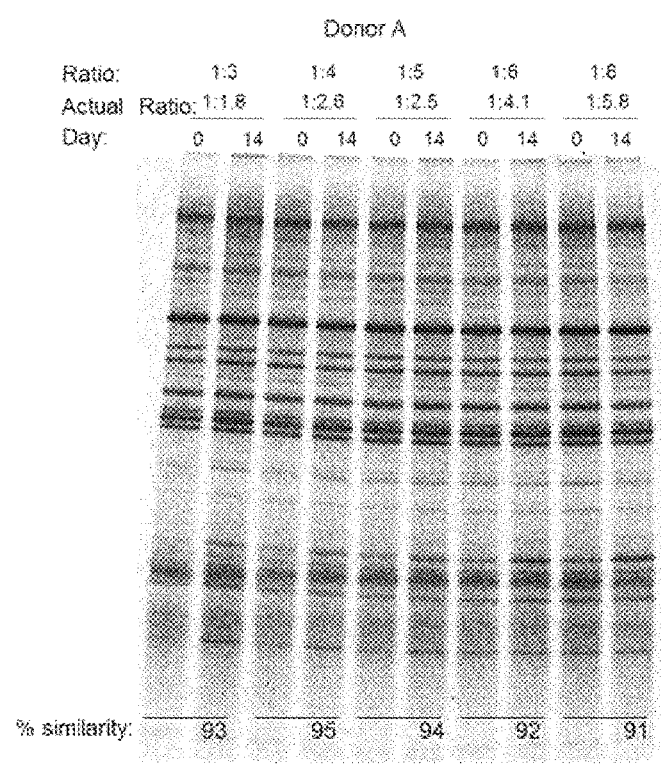
FIGS. 10A and 10B show a representative DGGE gel and % similarity (bottom of gel) of microbiome profile of fecal samples stored in the present composition for (A) 14 days at room temperature, and (B) 7 days and 2 months at room temperature.
Figure 10B:
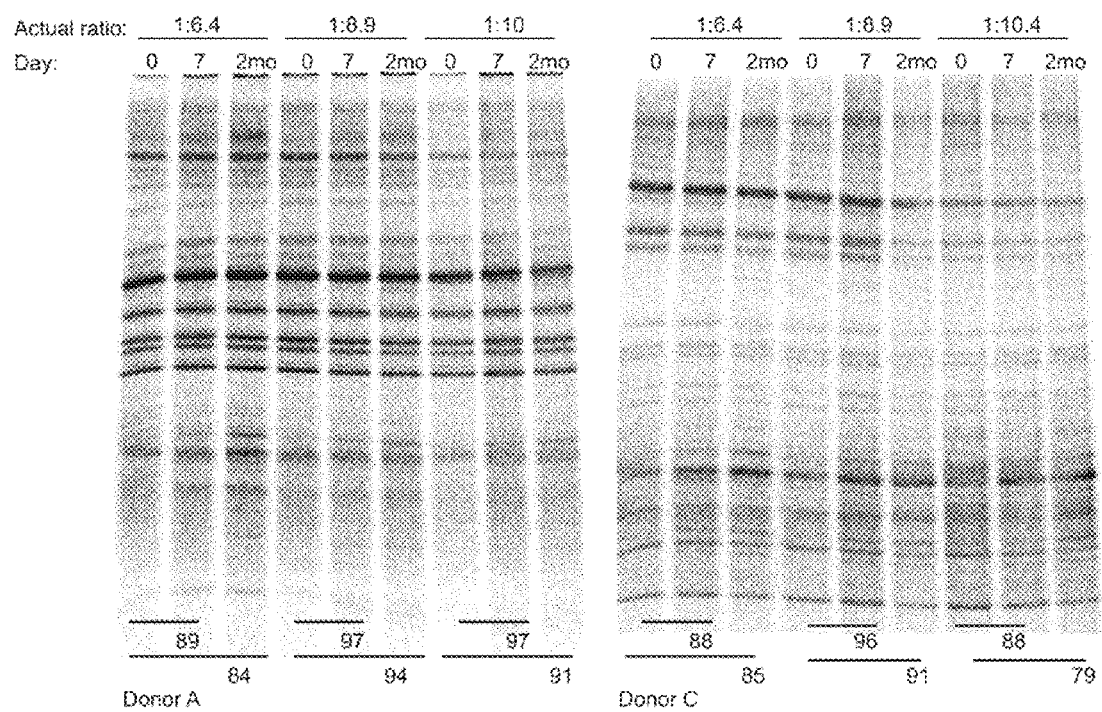

This example demonstrates that a wide range of feces: stabilizing solution ratios resulted in intact, high molecular weight DNA in samples from T=0 to at least 2 months storage at room temperature (FIGS. 8A-F). As little as 0.8 mL to as much as 5.4 mL of the present composition successfully stabilized DNA and microbiome profiles contained in 400 mg of feces for at least 2 months under these conditions (FIGS. 8A-F and 10A-B). This broad 'working' range gives the researcher comfort that donors can transfer highly variable amounts of fecal sample into tubes containing a fixed volume of stabilizing solution and the sample will be stable for at least 2 months at room temperature. Triplicate sample aliquots (FIG. 9) analyzed using DGGE demonstrated that the microbiome profile between aliquots taken from the same feces specimen was very consistent (≥97%). In addition, analysis of DGGE gels for the ratio experiments' samples showed that microbiome profiles were highly stabilized (≥88% at 7 days; ≥91% at 14 days; ≥79% at 2 months) in a broad range of feces:stabilizing solution of the present composition (1:1.8 to 1:10.6) for prolonged periods at room temperature (FIGS. 10A and 10B).

Preferred ratios of feces:stabilizing solution can therefore range from about 1:1 to 1:20, preferably 1:1 to 1:10, more preferably 1:3 to 1:8, and most preferably the ratio of feces:stabilizing solution is about 1:5.

The compositions described herein permit researchers to revolutionize how they collect large numbers of fecal samples. No longer do they need to limit studies due to the costs and logistics of shipping samples on dry ice or storing hundreds-thousands of fecal samples in freezers for months. Samples collected into tubes containing in the present composition can be shipped at ambient temperature in a bubble envelope and stored at room temperature in the lab for batch processing at the researcher's convenience.

Example 5—Stabilization of Samples in the Present Composition and Extreme Temperatures The various compositions described herein effectively and rapidly stabilize high molecular weight DNA and microbiome profiles in feces of human healthy donors at 'ambient' temperature. As noted above, 'ambient' means typical exposure temperatures observed during the collection, transport, storage and processing of biological samples. Depending upon where in the world the biological sample is collected/transported/stored, temperatures can easily range from −20° C. to 50° C., sometimes in a short period of time. It is known in the art that untreated biological samples degrade over these temperatures, particularly elevated temperatures. There is a need for a robust, universal biological sample stabilizing solution to maintain DNA in collected samples as close to the in vivo state as possible, i.e., prevent degradation of existing intact, high molecular weight DNA and/or prevent further degradation of partially degraded nucleic acid, such as human DNA in fecal samples, and stabilize the microbiome profile of fecal samples.

TABLE 7

Compositions tested.

| Name | Composition |
| --- | --- |
| 104B | 300 mM CDTA, 50 mM β-alanine, 23.5% ethanol, 0.5% SDS, 0.1% Antifoam A, pH 11 |
| CBE | 300 mM CDTA, 50 mM β-alanine, 23.5% ethanol, pH 11 |
| CB | 300 mM CDTA, 50 mM β-alanine, pH 11 |
| CBS | 300 mM CDTA, 50 mM β-alanine, 0.5% SDS, pH 11 |
| CBSA1 | 300 mM CDTA, 50 mM β-alanine, 0.5% SDS, 0.1% Antifoam A, pH 11 |

TABLE 7-continued

Compositions tested.

| Name | Composition |
| --- | --- |
| CBSA2 | 300 mM CDTA, 50 mM β-alanine, 0.5% SDS, 0.01% Antifoam A, pH 11 |

The performance of 6 DNA stabilizing compositions (Table 7), developed by the inventors, was tested and compared over a broad range of ambient temperatures, e.g. −20° C., room temperature (generally 19-23° C.), 37° C., and 50° C., with complex, non-homogeneous, variable fecal samples. In the first experiment, 2 healthy donors each transferred 400 mg feces into 6 tubes containing 2 mL of the different compositions (Table 7) and one 7.9 mm stainless steel ball. Tubes were shaken by hand to homogenize the fecal samples, an aliquot (250 μL) was immediately removed for DNA extraction (T=0) and then tubes were stored at 37° C. for 7 and 21 days.

Figure 11A:
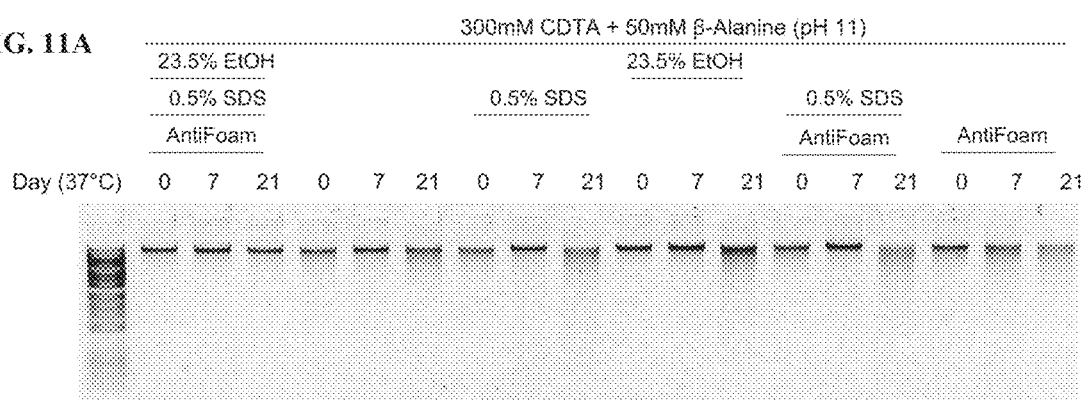
FIGS. 11A and 11B show agarose gels of fecal samples from 2 donors stored at 37° C. in the present compositions.
Figure 11B:
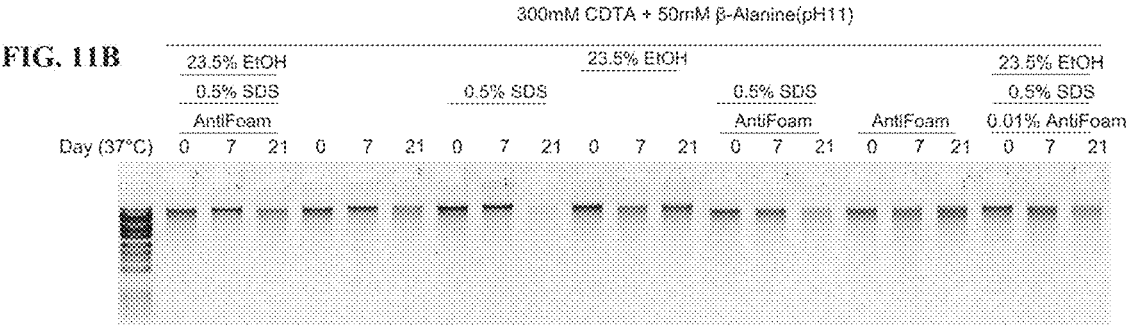
Figure 12A:
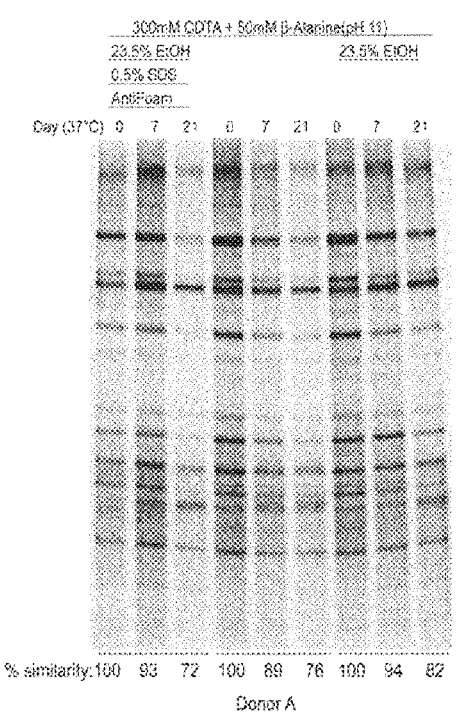
FIGS. 12A and 12B show DGGE analysis of fecal samples from 2 donors stored at 37° C. in the present compositions.
Figure 12B:
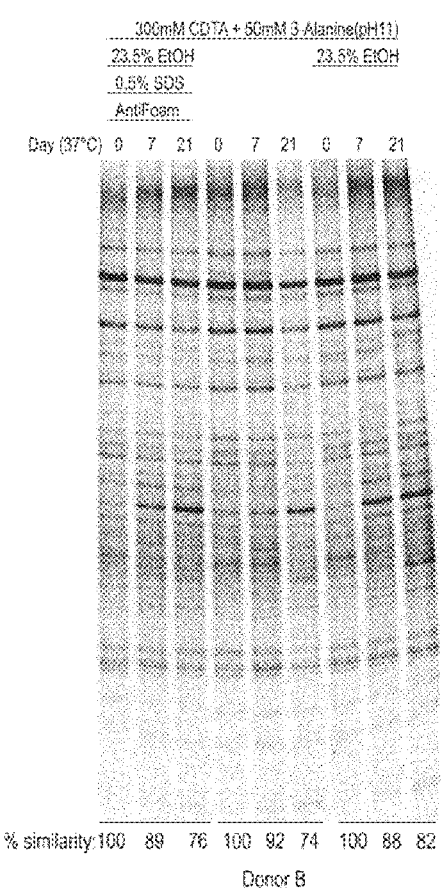

FIGS. 11A and 11B demonstrate that all compositions tested stabilized intact, high molecular weight DNA for at least 3 weeks when fecal samples were stored at 37° C. After 21 days at 37° C., the concentration of DNA recovered from stool samples stored in CBS, CBSA1, and CBSA2 compositions was lower than samples in the other compositions, leading to fainter bands on the agarose gels for donor A and B (FIGS. 11A and 11B). Surprisingly, DGGE analysis (FIGS. 12A and 12B) showed the microbiome profile in these samples was also stable for the first week at 37° C., an optimum temperature for growth of fecal bacteria, and started to change prior to the 21 day time point. In addition to 300 mM CDTA, buffered to pH 11, ethanol appears to be beneficial for stabilization or recovery of both high molecular weight DNA and microbiome profile.

Figure 13A:
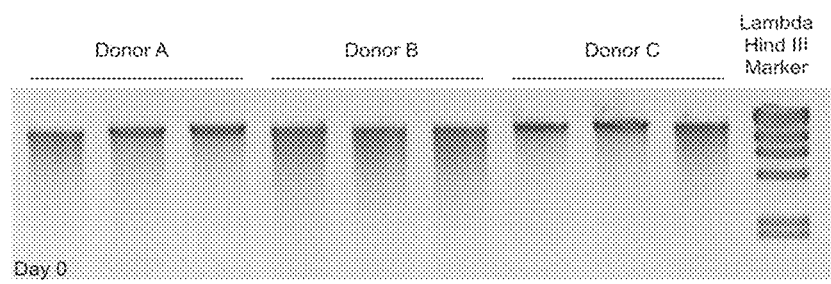
FIGS. 13A-E show agarose gels of fecal samples from 3 donors stored in the present composition at −20° C., room temperature, and 50° C.
Figure 13B:
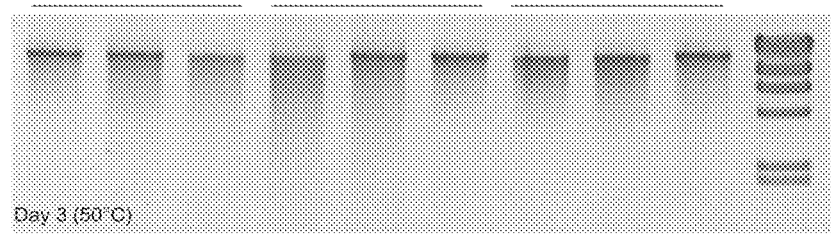
Figure 13C:
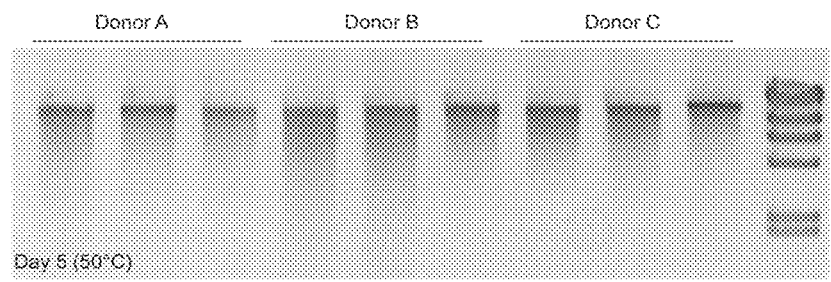
Figure 13D:
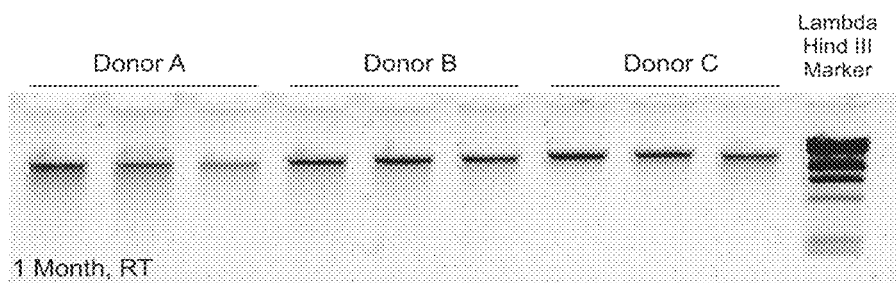
Figure 13E:
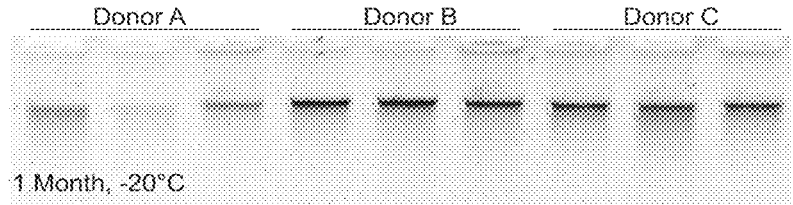

In the second experiment, 3 healthy donors each transferred 400 mg feces into 3 tubes containing 2 mL of 104B and one 7.9 mm stainless steel ball. Tubes were shaken by hand to homogenize the fecal samples, an aliquot (250 μL) was immediately removed for DNA extraction (T=0), and then tubes were stored at 50° C. for 3 and 5 days, room temperature for 1 month, and −20° C. for 1 month (FIGS. 13A-E). FIGS. 13A-E demonstrates that 104B stabilized high molecular weight DNA for at 5 days at 50° C. (FIG. 13B-C), 1 month at room temperature (FIG. 13D), and 1 month at −20° C. (FIG. 13E). Triplicate fecal samples collected by each donor all contained intact, high molecular weight DNA, irrespective of temperature or time period tested.

Figure 14A:
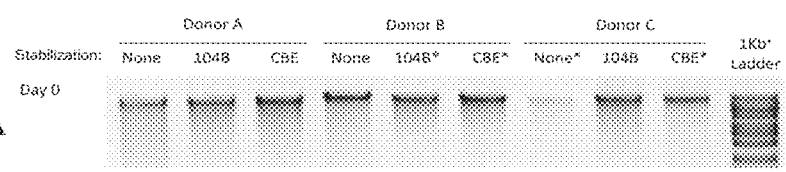
FIGS. 14A-D show agarose gel electrophoresis of fecal samples from 3 donors stored in the present compositions at 50° C. and −20° C.
Figure 14B:
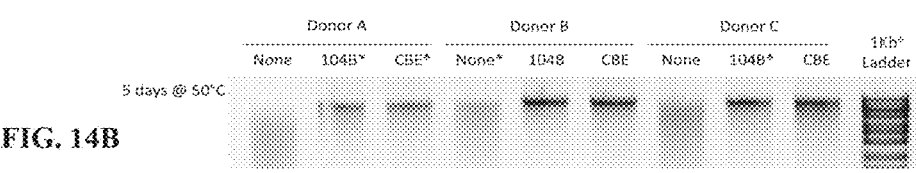
Figure 14C:
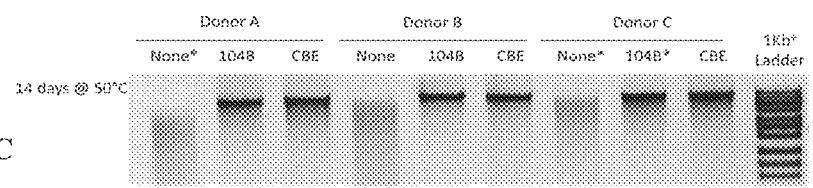

In the third experiment, 3 healthy donors each transferred 400 mg feces into 3 tubes; 2 tubes contained 2 mL of 104B and CBE (Table 7) and one 7.9 mm stainless steel ball each; the third tube was empty (none). Tubes with stabilizing solution were shaken by hand to homogenize the fecal samples, an aliquot (250 μL or 250 mg) was immediately removed from each tube for DNA extraction (T=0), and then tubes were stored at 50° C. for 5 and 14 days or −20° C. for 11 days (FIG. 14 A-D). FIGS. 14A-C demonstrates that both 104B and CBE maintained intact, high molecular weight DNA for at least 2 weeks at 50° C., while control (none) samples showed signs of degradation over time. Surprisingly, DGGE analysis (FIGS. 15A and 15B) showed the microbiome profile in these samples was also stable for 2 weeks at 50° C., an extreme temperature for biomolecules like DNA. Interestingly, the percent similarities were higher in samples stored at 50° C. for 5 days, not 14 days, indicating that prolonged exposure to such an extreme temperature may lead to some chemical instability of the DNA itself.

Figure 14D:
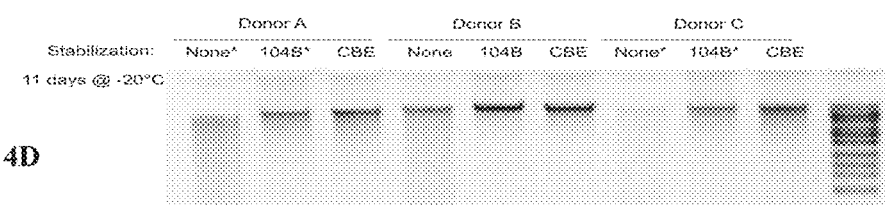
Figure 15A:
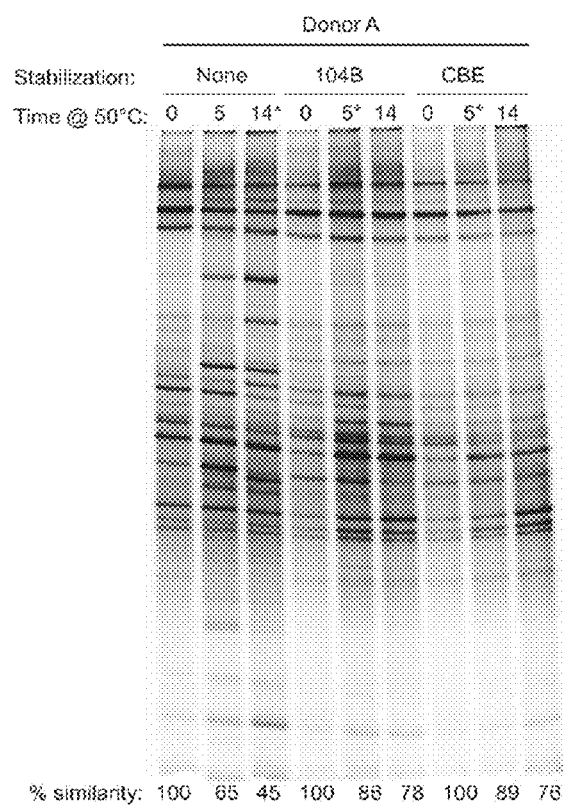
FIGS. 15A-B show DGGE analysis of fecal samples from 2 donors stored in the present compositions at 50° C. for 14 days.
Figure 15B:
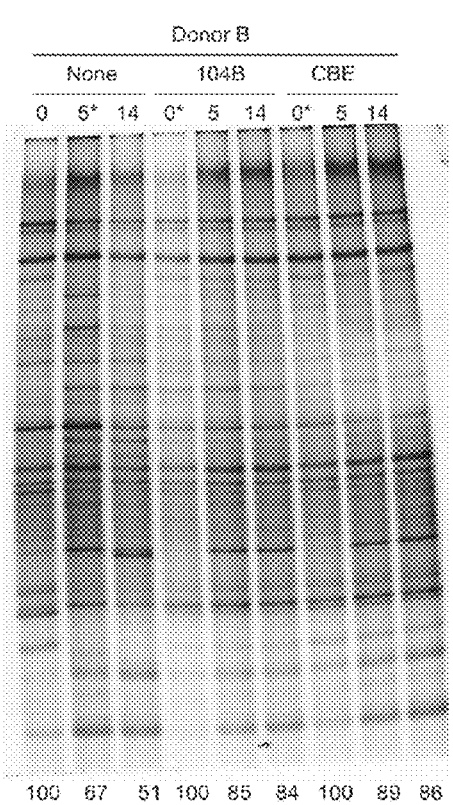

FIG. 14D shows that both 104B and CBE maintained high molecular weight DNA in −20° C. frozen (and subsequently thawed) samples for at least 11 days. However, in the absence of stabilizing solution, feces showed characteristic signs of DNA degradation at −20° C. In donor A (none) sample, the majority of high molecular weight DNA was degraded and appeared as a smear on the agarose gel. In contrast, a small amount of high molecular weight DNA could still be detected in donor B and C samples, indicating donor variability. DGGE analysis of samples without stabilizing solution confirmed the microbiome profile was not stable at −20° C.; % similarity to the control T=0 was 52 and 69% for donor A and C, respectively. In contrast, the microbiome profile was stable in 104B and CBE for 11 days at −20° C., as indicated by the high percent similarities to control (none) samples (FIGS. 16A and 16B).

Taken together these examples demonstrate that both 104B and CBE stabilize DNA in fecal samples stored at extreme temperatures for prolonged periods of time.

Example 6—Stability with Freeze/Thaw Cycling of Feces Samples Incubated in Present Composition As discussed above, the microbiome profile is known in the art to change when feces is exposed to just one round of freezing and thawing for storage or banking purposes. This degradation adds an unnecessary bias to all collected samples transported and/or stored at subzero temperatures. In the present example, feces was collected from 3 healthy donors and 400 mg samples were transferred to empty tubes and tubes containing 2 mL of the present composition ("104B pH 9.5"; as defined above) with glass beads (four 4 mm and ten 2 mm beads). Tubes containing stabilizing solution and glass beads were vigorously vortexed until completely mixed. Following removal of a 250 mg or μL aliquot for DNA extraction at day 0, sample tubes were stored in a −20° C. freezer and, over the course of ten days, cycled five times between the freezer and room temperature with 24 hours at each temperature. Sample tubes were thawed at 50° C. for 3 hours, an industry standard method.

Figure 18:
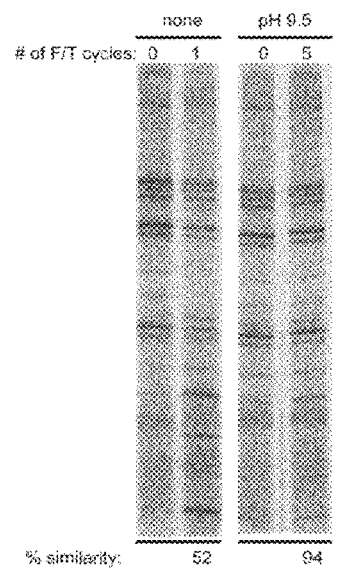
FIG. 18 shows DGGE analysis of fecal samples in the present composition and exposed to 5 freeze/thaw cycles.

Agarose gel analysis of day 0 aliquots demonstrates that each donor's feces contained high molecular weight DNA when collected into the present composition (FIG. 17). Surprisingly, after 5 cycles of freeze/thaw (F/T) the DNA remained intact (FIG. 17). DGGE analysis confirmed the microbiome profile of samples in the present composition remained stable at 94% following 5 F/T cycles (FIG. 18). In stark contrast, unprotected samples showed considerable degradation of the microbiome profile. After just one F/T cycle, the profile was only 52% similar to the profile of the day 0 'freshly collected' sample, prior to −20° C. exposure. Hence, the present composition not only preserves intact, high molecular weight DNA with multiple rounds of freezing and thawing, it stabilizes the microbiome profile as well, dramatically reducing the bias associated with these storage conditions.

Example 7—Homogenization of Fecal Samples Collected in the Present Composition

As described above, the inventors experimented with numerous different materials which could be used in a standard, commercially-available 10 mL laboratory and/or transport tubes (92 mm×15.3 mm, internal diameter of about 12.9 mm) to completely and reliably homogenize fecal samples of all types (1-7, Bristol Stool Scale). It was determined that the mixing should be done by hand and in a relatively short period of time (within 180 seconds) to ensure that donors will comply and consistently provide stabilized biological samples. A person skilled in the art will understand how to select an appropriate homogenization means for containers larger or smaller than the one used in the present Examples (see Detailed Description).

A standard, disposable 3 mL syringe was modified to collect and transfer a small, volumetric amount of feces into the collection tube above, containing the present composition ("104B pH 11"; defined above) and homogenization means. The tapered tip or fitting for the needle of the syringe was cut off to expose the barrel of uniform diameter. The plunger was pre-set to a position which facilitated the collection of a consistent amount of feces, e.g. 400 mg, when it was pushed into a container containing feces. A small vent hole was drilled in the barrel of the syringe for air to escape during fecal sample collection. The syringe with loaded sample was transferred to the opening of the tube and the plunger was depressed, depositing the 400 mg sample into the tube containing 2 mL of stabilizing solution and the homogenization means (e.g. homogenization ball, specified below). The tube was capped and shaken by hand for about 20-40 seconds, longer (1-3 minutes) for hard type 1 samples (see below). After vigorously shaking the sample in a back and forth motion, in the presence of the homogenization means, the fecal sample was distributed in the stabilizing solution.

When the selected container is a laboratory or transport tube/vial, a homogenization "ball" or "sphere" of the appropriate size, shape and density is critical for complete dispersion of non-homogeneous, complex samples in the present composition. Thorough homogenization of the collected sample at the time of collection is also critical for optimal stabilization of human and microbial DNA, as evidenced by the presence of intact, high molecular weight DNA as well as stabilization of the microbiome profile as exemplified via PCR of bacterial 16S rRNA gene and DGGE analysis of the amplicons. As described above, for a spherical homogenization means, the bottom of the transport tube/vial should also be round, mirroring the shape of the homogenization means, to prevent solid matter from being compacted into dead spaces inside the tube. For instance, optimal homogenization of fecal samples (particularly type 1-3) with spherical homogenization means is very difficult to achieve with conical- or flat-bottomed tubes. A spherical homogenization means cannot make direct contact with the conical surface nor 90 degree angles where the vertical tube walls intersect the base, causing compaction of fecal matter in these dead spaces/areas.

The following Tables 8-10 illustrate some of the different commercially-available materials tested by the inventors to find the optimal homogenization means for a standard laboratory/transport tube (e.g. Cat. No. 60.610, Sarstedt).

TABLE 8

Mixing time (seconds) for balls of different material, diameter and number.

| Feces Sample Type | Tungsten Carbide (15.63 g/cm³) | | | | Alumina Oxide (3.95 g/cm³) | Silicon Nitride (3.21 g/cm³) | | Glass (2.65 g/cm³) | | | | | 2.0 mm & 4.0 mm |
|---|---|---|---|---|---|---|---|---|---|---|---|---|---|
| | 7.1 mm | 7.1 mm | 7.9 mm | 7.9 mm | 7.9 mm | 7.1 mm | 7.9 mm | 2 mm | 2 mm | 3.5 mm | 4 mm | 12.7 mm | |
| | 1 | 2 | 1 | 2 | 1 | 1 | 1 | 4 | 10 | 4 | 4 | 1 | 10 & 4 |
| 1 | 140 | 80 | 100 | 80 | X | X | X | X | X | X | X | X | X |
| 2 | 40 | 30 | 40 | 40 | X | X | X | X | X | X | X | X | X |
| 3 | 30 | 30 | 30 | 20 | X | X | X | X | X | X | X | X | X |
| 4 | 15 | 10 | 10 | 10 | 100 | 160 | 160 | X | X | X | X | X | X |
| 5 | 15 | 10 | 10 | 10 | 100 | 135 | 135 | 60 | 60 | 60 | 50 | X | 50 |
| 6 | 10 | 10 | 10 | 10 | 50 | 65 | 60 | 40 | 30 | 30 | 30 | X | 30 |
| 7 | ND | ND | ND | ND | ND | ND | ND | ND | ND | ND | ND | ND | ND |

ND, not determined;
X, >180 seconds

TABLE 9

Mixing time (seconds) for stainless steel balls of different diameter.

| Feces Sample Type | Stainless Steel Ball (7.6-7.9 g/cm³) | | | | | | | | | | | | | |
|---|---|---|---|---|---|---|---|---|---|---|---|---|---|---|
| | 4.8 mm | 4.8 mm | 4.8 mm | 5.6 mm | 5.6 mm | 7.1 mm | 7.1 mm | 7.9 mm | 7.9 mm | 8.7 mm | 8.7 mm | 9.5 mm | 10.3 mm | 11.1 mm |
| | 2 | 4 | 6 | 1 | 2 | 1 | 2 | 1 | 2 | 1 | 2 | 1 | 2 | 1 | 1 |
| 1 | X | X | X | X | X | X | 180 | X | 145 | 180 | 60 | X | X | 180 | X |
| 2 | X | 90 | 90 | X | 60 | 60 | 50 | 80 | 50 | 40 | 50 | 50 | X | X | 90 |
| 3 | X | 90 | 90 | 100 | 90 | 80 | 60 | 35 | 50 | 40 | 30 | 45 | 30 | 65 | 80 |
| 4 | X | 100 | 100 | 120 | 95 | 55 | 25 | 20 | 15 | 25 | 10 | 25 | 10 | 20 | 25 |
| 5 | 50 | 60 | 50 | 50 | 40 | 50 | 20 | 20 | 20 | 20 | 10 | 15 | 10 | 10 | 15 |
| 6 | 30 | 30 | 30 | 30 | 20 | 20 | 10 | 20 | 10 | 20 | 10 | 10 | 10 | 10 | 20 |
| 7 | ND | ND | ND | ND | ND | ND | ND | ND | ND | ND | ND | ND | ND | ND | ND |

ND, not determined;
X, >180 seconds

TABLE 10

Mixing time (seconds) for stainless steel balls of different diameter and number.

| Feces Sample Type | Stainless Steel Ball (7.6-7.9 g/cm³) | | | | |
|---|---|---|---|---|---|
| | 5.6 mm & 4.8 mm 1 each | 7.1 mm & 4.8 mm 1 each | 7.1 mm & 5.6 mm 1 each | 7.9 mm & 4.8 mm 1 each | 7.9 mm & 7.1 mm 1 each |
| 1 | X | X | X | X | X |
| 2 | 60 | 60 | 60 | 50 | 50 |
| 3 | 70 | 70 | 70 | 60 | 40 |
| 4 | 100 | 60 | 60 | 50 | 25 |
| 5 | 30 | 30 | 20 | 20 | 20 |
| 6 | 30 | 30 | 20 | 20 | 10 |
| 7 | ND | ND | ND | ND | ND |

ND, not determined; X, >180 seconds

Feces of sample types 1 and 2 are very dense and contain little water, making them impenetrable for dispersion by hand in the present composition within a reasonable period of time (<3 minutes), without a homogenization means. For softer feces (type 3-6) a homogenization means was still required and the duration of mixing the tube by hand reduced considerably with increasing sample type (Tables 8-10). A homogenization means was not essential to disperse sample type 7 or diarrhea with the present composition. In this context, the purpose of the "homogenizer" was to completely disrupt and disperse a non-homogeneous solid or semi-solid sample throughout the stabilization solution, without the use of electricity or batteries.

Important features of the homogenization means include 1) density of the material, 2) size with respect to the internal diameter of the container for the biological sample, and 3) shape with respect to the container. Glass (about 2.0-4.5 g/cm3)/poly(methyl methacrylate or PMMA (about 1.2 g/cm3)/silica (about 1.6-2.0 g/cm3)/zirconia (about 6.02 g/cm3)/cellulose acetate (about 1.3 g/cm3)/polyethylene (about 0.9-1.3 g/cm3) particles (<1.2 mm) and small beads (≤4 mm) were not sized, nor dense enough, to function as a homogenizer for type 1-4 feces within a standard laboratory tube having an internal diameter of 12.9 mm (Table 8). Importantly, even large 7.9 mm balls made from alumina oxide (3.95 g/cm3) or 7.1-7.9 mm silicon nitride (3.21 g/cm3) and 12.7 mm glass marbles were not able to disperse type 1-3 feces samples (400 mg) in 2 mL of the present composition in less than 180 seconds (Table 8). Surprisingly, even after 180 seconds of shaking the tube hard, solid matter remained intact in the present composition. These experimental results led to the testing of more dense materials, i.e. densities >3.95 g/cm3. Unfortunately, balls with densities between 3.95 g/cm3 and 7.6 g/cm3 were not commercially available and therefore couldn't be tested with fecal samples.

Next, stainless steel (7.6-7.9 g/cm3, Tables 9 and 10) and tungsten carbide balls (15.63 g/cm3, Table 8) were tested with 400 mg fecal samples in 2 mL of the present composition within a round bottom tube. Surprisingly, even hard nut-like type 1 fecal samples were homogenized by 7.1-7.9 mm tungsten carbide and 7.1-8.7 mm stainless steel balls in ≤140 and ≤180 seconds, respectively. Type 2 samples were homogenized by 7.1-7.9 mm tungsten carbide and 7.1-8.7 mm stainless steel balls in ≤40 seconds and ≤80 seconds, respectively. Tungsten carbide (7.1-7.9 mm) and stainless steel balls (7.1-8.7 mm) homogenized type 3 samples in ≤30 and ≤80 seconds, type 4 samples in ≤15 and ≤55 seconds, type 5 samples in ≤15 and 50 seconds, and type 6 sample in ≤10 and ≤22 seconds, respectively.

Similarly, balls with densities between 7.9 g/cm3 to 15.63 g/cm3 could not be sourced or tested; however, one skilled in the art would expect such homogenization means to disrupt fecal samples certainly in less than 180 seconds in the 7.1-8.7 mm size range. Solely for cost and ease of sourcing, stainless steel balls were preferred to tungsten carbide balls and the optimal diameter was 7.1-8.7 mm in diameter. Addition of a second ball of the same size generally proved beneficial in reducing the mixing time (Tables 8 and 9). In some instances, combinations of balls of more than one size were beneficial for reducing the time required to homogenize fecal samples (Table 10).

Given that 7.1-8.7 mm balls performed the best in tubes with 12.9 mm internal diameter, about 2.1-2.9 mm clearance on either side of the ball provided the optimal fit in the tube to homogenize the sample in a short period of time. When the stainless steel balls were 5.6 mm or 9.5 mm in diameter, the mixing time for hard type (1-4) fecal samples increased. Hence, given these results for fecal samples ranging in consistency from solid to liquid, 7.9 mm stainless steel balls have been preferably employed as homogenization means in examples described herein, unless otherwise stated.

Example 8—Stabilization of the Gut Microbiota Profile Using the Present Composition Analysis of the gut microbiota has been of increasing interest to researchers investigating the beneficial and deleterious roles of microorganisms in human health. For any analysis of the gut microbiota, it is essential to accurately capture a "snap-shot" of the microbiota profile (i.e., ensuring the relative abundance of Operational Taxonomic Units [OTU] remains unchanged from the time of collection to time of sample processing and analysis) that represents the in vivo state; thus, sample stabilization at the time of collection is of paramount importance to such studies. Current methods for stool sample collection and microbiota analysis involve transport of samples at ambient temperature, 4° C. or frozen. However, these methods have the potential to expose samples to temperatures incompatible with microbiome stabilization and freezing stool specimens has been shown previously to alter the Firmicutes to *Bacteroides* ratio (Bahl et al., (2012) FEMS Microbiol Letters 329: 193-197).

In this example, the stability of the microbiome was assessed using a sensitive, commercially-available method, 16S rRNA sequencing of the V4 hypervariable region. For this study, four donors each collected one stool specimen and placed equal amounts of sample (400 mg) into three tubes without stabilizing solution and six tubes with stabilizing solution (300 mM CDTA, 0.5% SDS, 23.5% ethanol, 0.1% Antifoam A, 0.2% Triclosan, pH 9.5) and a 7.9 mm stainless steel mixing ball. Donors transported the samples to the lab at ambient temperature where a T=0 aliquot (250 µL or 250 mg) was removed and DNA extracted using the POWERFECAL® DNA Isolation Kit (MO BIO Laboratories). One sample per donor per stabilization condition was stored at each of the test temperatures (−20° C., 4° C., 23° C., 37° C.—in stabilization solution only) for 3 and 14 days, followed by DNA extraction. One sample in stabilization solution was exposed to five freeze-thaw cycles.

At the indicated time points, DNA from aliquots was extracted and sent for 16S rRNA sequencing library preparation, sequencing and bioinformatics. V4 hypervariable region paired-end amplicon sequencing was performed using the ILLUMINA® MISEQ® (250 cycles).

Figure 19:
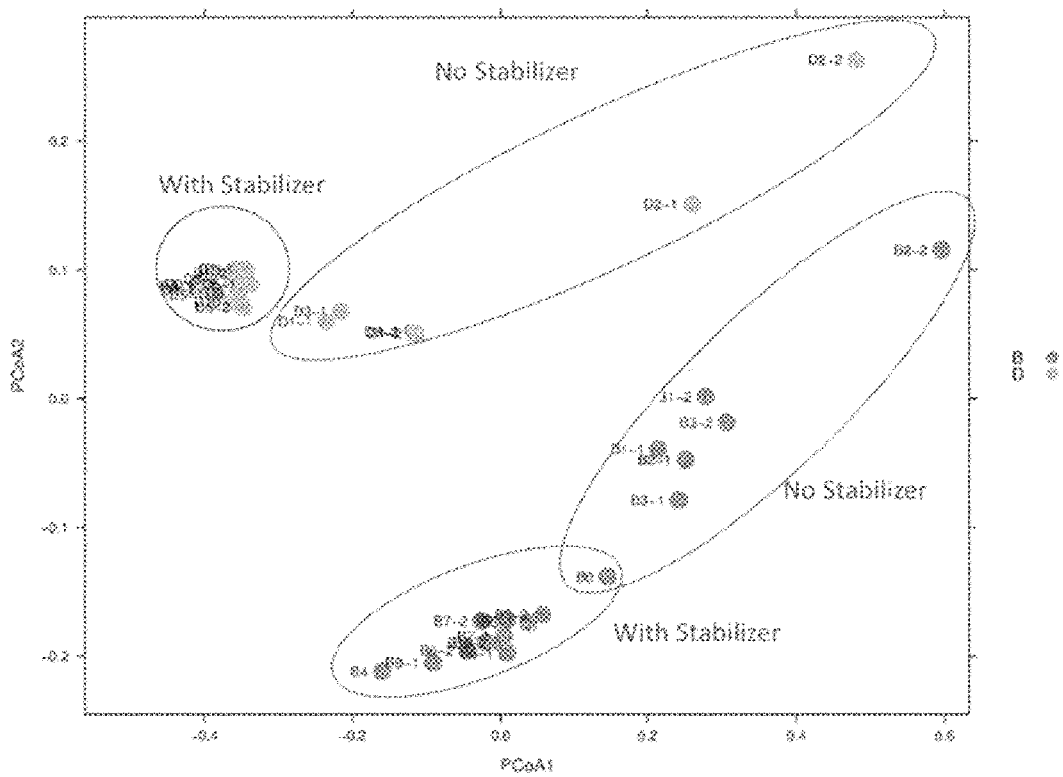
FIG. 19 shows principal coordinate analysis (PCoA) that demonstrates that samples stored in stabilization solution over various temperatures and time (3 and 14 days) exhibit a high level of similarity in OTU abundance.
Figure 20:
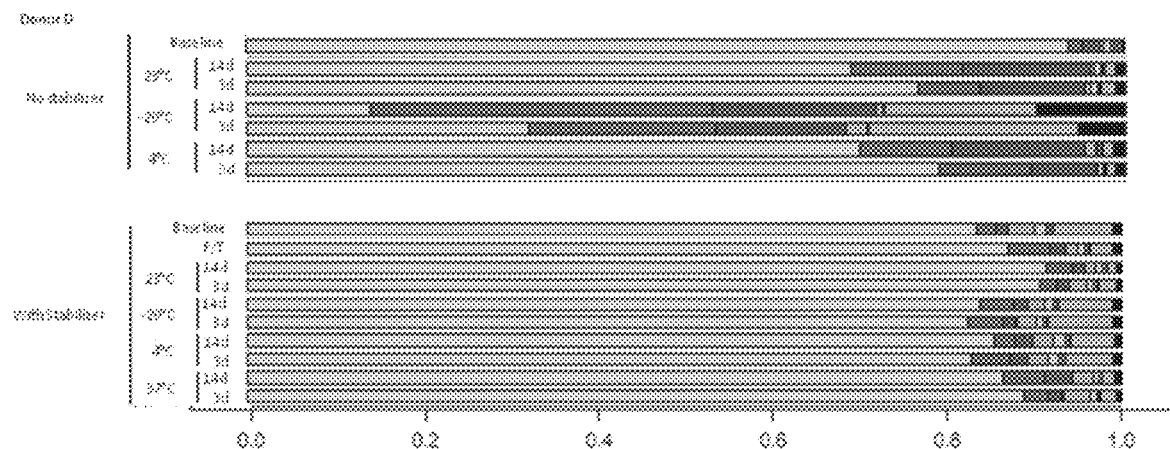
FIG. 20 shows family level proportional abundance of samples stored with and without stabilization solution over various temperatures and time (3 and 14 days).

FIGS. 19 and 20 present data that indicates that samples fully preserved in stabilization solution have high degree of similarity in OTU abundance.

In FIG. 19, principal coordinate analysis (PCoA) based on weighted unifrac dissimilarity values demonstrate in two donors (B and D) that samples stored in stabilization solution over various temperatures (−20° C., 4° C., ambient temperature, 37° C.) and time (3 and 14 days) exhibit a high level of similarity in OTU abundance as shown by tight clustering on the PCoA plot (samples stored in stabilization buffer have sample identification numbers with a 4-9 as the first digit, e.g. D4 and B4, and are grouped into the "With Stabilizer" circles for each donor). In contrast, samples stored without stabilization solution (samples with identification numbers with a 0-3 as the first digit, e.g. D3-1 and B3-1, and grouped into the "No Stabilization" circles for each donor) demonstrated a loss of similarity in OTU abundance as shown by the greater distances between samples. Importantly, when assessing presence or absence of OTUs, there was a statistically significant difference between stabilized samples and those without stabilization solution in all four donors (p=0.002, 0.002, 0.002 and 0.009 respectively, Unifrac measurement). The greatest profile changes were observed in samples stored at −20° C. without stabilization solution (samples B2-1, B2-2, D2-1 and D2-2 on the PCoA plots), which were significantly different from samples stored at −20° C. in stabilization solution (p=0.028, Weighted Unifrac measurement); thereby demonstrating that storing samples in the novel stabilization solution can prevent changes in microbial profile observed in non-stabilized frozen samples (FIG. 19).

In FIG. 20, proportional abundance at the family-level demonstrates a change in the composition of samples stored without the present stabilization solution at various temperatures over time (3 and 14 days). In particular, an increase in the Lachnospiraceae, Ruminococcaceae and Prevotellaceae and a loss of Bacteroidaceae is observed in donor D's samples without stabilization solution compared to baseline. In contrast, samples stored with the stabilization solution over various temperatures and time maintained the microbial composition of the sample compared to baseline sample.

This data suggests that in order to robustly correlate changes in the gut microbiota to the phenotype of interest, it is important to have a reproducible way of stabilizing the profile at the point of collection, something that current temperature-based stabilization methods are not able to achieve effectively. The stabilization chemistry demonstrated here has the ability to maintain the in vivo profile of the gut microbiota (i.e. tight clustering of OTUs) at various transport temperatures, allowing researchers to improve data reliability and inter-study comparison. This stabilization chemistry will also increase the ease of unsupervised self-collection, and will uniquely enable large population studies that are currently logistically difficult.

Example 9—Stabilization of Human DNA in the Present Composition

See Materials and Methods section for further details on fecal sample collection, extraction and quantification of DNA, and amplification of human DNA.

Three healthy donors were provided instructions and materials to collect a fecal sample at home. After defecating into a large container attached to the toilet, approximately 400 mg of feces was immediately transferred into a 10 mL round-bottom tube containing 2 mL of the present composition ("104B pH 11"; defined above) and one 7.9 mm stainless steel ball. After capping the tube, donors shook the sealed tube for about 20 seconds to homogenize the sample in the composition. Donors generally returned the homogenized samples to the lab at ambient temperature within 3-4 hours of collection. In the lab, a T=0 aliquot (250 μL) was removed from each tube and the remainder was stored at room temperature (RT) for 14 days, at which time a second aliquot (250 μL) was withdrawn.

DNA was purified from each aliquot using POWERFECAL® DNA Isolation Kit; DNA yield was quantified using PICOGREEN® fluorescent dye and a fluorometric method (see Materials and Methods). Human DNA purified from T=0 and T=14 day fecal samples was amplified in real-time or quantitative PCR (qPCR) using primers targeting the single copy human thymidylate synthase gene. The change in Ct ($\Delta$Ct) values, i.e., the difference in triplicate Ct values resulting from T=0 and T=14 day purified aliquots taken from the same sample, is shown in Table 11 below. For each donor, the amount of human DNA detected in purified samples at T=0 and T=14 days is equivalent. With less than one cycle difference in DNA from fecal samples processed immediately or stored for 2 weeks at RT, this example demonstrates that human DNA is stable in the present composition for all three donors.

TABLE 11

Change in Ct values for human DNA in fecal samples stored at room temperature for 14 days or processed at T = 0.

|  | $\Delta$Ct ($C_{14}$-$C_0$) |
| --- | --- |
| Donor A | 0.94 |
| Donor B | 0.11 |
| Donor C | 0.77 |

Example 10—The Present Composition Stabilizes the Microbiome Profile at Room Temperature for 14 Days, and Under Simulated Transport Conditions The present composition enables the easy self-collection and stabilization of microbial DNA from feces for gut microbiome profiling. It is uniquely able to take a snapshot of the microbial profile at the moment of collection, and maintain it for 14 days at room temperature.

In this example, six healthy donors were provided instructions and materials to collect a fecal sample at home. After defecating into a large container attached to the toilet, approximately 400 mg of feces was immediately transferred to a 10 mL round-bottom tube containing 2 mL of the present composition ("104B pH 11"; defined above) and one 7.9 mm stainless steel ball. After capping the tube, donors shook the sealed tube for about 20 seconds to homogenize the sample in the composition. Each of 6 donors collected 3 samples from the same bulk fecal sample (n=18 total) into the present composition. Additionally, 400 mg aliquots of fresh feces were collected from the same bulk fecal sample by each donor and transported in empty 10 mL tubes in a styrofoam box with frozen cold packs as per Human Microbiome Project standard procedure (Manual of Procedures—Human Microbiome Project, 2010).

Baseline DNA extractions were performed within 3 hours of collection. For baseline analysis, a 0.25 mL aliquot was taken from 104B pH11 samples and extracted using the POWERFECAL® DNA Isolation Kit (MO BIO Laboratories, Inc.). Each 0.25 mL sample contained approximately 50 mg feces and 200 μL stabilizing liquid, 104B pH 11. Equivalent amounts of feces (approximately 50 mg) were extracted from fresh, unstabilized samples. Remaining 104B pH 11 and fresh, unstabilized samples were aliquoted and stored at room temperature (23±3° C.) for 14 days or exposed to simulated transport conditions (50° C. for 1 day, 37° C. for 3 days or 3 cycles of freeze thaw where one cycle consisted of a minimum of 3 hours at −20° C. and a minimum of 3 hours at 30° C.). Additionally, an aliquot of fresh stool from each donor was stored at −80° C. as a control. After the 14 day hold at room temperature, simulated transport conditions or −80° C., a second aliquot was extracted from all samples using the POWERFECAL® DNA Isolation Kit.

DNA concentration and yield were determined using the QUANT-IT™ PICOGREEN® reagent (Life Technologies). DNA integrity and stability over time was evaluated by running approximately 50 ng of purified DNA on a 0.8% agarose gel and staining with ethidium bromide. A Lambda Hind III ladder was used to determine the size of purified DNA.

16S rRNA sequencing library preparation, sequencing and bioinformatics were conducted by Metanome, Microbiome Discovery Service. V4 hypervariable region paired-end amplicon sequencing was performed using the ILLUMINA® MISEQ®. Using QIIME and custom scripts, sequences were quality filtered. Paired-end reads were assembled and compared to the Greengenes database, clustered at 96% by UCLUST. After data normalization, sample-to-sample distance was measured using weighted UniFrac on Operational Taxonomic Unit (OTU) abundance data (utilizes taxon abundance differences across samples, employing a pair-wise normalization by dividing the sum of differences by the sum of all abundances). Bray-Curtis distances were measured using pair-wise normalization by dividing the sum of differences by the sum of all detected OTU abundances. In all Bray-Curtis measurements, a donor matched fresh sample that had been extracted shortly after collection was used as one side of the pair-wise comparison. Analysis of the Shannon Index (SI) for each stabilization method was performed by measuring the proportion of each OTU relative to the total number of OTUs, and then multiplied by the natural logarithm of this proportion. Summation of the resulting product across all OTUs produced the SI for each sample. Sample collection methods were compared using the Mann-Whitney test.

Results

The present composition maintains microbiome profile neutrality at the point-of-collection The study of the microbiome requires that the profile generated represents the in vivo microbial communities present in the donor; thus, the collection and stabilization method should not introduce changes to the microbiome.

Figure 21:
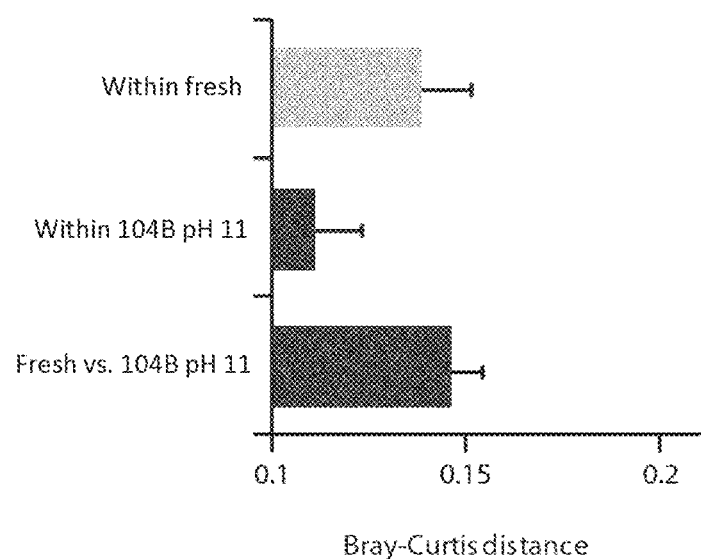
FIG. 21 shows Bray-Curtis dissimilarity distances within and between fresh and 104B pH 11 stabilized samples. Mann-Whitney test showed comparable dissimilarity in all conditions, no statistical difference was observed.

The use of chemical stabilization buffers can potentially modify the microbial composition of the sample by accelerating growth of some microbes while allowing the decay of others. In ideal conditions, the stabilization liquid should be neutral (i.e., it should not introduce any bias to the microbiome). Comparison of the 16S rRNA microbiome profile from fresh and 104B pH 11-stabilized t=0 samples showed that the present composition maintains a neutral profile and does not introduce bias (FIG. 21).

The study of relative OTU abundance by different statistical methods (e.g., Weighted UniFrac) provides a valuable description of the microbial community; however, it can obscure the understanding of the microbial community by minimizing the contribution of low abundance microbes. Proper study of the microbiome profile requires the preservation of the "richness" of the microbial communities. Richness is defined as the enumeration of microbial species (OTUs) present in the sample and is highly susceptible to environmental conditions, including changes in temperature, pH, oxygen concentration and chemical composition. These and other factors can induce bacterial growth or decay, thereby altering the number of OTUs detected in the sample.

Figure 22:
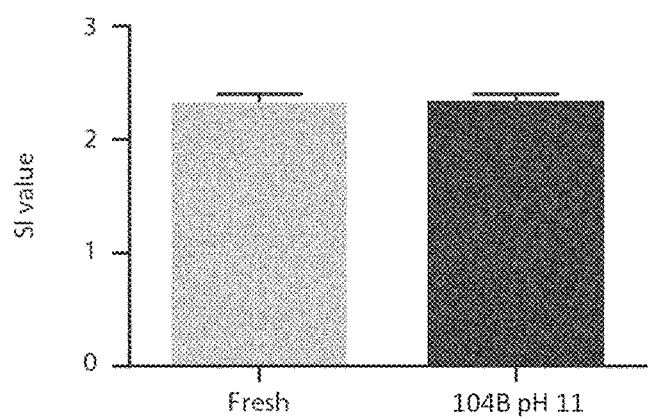
FIG. 22 illustrates that 104B pH 11 stabilized samples preserves richness. Richness was assessed by assigning presence/absence to individual OTUs and compared using Shannon-Index. Mann-Whitney test showed no significant differences between fresh and 104B pH 11 samples.

Fresh and 104B pH 11 stabilized samples from 6 donors were extracted shortly after collection. The microbial OTUs identified in 104B pH 11 samples were compared with the OTUs present in corresponding fresh samples. Shannon Index (SI) for diversity was calculated by converting OTU abundance data into presence/absence calls. Mann-Whitney test on the SI values showed no significant difference between 104B pH 11 and fresh samples, indicating that 104B pH 11 had no impact on the richness of the samples (FIG. 22).

Sources of Variability in Fecal Sample Collection

Figure 23:
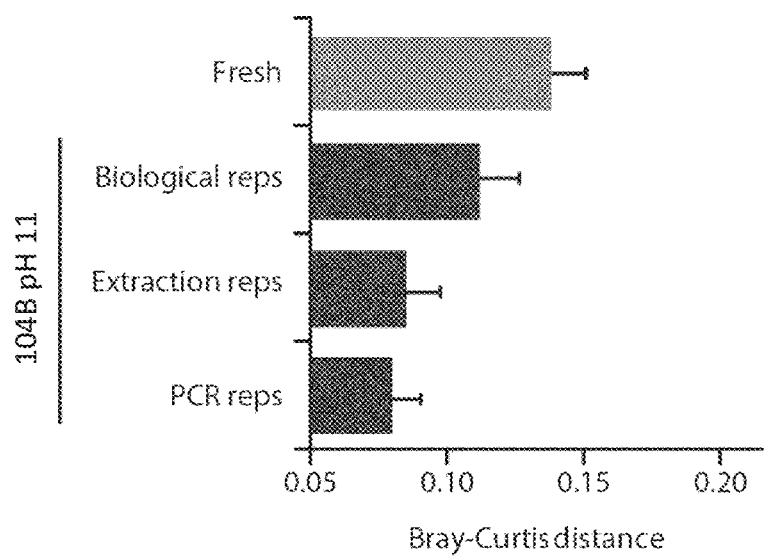
FIG. 23 illustrates that 104B pH 11 samples render highly reproducible microbiome profiles. Mann-Whitney tests on Bray-Curtis distances showed comparable dissimilarity in triplicate samples.

Bray-Curtis analysis showed systematic dissimilarity within replicates of fresh and 104B pH 11 t=0 samples. To understand the sources of such dissimilarity, the variability introduced during collection and processing of fecal samples was evaluated. Biological variability was assessed by generating microbiome profiles from three fresh and three 104B pH 11 samples collected from different sites within the same bulk sample. Technical variability was addressed using 104B pH 11 collected samples because this collection system provides homogenized liquid samples, reducing experimental errors during processing. The profiles of replicate DNA extractions from the same tube (extraction variability) and replicate PCR/sequencing from the same DNA (sequencing variability) were compared. Bray Curtis dissimilarity distances were generated within the replicate groups and are shown in FIG. 23.

Similar variability was observed in biological replicates of fresh and 104B pH 11 collected samples (Bray-Curtis distances 0.14±0.01 and 0.11±0.01, respectively). Analysis showed that technical and biological variability introduce some dissimilarity to the 16S rRNA microbiome profile (Bray-Curtis distances biological variability 0.11; extraction variability 0.09 and sequencing variability 0.08). In conclusion, the source of dissimilarity observed can be explained by the technical or biological variability and that 104B pH 11 does not introduce any bias.

104B pH 11 effectively preserves microbiome profiles for at least 14 days at room temperature In addition to maintaining profile neutrality, the study of the microbiome requires the accurate preservation of microbial community structure over time. We evaluated the capability of 104B pH 11 to stabilize samples during storage at 23° C. for 14 days.

Figure 24:
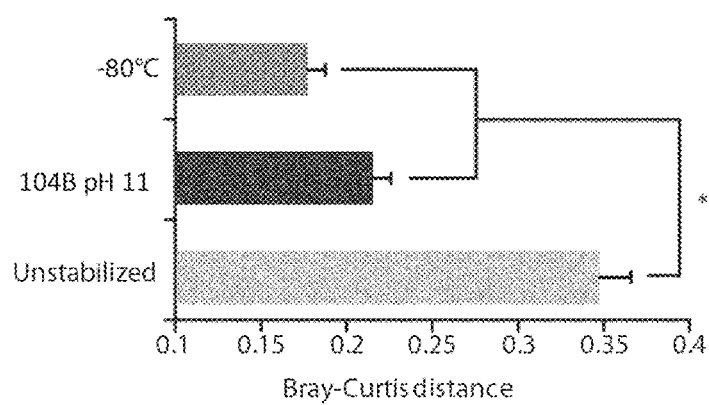
FIG. 24 shows Bray-Curtis distance dissimilarity between unstabilized and 104B pH 11 (14 days at 23° C.) and frozen (14 days at −80° C.) fecal samples when compared with fresh samples. Significant dissimilarity was assessed using Mann-Whitney (*P≤0.05).

Paired 104B pH 11-stabilized and fresh samples were extracted at Time Zero (T0) and again after storage at room temperature (23° C.) for 14 days. Fresh samples were also stored at −80° C. for 14 days as a control. The similarity of the samples was evaluated using Bray-Curtis distances. Mann-Whitney analysis showed no significant differences between 104B pH 11 samples at 23° C. for 14 days and −80° C. samples, when compared with corresponding fresh samples (FIG. 24). In contrast, unstabilized samples showed significant dissimilarity when compared either to −80° C. control or 104B pH 11 stored at room temperature.

Figure 25:
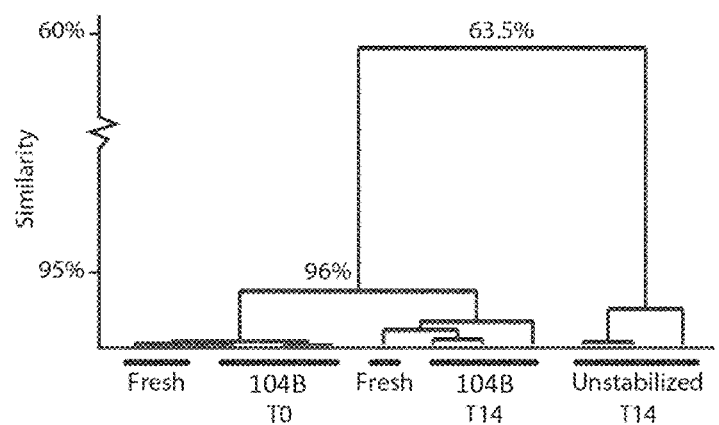
FIG. 25 shows a dendrogram of microbiome weighted Unifrac % similarity of a representative donor. Extractions from three biological replicates were performed for each condition. Low % similarity to fresh sample indicates changes in the microbiome profile over time.

In order to understand the reproducibility among replicates, a cluster analysis of weighted Unifrac was performed using fresh, 104B pH 11 collected samples (T0 and T14 days) and unstabilized samples (T14 days). The resulting dendrogram (FIG. 25) shows tight clustering between fresh and 104B pH 11 stabilized samples, even after 14 days (96% similarity). Unstabilized samples clustered together with a high separation from the fresh profile (~63% similarity). Proper stabilization therefore has a large effect on profile clustering over time.

Figure 26:
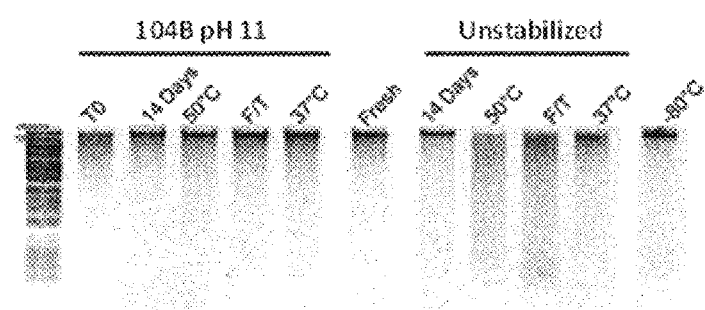
FIG. 26 illustrates DNA integrity of 104B pH 11 samples subjected to simulated transport conditions. Representative donors' samples were stored at 23° C. for 14 days, 50° C. for 1 day, 37° C. for 3 days or exposed to multiple freeze-thaw cycles. Fresh samples were also stored at −80° C. for 14 days as a control.

104B pH 11 effectively preserves the microbiome profile under simulated transport conditions Samples are commonly exposed to undesirable conditions during transport from the point of collection to the processing laboratory. To simulate standard shipping conditions, unstabilized and 104B pH 11 stabilized samples were exposed to 50° C. for 1 day, 37° C. for 3 days or multiple freeze-thaw (F/T) cycles. 104B pH 11 preserved high molecular weight DNA bands whereas unstabilized samples showed various degrees of degradation, particularly when exposed to 50° C. or freeze-thaw cycles (FIG. 26).

Figure 27:
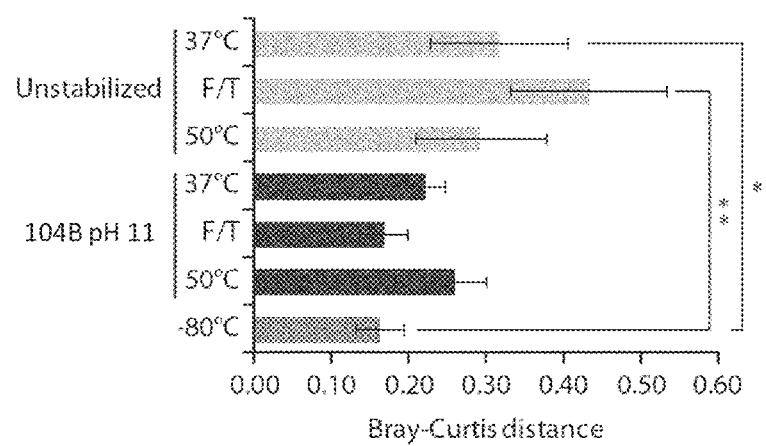
FIG. 27 illustrates Bray-Curtis distance dissimilarity of 104B pH 11 samples exposed to simulated shipping conditions. Mann-Whitney test showed no differences between 104B pH 11 samples stored at various temperatures and those stored at −80° C. Significant dissimilarity was observed in unstabilized samples held at 37° C. or subjected to freeze-thaw (F/T) conditions when compared to paired −80° C. samples (P≤0.05 and P≤0.01, respectively).

Finally, 16S rRNA analysis confirmed that 104B pH 11 preserves the microbial community structure even at extreme temperatures. Mann-Whitney test comparing Bray-Curtis distances of 104B pH 11 samples subjected to common shipping temperatures and paired samples held at −80° C. showed no significant differences. Conversely, unstabilized samples held at 37° C. or subjected to freeze-thaw cycles showed significant differences when compared with samples held at −80° C. (FIG. 27).

Conclusions

Stabilization, in the context of Metagenomics, is a multi-dimensional attribute that encompasses: a) neutrality (ability to capture unbiased profiles), b) reproducibility (homogenous sample material from which highly concordant aliquots can be taken), and c) integrity (molecular weight), as measured over time. Based on tightly controlled experiments and rigorous analysis, 104B pH 11 effectively stabilized gut microbiota in human feces through real-life shipping and handling conditions. This is of utmost importance to cost-effective scaling of MWAS, as well as optimizing data quality for biomarker discovery and development.

Example 11—Further Studies on the Role of Chelating Agents in Sample Stabilization at Elevated Temperatures The stability of the microbial profile within the sample is also sensitive to elevated temperatures. In these conditions not only may harmful nucleases potentially be activated, but also some species may begin to proliferate. The presence of a chelating agent (CDTA) is especially beneficial in this case in order to arrest the action of DNAses, as well as inhibiting bacterial growth.

In this experiment, healthy donors collected feces and transferred 400 mg of feces into a tube containing a single 7.9 mm stainless steel ball and 2 mL of the present composition with varied final concentrations of the chelating agent CDTA: a) 300 mM CDTA, 50 mM β-alanine, 23.5% ethanol, 0.5% SDS, 0.1% Antifoam A, pH 11 ("104B pH11"); b) 150 mM CDTA, 50 mM β-alanine, 23.5% ethanol, 0.5% SDS, 0.1% Antifoam A, pH 11, or c) 50 mM β-alanine, 23.5% ethanol, 0.5% SDS, 0.1% Antifoam A, pH 11 (no chelating agent). The samples were homogenized with hand shaking (mix) and then returned to the lab under room temperature conditions. Within 24 hours of sample collection, a 250 µL aliquot was removed from each tube for DNA extraction (T=0). The collected samples were then stored at 40° C. for 5 days (T=5) prior to DNA extraction from a second aliquot. Purified DNA was quantified and then resolved as bacterial community profiles or fingerprints using DGGE to separate 16S rRNA gene PCR amplicons. Percent similarity between samples (lanes on DGGE gel), compared to the control sample at T=0 for each composition, was calculated separately using Syngene GeneTools software (see Materials and Methods).

Figure 28:
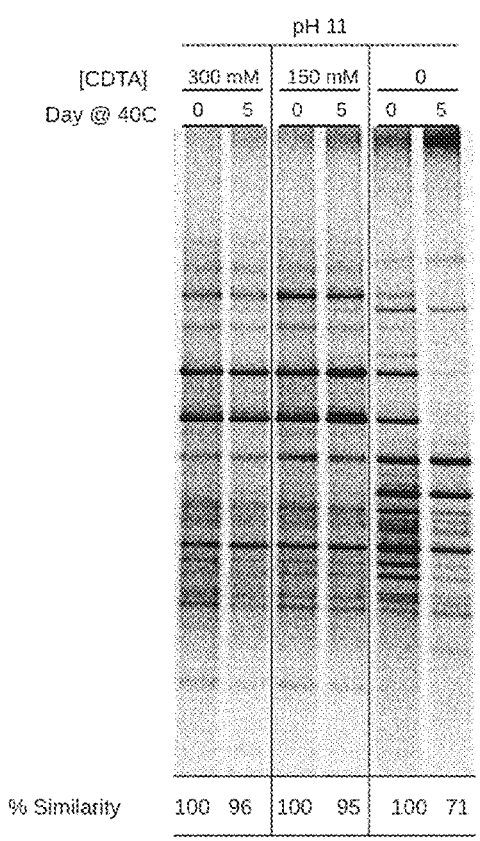
FIG. 28 shows DGGE analysis of the bacterial community profile of a fecal sample from 2 donors treated with the present composition containing varied concentrations of CDTA, and with a composition containing no CDTA, for 5 days at 40° C.

FIG. 28 demonstrates superior percent similarities or microbiome profile stability at elevated temperatures between the 'day 5' samples and 'day 0' for the present composition when CDTA is present at a concentration of 150 mM or 300 mM as compared to the composition without CDTA. This indicates that a chelating agent is required in the present composition in order to maintain the microbial profile stability at elevated temperatures. For the compositions with 300 mM and 150 mM CDTA, the microbial profiles at 'day 5' were 96% and 95% similar, respectively, as compared to 'day 0' when feces samples were stored at 40° C. In comparison, the microbial profile at 'day 5' in the composition with no CDTA was 71%, as compared to 'day 0' when feces samples were stored at 40° C.

Example 12—Superior Stabilization of Samples in the Present Composition as Compared to Prior Art Compositions Nucleic acids in patient samples tend to degrade after they have been removed from the patient. This degradation can diminish the effectiveness of a nucleic acid integrity assay that scores a sample as diseased (e.g. cancerous) based on the presence of intact nucleic acids. A P Shuber and D H Whitney (US 2008/0124714) describe a method for stabilizing nucleic acids in tissue and body fluid samples whereby the stabilization solution includes a buffer, a salt, and a chelating agent (e.g. "TEN buffer").

In this experiment, healthy donors collected feces and transferred either 400 mg of feces into a tube containing a single 7.9 mm stainless steel ball and 2 mL of the present composition (Composition 1; 300 mM CDTA, 50 mM β-alanine, 23.5% ethanol, 0.5% SDS, 0.1% Antifoam A, pH 11 ("104B pH 11")) or ii) approximately 400 mg of feces into a tube containing 2 mL of "TEN Buffer" (Composition 2; 10 mM Tris-HCl, 1 mM EDTA, 150 mM NaCl, pH 8, US2008/0124714). The samples in both tubes were homogenized with hand shaking (mix) and then returned to the lab under room temperature conditions. Within 24 hours of sample collection, a 250 µL aliquot was removed from each tube for DNA extraction (T=0) and then stored under room temperature conditions for 21 days (T=21) prior to DNA extraction from a second aliquot. Purified DNA was quantified and then resolved as bacterial community profiles or fingerprints using DGGE to separate 16S rRNA gene PCR amplicons. Percent similarity between samples (lanes on DGGE gel), compared to the control sample at T=0 for each composition, was calculated separately using Syngene GeneTools software (see Materials and Methods).

Figure 29:
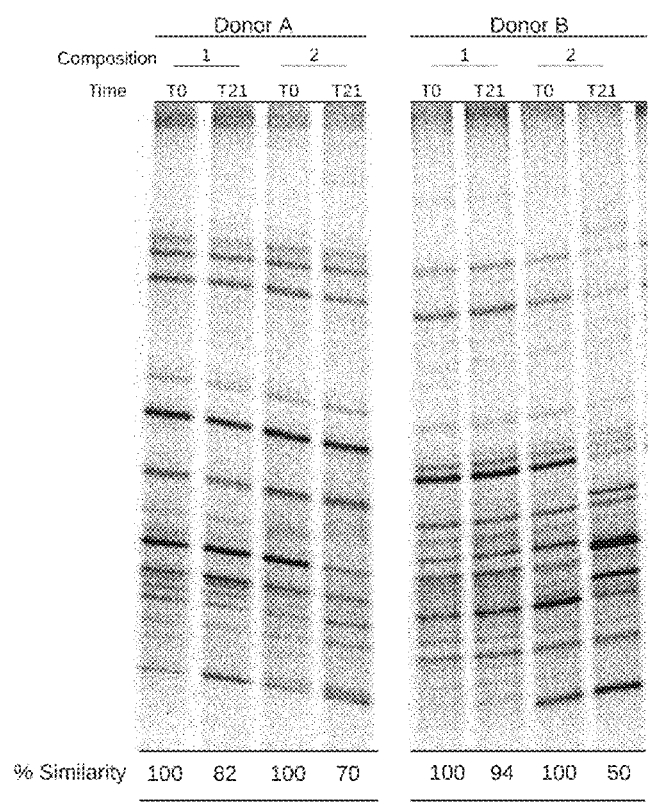
FIG. 29 shows DGGE analysis of the bacterial community profiles of fecal samples from 2 donors treated with the present composition "104B pH 11" or TEN buffer for 21 days at ambient temperature.

FIG. 29 illustrates superior percent similarities or microbiome profile stability between the 'day 21' samples and 'day 0' for the present composition as compared to the TEN buffer composition, indicating that the present composition offers improved DNA stability over other known compositions in the art. Donor A and B microbial profiles at 'day 21' were 82% and 94% similar, respectively, as compared to 'day 0' when feces samples were stored in the present "104B pH 11" composition. In comparison, donor A and B microbial profiles at 'day 21' were 70% and 50% similar, respectively, as compared to 'day 0' when feces samples were stored in the composition of US 2008/0124714.

US2008/0124714 also makes reference to a "stabilization buffer" consisting of 0.5 M Tris, 0.15M EDTA, and 10 mM NaCl (pH 9.0) in the Materials and Methods section at [0059]. However, it is noted that the only stabilizing buffer/solution referenced with specificity in the subsequent Examples is the "TEN buffer" noted above, and the claims and teaching of the description around the stabilizing solution are also directed to embodiments encompassing the "TEN buffer". As such, it is not apparent that the "stabilization buffer" was tested, or that it would work in the methods taught in US2008/0124714. Nonetheless, a comparative study was conducted comparing the performance of the above "stabilization buffer" of US2008/0124714 relative to the present composition containing 150 mM CDTA, 50 mM β-alanine, 23.5% ethanol, 0.5% SDS, 0.1% Antifoam A, pH 11, under the same conditions as described in Example 1.

During assessment of microbiome stability with composition and time, amplification using PCR of bacterial 16S rRNA gene and DGGE analysis of the amplicons showed that the present composition with 150 mM CDTA at pH 11 maintained a greater percent similarity (86%) to the control (T=0) after a 30-day incubation than did the "stabilization buffer" of US 2008/0124714 containing 150 mM EDTA at pH 9.0 (79%).

The compositions of the present application therefore provide superior stabilization of microbiome profiles in fecal samples relative to the compositions disclosed in US 2008/0124714.

REFERENCES

1. Lee Y K and Mazmanian S K (2010) Has the microbiota played a critical role in the evolution of the adaptive immune system? *Science* 24: 1768-1773.
2. Aries V, Crowther J S, Drasar B S, Hill M J, Williams R E O (1969) Bacteria and the aetiology of cancer of the large bowel. *Gut* 10: 334-335.
3. Moore W E C and Moore L H (1995) Intestinal floras of populations that have a high risk of colon cancer. *Applied Envir Microbiol* 61 (9): 3202-3207.
4. Parsonnet J, Friedman G D, Vandersteen D P, Chang Y, Vogelman J H, Orentreich N, Sibley R K (1991) *Helicobacter pylori* infection and the risk of gastric carcinoma. *N Engl J Med* 325: 1127-1131.
5. Grenham S, Clarke G, Cryan J F, Dinan T G (2011) Brain-gut-microbe communication in health and disease. *Front Physio* 2: 94.

6. Kinross J M, Darzi A W, Nicholson J K (2011) Gut microbiome-host interactions in health and disease. *Genome Medicine* 3:14.
7. Van Nood Els et al. (2013) Duodenal infusion of donor feces for recurrent *Clostridium difficile*. *N Engl J Med* 368 (5): 407-415.
8. Apajalahti J H A, Kettunen A, Nurminen P H, Jatila H, Holben W E (2003) Selective plating underestimates abundance and shows differential recovery of Bifidobacterial species from human feces. *Appl Environ Microbiol* 69(9): 5731-5735.
9. O'Sullivan D (2000) Methods for analysis of the intestinal microflora. *Current Issues in Intestinal Microbiology* 1(2): 39-50.
10. Walker A W, Ince J, Duncan S H, Webster L M, Holtrop G, Ze X, Brown D, Stares M D, Scott P, Bergerat A, Louis P, McIntosh F, Johnstone A M, Lobley G E, Parkhill J, Flint H J (2011) *International Society for Microbial Ecology Journal* 5: 220-230.
11. Wu G D, Chen J, Hoffmann C, Bittinger K, Chen Y-Y, Keilbaugh S A, Bewtra M, Knights D, Walters W A, Knight R, Sinha R, Gilroy E, Gupta K, Baldassano R, Nessel L, Li H, Bushman F D, Lewis J D (2011) Linking long-term dietary patterns with gut microbial enterotypes. *Science* 334: 105-108.
12. Ley R E, Knight R, Gordon J I (2007) The human microbiome: eliminating the biomedical/environmental dichotomy in microbial ecology. *Environ Microbiol* 9: 3-4.
13. Bahl M I, Bergstrom A, Licht T R (2012) Freezing fecal samples prior to DNA extraction affects the Firmicutes to Bacteroidetes ratio determined by downstream quantitative PCR analysis. *FEBS Microbiol Lett* 329: 193-197.
14. Olson J, Whitney D H, Durkee K, Shuber A P (2005) DNA stabilization is critical for maximizing performance of fecal DNA-based colorectal cancer tests. *Diagn Mol Pathol* 14(3): 183-191.
15. Song Y, Garg S, Girotra M, Maddox C, von Rosenvinge E C, Dutta A, Dutta S, Fricke W F (2013) Microbiota dynamics in patients treated with fecal microbiota transplantation for recurrent *Clostridium difficile* infection. *PLOS ONE* 8(11): 1-11.
16. Van der Giessen J W B, Eger A, Haagsma J, Haring R M, Gaastra W, van der Zeijst B A M (1992) Amplification of 16S rRNA sequences to detect *Mycobacterium paratuberculosis*. *J Med Microbiol* 36: 255-263.
17. Hurley S S, Splitter G A, Welch R A. Test for Johne's Disease. U.S. Pat. No. 4,918,178
18. Kojima K. Process of extracting nucleic acid and process of simultaneously carrying out extraction and purification of nucleic acid. U.S. Pat. No. 6,852,495
19. Ariefdjohan M W, Savaiano D A, Nakatsu C H (2010) Comparison of DNA extraction kits for PCR-DGGE analysis of human intestinal microbial communities from fecal specimens. *Nutr J* 9: 23.
20. Smith B, Li N, Andersen A S, Slotved H C, Krogfelt K A (2011) Optimising bacterial DNA extraction from faecal samples: comparison of three methods. *Open Microbiol J* 5: 14-17.
21. McInnes P, Cutting M (2010) Manual of procedures for human microbiome project. Core Microbiome Sampling Protocol A; Protocol #07-001 (version 12.0)
22. Brusa T, Canzi E, Pacini N, Zancho R, Farrari A (1989) Oxygen tolerance of anaerobic bacteria isolated from human feces. *Curr Microbiol* 19: 39-43.
23. US 2008/0124714 (A. P. Shuber and D. H. Whitney).

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. The scope of the claims should not be limited to the preferred embodiments set for the description, but should be given the broadest interpretation consistent with the description as a whole.

The embodiments of the invention in which an exclusive property or privilege is claimed are defined as follows:

1. An aqueous composition comprising a chelating agent wherein the chelating agent is present at a concentration of at least 150 mM, wherein the composition has a pH of at least 9.5;
   wherein the chelating agent is selected from 1,2-cyclohexanediamine tetraacetic acid (CDTA), diethylenetriamine pentaacetic acid (DTPA), tetraazacyclododecanetetraacetic acid (DOTA), tetraazacyclotetradecanetetraacetic acid (TETA), desferioximine, or chelator analogs thereof;
   wherein the composition stabilizes nucleic acid contained in a biological sample at ambient temperature.

2. The composition of claim 1, wherein the nucleic acid is deoxyribonucleic acid (DNA).

3. The composition of claim 1, wherein the biological sample is selected from a fecal sample, a soil sample, a sewage sample, a wastewater sample, or a water sample.

4. The composition of claim 3, wherein the nucleic acid is microbial DNA and the composition is for stabilizing a microbiome profile of the biological sample.

5. The composition of claim 1, wherein the biological sample is a fecal sample obtained from a mammal.

6. The composition of claim 5, wherein the mammal is a human, and the nucleic acid is human DNA.

7. The composition of claim 1, wherein the composition comprises one or more of the following characteristics:
   (i) the chelating agent is CDTA;
   (ii) the concentration of the chelating agent is from 150 mM to about 500 mM, or from about 250 mM to about 350 mM; and
   (iii) the concentration of the chelating agent is about 300 mM.

8. The composition of claim 1, wherein the composition has a pH of from 9.5 to 11.5, or from 10.5 to 11.5, or 11.

9. The composition of claim 1, wherein the composition further comprises one or more of the following:
   (i) at least one buffering agent capable of buffering in the pH range 9.5 to 11.5; and
   (ii) a water-soluble organic solvent.

10. The composition of claim 9, wherein the composition comprises a water soluble organic solvent, the water-soluble organic solvent is ethanol, and the composition further comprises one or more of the following characteristics:
   (i) the ethanol is present in the composition at a concentration of less than about 30% by volume; and
   (ii) the ethanol is present in the composition at a concentration of less than about 24% by volume.

11. The composition of claim 1, wherein the composition further comprises one or more of the following:
   (i) a detergent; and
   (ii) an antifoaming agent.

12. The composition of claim 1, wherein the nucleic acid is DNA, the biological sample is a fecal sample obtained from a mammal, the composition has a pH of from 10.5 to 11.5, and the composition comprises, consists essentially of, or consists of:
   CDTA in an amount of from about 250 mM to about 350 mM, or about 300 mM;
   β-alanine in an amount of from about 30 mM to about 70 mM, or about 50 mM;
   ethanol in an amount of from about 21.5% to about 23.5% by volume, or about 23.5% by volume;
   sodium dodecyl sulfate in an amount of from about 0 to about 1% (w/v), or about 0.5% (w/v); and
   Antifoam A in an amount of from about 0 to about 0.2% (v/v), or about 0.1% (v/v).

13. The composition of claim 12, wherein the nucleic acid is microbial DNA and the composition is for stabilizing a microbiome profile of the fecal sample.

14. The composition of claim 1, wherein the nucleic acid is ribonucleic acid (RNA).

15. A kit for stabilizing nucleic acid contained in a biological sample at ambient temperature, the kit comprising:
   a) a sample container having a resealable closure;
   b) an aqueous composition comprising a chelating agent wherein the chelating agent is present at a concentration of at least 150 mM, wherein the composition has a pH of at least 9.5, wherein said composition is optionally contained within the sample container;
   c) a homogenization means, optionally contained within the sample container;
   d) a means to transfer the biological sample, or a portion thereof, into the sample container; and
   e) instructions for use.

16. The kit of claim 15, wherein the nucleic acid is deoxyribonucleic acid (DNA).

17. The kit of claim 15, wherein the biological sample is selected from a fecal sample, a soil sample, a sewage sample, a wastewater sample, or a water sample.

18. The kit of claim 17, wherein the nucleic acid is microbial DNA and the kit is for stabilizing a microbiome profile of the biological sample.

19. The kit of claim 15, wherein the biological sample is a fecal sample obtained from a mammal.

20. The kit of claim 19, wherein the mammal is a human, and the nucleic acid is human DNA.

21. The kit of claim 15, wherein the composition comprises one or more of the following characteristics:
   (i) the chelating agent is selected from CDTA, DTPA, DOTA, TETA, desferioximine, or chelator analogs thereof;
   (ii) the chelating agent is CDTA;
   (iii) the concentration of the chelating agent is from 150 mM to about 500 mM, or from about 250 mM to about 350 mM; and
   (iv) the concentration of the chelating agent is about 300 mM.

22. The kit of claim 15, wherein the composition has a pH of from 9.5 to 11.5, or from 10.5 to 11.5, or 11.

23. The kit of claim 15, wherein the composition further comprises one or more of the following:
   (i) at least one buffering agent capable of buffering in the pH range 9.5 to 11.5; and
   (ii) a water-soluble organic solvent.

24. The kit of claim 23, wherein the composition comprises a water soluble organic solvent, the water-soluble organic solvent is ethanol, and the composition further comprises one or more of the following characteristics:
   (i) the ethanol is present in the composition at a concentration of less than about 30% by volume; and
   (ii) the ethanol is present in the composition at a concentration of less than about 24% by volume.

25. The kit of claim 15, wherein the composition further comprises one or more of the following:
   (i) a detergent; and
   (ii) an antifoaming agent.

26. The kit of claim 15, wherein the homogenization means is at least one mixing ball.

27. The kit of claim 26, further comprising one or more of the following characteristics:
   (i) the at least one mixing ball is a stainless steel mixing ball or a tungsten carbide mixing ball;
   (ii) the at least one mixing ball is a stainless steel mixing ball having a diameter of about 5.6-11.1 mm and a density of at least about 7.6 g/cm$^3$; and
   (iii) the at least one mixing ball is a stainless steel mixing ball, wherein the stainless steel mixing ball has a diameter of about 7.1-8.7 mm, and the sample container is a round-bottom tube having an internal diameter of about 12.9 mm.

28. The kit of claim 15, wherein the nucleic acid is DNA, the biological sample is a fecal sample obtained from a mammal, the composition has a pH of from 10.5 to 11.5, and the composition comprises, consists essentially of, or consists of:
   CDTA in an amount of from about 250 mM to about 350 mM, or about 300 mM;
   β-alanine in an amount of from about 30 mM to about 70 mM, or about 50 mM;
   ethanol in an amount of from about 21.5% to about 23.5% by volume, or about 23.5% by volume;
   sodium dodecyl sulfate in an amount of from about 0 to about 1% (w/v), or about 0.5% (w/v); and
   Antifoam A in an amount of from about 0 to about 0.2% (v/v), or about 0.1% (v/v).

29. The kit of claim 28, wherein the nucleic acid is microbial DNA and the kit is for stabilizing a microbiome profile of the biological sample.

30. The kit of claim 28, wherein the homogenization means is at least one stainless steel mixing ball having a diameter of about 5.6-11.1 mm and a density of at least about 7.6 g/cm$^3$, and the sample container is a round-bottom tube having an internal diameter of about 12.9 mm.

31. The kit of claim 15, wherein the nucleic acid is ribonucleic acid (RNA).

\* \* \* \* \*

SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: PRIMER: PPUN518R

<400> SEQUENCE: 1
attaccgcgg ctgctgg                                                    17

<210> SEQ ID NO 2
<211> LENGTH: 57
<212> TYPE: DNA
<213> ORGANISM: Artificial Sequence
<220> FEATURE:
<223> OTHER INFORMATION: PRIMER: PRBA338F

<400> SEQUENCE: 2
cgcccgcgcg cggcgggcgg ggcgggggca cgggggggact cctacgggag gcagcag      57

```
<210> SEQ ID NO 3
<211> LENGTH: 17
<212> TYPE: DNA
<213> ORGANISM: Artificial Sequence
<220> FEATURE:
<223> OTHER INFORMATION: Primer: hTSm143F

<400> SEQUENCE: 3
gccctctgcc agttcta                                                  17

<210> SEQ ID NO 4
<211> LENGTH: 16
<212> TYPE: DNA
<213> ORGANISM: Artificial Sequence
<220> FEATURE:
<223> OTHER INFORMATION: PRIMER: hTSm143R

<400> SEQUENCE: 4
ttcaggcccg tgatgt                                                   16
```